US009752192B2

(12) United States Patent
Millonig et al.

(10) Patent No.: US 9,752,192 B2
(45) Date of Patent: Sep. 5, 2017

(54) COMPOSITIONS AND METHODS FOR DIAGNOSING AUTISM

(71) Applicant: Rutgers, The State University of New Jersey, New Brunswick, NJ (US)

(72) Inventors: James H. Millonig, Princeton Junction, NJ (US); Linda Brzustowicz, Madison, NJ (US); Neda Gharani, North Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 18 days.

(21) Appl. No.: 13/790,309

(22) Filed: Mar. 8, 2013

(65) Prior Publication Data

US 2013/0183669 A1 Jul. 18, 2013

Related U.S. Application Data

(63) Continuation-in-part of application No. 12/629,474, filed on Dec. 2, 2009, now abandoned, which is a continuation of application No. 11/324,563, filed on Jan. 3, 2006, now Pat. No. 7,629,123, which is a continuation-in-part of application No. PCT/US2004/021301, filed on Jul. 1, 2004.

(60) Provisional application No. 60/721,192, filed on Sep. 28, 2005, provisional application No. 60/484,633, filed on Jul. 3, 2003.

(51) Int. Cl.
*C07H 21/02* (2006.01)
*C07H 21/04* (2006.01)
*C12Q 1/68* (2006.01)

(52) U.S. Cl.
CPC ..... *C12Q 1/6883* (2013.01); *C12Q 2600/156* (2013.01)

(58) Field of Classification Search
CPC ............ C12Q 1/6883; C12Q 2600/156; C12Q 2600/16; C12Q 2600/72
See application file for complete search history.

(56) References Cited

U.S. PATENT DOCUMENTS

| 7,629,123 | B2 | 12/2009 | Millonig et al. ............. 435/6.16 |
| 2001/0014446 | A1* | 8/2001 | Heroux et al. .................... 435/6 |
| 2007/0071677 | A1 | 3/2007 | Park et al. ................... 424/1.69 |
| 2010/0136565 | A1 | 6/2010 | Millonig et al. ............. 435/325 |

OTHER PUBLICATIONS

Rothstein J.D. et al Proc. Natl. Acad. Sci. USA (May 1994) vol. 91 pp. 4155-4159.*
New England Biolabs 1998/1999 Catalog, Random Primers catalog #1256, pp. 121 and 284.*
Neoh S.-H. et al. J Clin Pathol 1999;52:766-769.*
Reference SNP (refSNP) Cluster Report: rs1861972 (ss2736084) (2001), pp. 1-4 pritned from www.ncbi.nlm.nih.gov.*
Reference SNP (refSNP) Cluster Report: rs2361688 (ss3318553) (2001), pp. 1-3 pritned from www.ncbi.nlm.nih.gov.*
Auranen et al. "A Genomewide Screen for Autism-Spectrum Disorders: Evidence for a Major Susceptibility Locus on Chromosome 3q25-27" American Journal of Human Genetics 2002 71:777-790.
Hanks et al. "Rescue of the En-1 Mutant Phenotype by Replacement of En-1 with En-2" Science 1995 269:679-682.
Kuemerle et al. "Pattern Deformities and Cell Loss in Engrailed-2 Mutant Mice Suggest Two Separate Patterning Events During Cerebellar Development" The Journal of Neuroscience 1997 17(20):7881-7889.
Liu et al. "Early Anterior/Posterior Patterning of the Midbrain and Cerebellum" Annual Review of Neuroscience 2001 24:869-896.
Millen et al. "Abnormal Embryonic Cerebellar Development and Patterning of Postnatal Foliation in Two Mouse Engrailed-2 Mutants" Development 1994 120:695-706.
Millen et al. "A Role for En-2 and Other Murine Homologues of *Drosophila* Segment Polarity Genes in Regulating Positional Information in the Developing Cerebellum" Development 1995 121:3935-3945.
Petit et al. "Association Study with Two Markers of a Human Homeogene in Infantile Autism" Journal of Medical Genetics 1995 32:269-274.
Alarcon et al. "Evidence for a Language Quantitative Trait Locus on Chromosome 7q in Multiplex Autism Families" American Journal of Human Genetics 2002 70:60-71.
Lui et al. "A Genomewide Screen for Autism Susceptibility Loci" American Journal of Human Genetics 2001 69:327-340.
Logan et al. "Cloning and Sequence Comparison of the Mouse, Human and Chicken Engrailed Genes Reveal Potential Functional Domains and Regulator Regions" Developmental Genetics 1992 13:345-358.
Zhong et al. "No Association Between the EN2 Gene and Autistic Disorder" Journal of Medical Genetics 2003 40:1-4.
Treatment, CDC—Treatment, Autism Spectrum Disorders—NCBDDD (printed on Oct. 20, 2011) from online source www.cdc.gov/ncbddd/autism/treatment.html, pp. 1-6.
Pennisi, E. "A Closer Look at SNPs Suggests Difficulties" Science 1998 281(5384):1787-1789.
Lucentini, J. "Gene Association Studies Typically Wrong" The Scientist 2004 18:20.
Hegele, R.A. "SNP Judgments and Freedom of Association" Arteriosclerosis, Thrombosis, and Vascular Biology 2002 22:1058-1061.
Thisted, R.A. "What is a P-value?" (May 25, 1998), printed from http://www.stat.uchicago.edu/~thisted, pp. 1-6.
Rebhan et al.: GeneCards: encyclopedia for genes, proteins and diseases. 1997. GeneCard for [EN2][Aug. 20, 2007] World Wide Web URL: http://www.genecards.org/cgi-bin/carddisp.pl?gene=EN2&search=EN2&ortholog=all&stuff=txt#ort.

(Continued)

*Primary Examiner* — Stephen Kapushoc
(74) *Attorney, Agent, or Firm* — Licata & Tyrrell P.C.

(57) ABSTRACT

Mutations located within the gene encoding the homeobox transcription factor, ENGRAILED 2 (EN2), have now been identified as molecular markers associated with susceptibility for autism and related disorders. Thus, the present invention relates to compositions in the form of diagnostic kits, primers and target sequences, for use in methods for determining the predisposition, the onset or the presence of autism spectrum disorder in a mammal. Moreover, therapeutic methods for treating a person inflicted with, or predisposed to, an autism spectrum disorder based upon modulating the level or activity of EN2 are also provided.

2 Claims, No Drawings

(56) References Cited

OTHER PUBLICATIONS

Geschwind et al. "The Autism Genetic Resource Exchange: A Resource for the Study of Autism and Related Neuropsychiatric Conditions" American Journal of Human Genetics 2001 69:463-466.
Cheh et al. "En2 Knockout Mice Display Neurobehavioral and Neurochemical Alterations Relevant to Autism Spectrum Disorder" Brain Research 2006 1116(1):166-176.
Benayed et al. "Support for the Homeobox Transcription Factor Gene Engrailed 2 as an Autism Spectrum Disorder Susceptibility Locus" American Journal of Human Genetics 2005 77:851-868.
Gharani et al. "Association of the Homeobox Transcription Factor, Engrailed 2, 3, with Autism Spectrum Disorder" Molecular Psychiatry 2004 9:474-484.
Hirschhorn et al. "A Comprehensive Review of Genetic Association Studies" Genetics in Medicine 2002 4(2):45-61.
Ioannidis et al. "Replication Validity of Genetic Association Studies" Nature Genetics 2001 29:306-309.
Bartlett et al. "Three Autism Candidate Genes: A Synthesis of Human Genetic Analysis with Other Disciplines" International Journal of Developmental Neuroscience 2005 23(2-3):221-234.
Haga et al. "Gene-based SNP Discovery as Part of the Japanese Millennium Genome Project: Identification of 190 562 Genetic Variations in the Human Genome" Journal of Human Genetics 2002 47:605-610.
Zec et al. "Expression of the Homeobox-containing Genes EN1 and EN2 in Human Fetal Midgestational Medulla and Cerebellum" Journal of Neuropathology and Experimental Neurology 1997 56:236-242.
Hong et al. "DNA Polymorphisms of the Human Engrailed-like Genes, EN1 and EN2" Molecules and Cells 1993 3:101-107.
Alvarez-Erviti et al. "Delivery of siRNA to the Mouse Brain by Systemic Injection of Targeted Exosomes" Nature Biotechnology 2011 29(4):341-345.
Chen et al. "Synthesis of Oligodeoxyriboneucleotide N3'→P5' Phosphoramidates" Nucleic Acids Research 1995 23(14):2661-2668.
Chu et al. "Aptamer Mediated siRNA Delivery" Nucleic Acids Research 2006 34(10):e73, pp. 1-6.
Davidson et al. "Highly Efficient Small Interfering RNA Delivery to Primary Mammalian Neurons Induces MicroRNA-Like Effects before mRNA Degradation" The Journal of Neuroscience 2004 24(45):10040-10046.
Ge et al. "Zorro Locked Nucleic Acid Induces Sequence-Specific Gene Silencing" The FASEB Journal 2007 21:1902-1914.
Meade, B.R. and Dowdy, S.F. "Exogenous siRNA Delivery Using Peptide Transduction Domains/Cell Penetrating Peptides" Advanced Drug Delivery Reviews 2007 59:134-140.
Morris et al. "A Peptide Carrier for the Delivery of Biologically Active Proteins into Mammalian Cells" Nature Biotechnology 2001 19:1173-1176.
Nielsen, P.E. and Egholm, M. "An Introduction to Peptide Nucleic Acid" Current Issues in Molecular Biology 1999 1(2):89-104.
Pardridge, W.M. "shRNA and siRNA Delivery to the Brain" Advanced Drug Delivery Reviews 2007 59:141-152.
Ray, P. and White, R.R. "Aptamers for Targeted Drug Delivery" Pharmaceuticals 2010 3:1761-1778.
Ray, A. and Bengt, N. "Peptide Nucleic Acid (PNA): Its Medical and Biotechnical Applications and Promise for the Future" The FASEB Journal 2000 14:1041-1060.
Reynolds et al. "Synthesis and Thermodynamics of Oligonucleotides Containing Chirally Pure $R_p$ Methylphosphonate Linkages" Nucleic Acids Research 1996 24(22):4584-4591.
Veedu, R.N. and Wengel, J. "Locked Nucleic Acid as a Novel Class of Therapeutic Agents" RNA Biology 2009 6(3):321-323.
Zaghloul et al. "Optimizing Anti-gene Oligonucleotide 'Zorro-LNA' for Improved Strand Invasion into Duplex DNA" Nucleic Acids Research 2011 39(3):1142-1154.
Zhang et al. "Down-Modulation of Cancer Targets Using Locked Nucleic Acid (LNA)-based Antisense Oligonucleotides without Transfection" Gene Therapy 2011 18:326-333.
Office communication dated Oct. 11, 2007 from U.S. Appl. No. 11/324,563, filed Jan. 3, 2006.
Office communication dated Apr. 23, 2008 from U.S. Appl. No. 11/324,563, filed Jan. 3, 2006.
Office communication dated Feb. 6, 2009 from U.S. Appl. No. 11/324,563, filed Jan. 3, 2006.
Office communication dated Oct. 24, 2011 from U.S. Appl. No. 12/629,474, filed Dec. 2, 2009.
Office communication dated May 9, 2012 from U.S. Appl. No. 12/629,474, filed Dec. 2, 2009.
International Search Report from PCT/US2004/021301, Apr. 1, 2005.
International Preliminary Report on Patentability from PCT/US2004/021301, Jan. 3, 2006.
Benayed et al. "Support for the Homeobox Transcription Factor Gene Engrailed 2 as an Autism Spectrum Disorder Susceptibility Locus" The American Journal of Human Genetics 2005 77:851-868.
International Search Report from PCT/US2014/022398, Sep. 19, 2014.

* cited by examiner

US 9,752,192 B2

COMPOSITIONS AND METHODS FOR DIAGNOSING AUTISM

This application is a continuation-in-part of U.S. Ser. No. 12/629,474, filed Dec. 2, 2009, which is a continuation of U.S. Ser. No. 11/324,563 filed Jan. 3, 2006, now U.S. Pat. No. 7,629,123, which claims the benefit of priority from U.S. Provisional Patent Application Ser. No. 60/721,193 filed Sep. 28, 2005, and is a continuation-in-part of PCT/US2004/021301 filed Jul. 1, 2004, which claims benefit of U.S. Provisional Patent Application Ser. No. 60/484,633, filed Jul. 3, 2003, the contents of which are incorporated herein by reference in their entirety.

This invention was made with government support under contract numbers R01 MH70366 awarded by the National Institute of Mental Health, PO1 ES11256 awarded by the National Institutes of Health, and R829391 awarded by the U.S. Environmental Protection Agency. The government has certain rights in the invention.

BACKGROUND OF THE INVENTION

Autism spectrum disorder (AS) includes three separate diagnoses, which include autism, Asperger's syndrome and Pervasive Developmental Delay (PDD). PDD is characterized by developmental delays of sociability, communication and use of imagination. Asperger's syndrome is a more severe form of PDD but lacks the language and intelligence deficits normally associated with autism. Autism is exemplified by severe communication impairments, social interaction deficits and repetitive/stereotypic behaviors. Each of these disorders has specific diagnostic criteria as outlined by the American Psychiatric Association (APA) in its *Diagnostic & Statistical Manual of Mental Disorder's* (DSM-IV-TR).

Autism impacts the normal development of the brain in the areas of social interaction and communication skills. Children and adults with autism typically have difficulties in verbal and non-verbal communication, social interactions, and leisure or play activities.

There is no known single cause for autism, but it is generally accepted that it is caused by abnormalities in brain structure or function. Brain scans show differences in the shape and structure of the brain in autistic versus non-autistic children. Links between heredity, genetics and medical problems have been analysed. In many families, there appears to be a pattern of autism or related disabilities, further supporting a genetic basis to the disorder. While no one gene has been identified as causing autism, it appears that some children are born with a susceptibility to autism.

It has also been suggested that under certain conditions, a number of genes with altered levels or functions may interfere with brain development resulting in autism. On the other hand, certain developmental genes may be associated with autism, including the Wnt2 and reelin genes (Wassink, et al. (2001) *Am. J. Med. Genet.* 105:406-413; Persico, et al. (2001) *Mol. Psychiatry.* 6:150-159). Pregnancy or delivery as well as environmental factors such as viral infections, metabolic imbalances, and exposure to environmental chemicals have also been implicated.

Autism tends to occur more frequently than expected among individuals who have certain medical conditions, including Fragile X syndrome, tuberous sclerosis, congenital rubella syndrome, and untreated phenylketonuria (PKU). Some harmful substances ingested during pregnancy also have been associated with an increased risk of autism. In 2002, The Agency for Toxic Substances and Disease Registry (ATSDR) prepared a literature review of hazardous chemical exposures and autism and found no compelling evidence for an association; however, literature in this area was limited.

The question of a relationship between vaccines and autism continues has been debated. In a 2001 investigation by the Institute of Medicine, a committee concluded that the "evidence favors rejection of a causal relationship . . . between MMR vaccines and autistic spectrum disorders (ASD)." The committee acknowledged, however, that "they could not rule out" the possibility that the MMR vaccine could contribute to ASD in a small number of children. While other researchers agree the data does not support a link between the MMR and autism.

Whatever the cause, it is clear that children with autism and PDD are born with the disorder or born with the potential to develop it. Autism is not a mental illness. Children with autism are not unruly kids who choose not to behave. Furthermore, no known psychological factors in the development of the child have been shown to cause autism.

There are no medical tests for diagnosing autism. An accurate diagnosis must be based on observation of the individual's communication, behavior, and developmental levels. However, because many of the behaviors associated with autism are shared by other disorders, various medical tests may be ordered to rule out or identify other possible causes of the symptoms being exhibited.

A brief observation in a single setting cannot present a true picture of an individual's abilities and behaviors. Parental and other caregivers' input and developmental history are very important components of making an accurate diagnosis. At first glance, some persons with autism may appear to have mental retardation, a behavior disorder, problems with hearing, or even odd and eccentric behavior. To complicate matters further, these conditions can co-occur with autism. However, it is important to distinguish autism from other conditions, since an accurate diagnosis and early identification can provide the basis for building an appropriate and effective educational and treatment program.

Research indicates that early diagnosis is associated with dramatically better outcomes for individuals with autism. The earlier a child is diagnosed, the earlier the child can begin benefiting from one of the many specialized intervention approaches.

Accordingly, what is needed is a genetic marker to assess a subject's susceptibility to autism or a disease or disorder related thereto. Also needed is a genetic marker to diagnose autism, and the development of potential drugs or agents that have applications in treating autism or a disease or disorder related thereto, such as Asperger's Disorder or PDD.

The present invention addresses the unmet need for the identification of an autism susceptibility locus and the uses for early diagnostic and prognostic purposes.

SUMMARY OF THE INVENTION

There is provided, in accordance with the present invention, an isolated nucleic acid molecule which encodes human EN2, and the amino acid sequence of human EN2. Furthermore, there is provided, in accordance with the present invention, methods for determining a subject's susceptibility to autism or a disease or disorder related thereto, such as Asperger's Disorder or PDD using a variant allele of the Engrailed (EN2 [MIM131310]) gene, which maps to chromosome 7, in particular, to 7q36.3. Furthermore, transmission/disequilibrium tests (TDT), which were performed for two single nucleotide polymorphisms (Intron A/G and Intron C/T), revealed significant overtransmission of the A allele of Intron A/G and the C allele of Intron C/T (Intron A/G P=0.0009; Intron C/T P=0.0006). Haplotype analysis indicated that the A-C haplotype is specifically overtransmitted in autistic individuals (P=0.000062). Detection of such a variant allele in the genome of a subject is considered indicative of the subject's susceptibility to autism. Furthermore, a variant allele of the Engrailed gene is also useful to assay drugs and agents for potential use in treating autism or a disease or disorder related thereto, such as Asperger's Disorder or PDD.

Accordingly, a first aspect of the invention provides for an isolated variant allele of a human Engrailed gene (EN2), wherein the Engrailed gene comprises a DNA sequence of SEQ ID NO:1, and the variant allele comprises a DNA sequence having at least one single nucleotide polymorphism, wherein the at least one variation comprises a A to G transition at position 154556629; or a C to T transition at position 154556781 or a combination thereof, and wherein said variant allele correlates with the predisposition, the onset or the presence of autism spectrum disorder in a mammal.

A second aspect of the invention provides for a diagnostic method for determining the predisposition, the onset or the presence of autism spectrum disorder in a mammal, said method comprising detecting in said mammal the existence of a change in a segment of the genome, that segment located within the portion of chromosome 7 as set forth in SEQ ID NO:1. In one embodiment, the segment comprises the human EN2 gene and is located on chromosome 7 from about position 154552000 to about position 154560000. The autism spectrum disorder may be selected from the group consisting of autism, Asperger's disorder and Pervasive Development Delay (PDD). The segment of the genome may contain a mutation, and this mutation may be a deletion, an addition and a substitution of at least one nucleotide. Furthermore, the substitution may be a single nucleotide polymorphism (SNP) located at position 154556629. This substitution may comprise a G to A transition at position 154556629. Furthermore, the substitution may be a single nucleotide polymorphism (SNP) located at position 154556781. This substitution may comprise a T to C transition at position 154556781, or the substitution may be a combination of both SNPs.

In a third aspect, the present invention provides for a detectably labelled isolated variant allele of a human EN2 gene, wherein the EN2 gene comprises a DNA sequence of SEQ ID NO:1, and the variant allele comprises a DNA sequence having at least one variation in SEQ ID NO:1, wherein the at least one variation comprises a G to A transition at position 154556629; or a T to C transition at position 154556781 or a combination thereof.

Numerous detectable labels have applications in the present invention. For example the detectable label can be a radioactive element, such as the isotopes $^{3}$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re, to name only a few. Chemicals which fluoresce, or enzymes such as alkaline phosphatase or horseradish peroxidase, can also be used as detectable labels.

In a fourth aspect, the invention provides for a diagnostic method for determining that a person has a genetic abnormality that predisposes that person, or his or her offspring, to autism spectrum disorder, including autism, Asperger's disorder, or PDD, wherein said genetic abnormality is found on chromosome 7, said method comprising detecting, in that person, the existence of a change in a segment of the genome, that segment located within the portion of chromosome 7 as set forth in SEQ ID NO:1. The segment comprises the human EN2 gene which is located on chromosome 7 from about position 154552000 to about position 154560000, said segment having the sequence set forth is SEQ ID NO:1. The person diagnosed may not be autistic (i.e., may not exhibit any autistic symptoms or behaviors), however, if the person diagnosed has the genetic abnormality that predisposes that person to autism, then this diagnosis signifies that the person diagnosed could bear children who are predisposed to autism. The determination can be made before the person is born, as early as the blastocyst stage of embryonic development and throughout the fetal stage, or at any time after the person is born. It is sufficient that the abnormality occur in one chromosome of a person; i.e., the person can be heterozygous as regards the abnormality. In a specific embodiment, the invention provides for a method for determining whether a person has a genetic abnormality that predisposes such person to autism spectrum disorder, said method comprising examining chromosome 7 of said person, and detecting, where present, the existence of a change in a segment of the genome located in said chromosome 7, wherein said segment is set forth in SEQ ID NO:1.

The diagnostic method involves detecting changes in the Engrailed (EN2) gene. Changes (or mutations) are additions, deletions, or substitutions of at least one nucleotide. Thus, in one embodiment, the diagnostic method comprises detecting a change in a region of chromosome 7 spanning the EN2 gene. In the context of this application, the EN2 gene means the sequence necessary for transcription and translation such that normal levels of functional EN2 protein are generated. The substitution may be a single nucleotide polymorphism (SNP) located at position 154556629, and the substitution may consist of a guanine (G) to adenine (A) transition. Alternatively, the substitution may be a single nucleotide polymorphism (SNP) located at position 154556781 and may consist of a thymine (T) to cytosine (C) transition. In addition, since cis-regulatory regions needed for EN2 expression can be, for example, as far as 1000 kb away from the coding sequence of the gene, the EN2 gene also means a region on human Chromosome 7 of approximately 154010087-155102101 base pairs and encompasses the EN2 coding region (approximately 8000 base pairs) and flanking sequence.

In another embodiment, a diagnostic method useful for determining that a person has a genetic abnormality that predisposes that person to autism spectrum disorder is envisioned, said method comprising detecting in that person the existence of a mutation in the EN2 gene such that said mutation results in the deletion, addition, or substitution of at least one amino acid in the EN2 protein.

Another embodiment of the EN2 gene are the single nucleotide polymorphisms (SNPs) comprising a region amplifiable by polymerase chain reaction, wherein said region is amplified using a primer pair, wherein a primer is selected from the group consisting of the sequences set forth is SEQ ID NOs: 3, 4, 5, 6, 7, 8, 9 and 10. Accordingly, part of this invention is a diagnostic method for determining that a person has a genetic abnormality that predisposes that person to autism, said method comprising detecting, in that person, the existence of a change, i.e., a deletion, an addition or a substitution in a segment of the genome, that sequence located within the portion of chromosome 7 set forth in SEQ ID NO:1 (the EN2 gene), and amplifying portions of that sequence containing the SNPs identified herein, using primer pairs selected from the group consisting of the sequences set forth is SEQ ID NOs: 3, 4, 5, 6, 7, 8, 9 and 10.

Primer sequences that flank the EN2 transcript (i.e., the coding region) on chromosome 7 are:

Intron 1 A/G (rs1861972), Forward outer 5'-TGA AGC TGG GGC CAG ATG CTC CTA-3' (SEQ ID NO:3), Reverse outer 5'-CAT GGG GAA AGG GCA GAG GGA GGA G-3' (SEQ ID NO:4), Forward inner 5'-AGG CGA GGT CAC CAC TCC CTG CAA G-3' (SEQ ID NO:5) and Reverse inner 5'-GGG GGA AGA AGG GGG CAA GGC AAT-3' (SEQ ID NO:6), as well as those exemplified in Example 2;

Intron 2 C/T (rs1867973), Forward outer 5'-GCC AGG GGG TTG AGC CTC TTA T-3' (SEQ ID NO:7), Reverse outer 5'-CAG GTC CAC TTC TGA CCC TC-3' (SEQ ID NO:8), Forward inner 5'-GAA GCC TTA CAG CGA CCC GGT-3' (SEQ ID NO:9) and Reverse inner 5'-GAC CTG CCC CAG GTT TTT GG-3'(SEQ ID NO:10), as well as those exemplified in Example 2.

Within that region is the coding region of the EN2 gene. One or more single nucleotide polymorphisms (SNPs) in the EN2 gene are a preferred indicator of a predisposition to autism. Such SNPs may occur anywhere in the EN2 gene as defined above. Alternatively, a deletion in the coding region would affect the sequence of the expressed protein. A deletion in the 5' or 3' noncoding region would affect expression levels or RNA stability. A deletion 5' or 3' of the exons that encode EN2 mRNA would affect expression levels by perturbing the promoter or enhancers. Any of these deletions may have an impact on the expression product of the EN2 gene and consequently cause predisposition to autism.

Any deleted segment of one or more bases in size is diagnostically significant. Accordingly, a deletion of a single nucleotide is diagnostically significant, in particular this or any deletion that changes the function, activity, or expression levels of the EN2 protein. The deletion can be as large as a deletion of the entire en2 gene, or any portion of it.

In a fifth aspect, this invention comprises other changes (meaning in general mutations, but including any possible difference in the sequence of the gene from the wild-type) in the en2 gene as defined above. In addition to deletions as discussed above, these changes may involve additions or substitutions (by which is meant replacement of a given nucleotide or amino acid by another nucleotide or amino acid). The size or extent of the addition or substitution may be one nucleotide, to any size or extent which changes or alters EN2 expression as described above. Any one, two, or three of these changes, or mutations, may occur in one individual. Particular changes, or mutations, of interest are those that alter the function, activity, or expression levels of the EN2 protein. These additions or substitutions may be in the coding region, and thus would affect the expressed EN2 protein as described immediately below. The additions or substitutions may also be in the 5' or 3' noncoding region, in the introns, and accordingly would affect protein expression equivalently to the effect of deletions in these regions as described immediately above. Additions or substitutions in the areas spanned by the sequence pairs provided above are particularly of interest. Accordingly, part of this invention is a diagnostic method for determining that a person has a genetic abnormality that predisposes that person to autism said method comprising detecting, in that person, the existence of an addition or deletion of at least one nucleotide to a segment of the genome, that segment located within the portion of chromosome 7 as set forth is SEQ ID NO:1, or comprising detecting, in that person, the existence of a substitution of at least one nucleotide for another nucleotide in a segment of the genome, that segment located within the portion of chromosome 7 as set forth in SEQ ID NO:1. Such changes (i.e., deletions, additions, or substitutions) affect EN2 function, since they occur in some segment of the en2 gene.

Further, of particular interest are diagnostic methods where the changes (deletions, additions, or substitutions) are detected within the portion of chromosome 7, in an intron, or in a segment of an en2 gene, defined by the sequences selected from the group consisting of SEQ ID NOs:3, 4, 5, 6, 7, 8, 9, and 10, as well as those exemplified in Example 2.

In an alternative aspect, the invention comprises detecting a mutation in an exon, in any chromosome region or segment specified above providing the mutation results in a change in an amino acid in the protein coded for. Thus, the invention comprises detecting the existence of a mutation in the en2 gene such that the mutation results in the deletion, addition, or substitution of at least one amino acid in the EN2 protein.

In a related aspect, the invention comprises detecting deletions or mutations in the proteins coded for by the segments specified above, especially the EN2 protein (SEQ ID NO:2). Thus, the invention comprises detecting a change with respect to at least one amino acid in, for example, the EN2 protein, which change can be one or more additions, deletions, or substitutions, or a combination thereof (the protein in question maintains its identity by virtue of being encoded by the locus which encodes that protein, for example even if there are multiple changes in the EN2 protein, it is still considered the EN2 protein in the context of this invention as it is encoded by the en2 gene).

In a sixth aspect, the invention provides for a diagnostic method for determining a subject's susceptibility to autism or a related disorder, comprising measuring the presence or absence of the A allele of intron A/G and/or the presence or absence of the C allele of intron C/T.

In a seventh aspect, the invention provides for a diagnostic method comprising detecting, in tissue or cells from a person, an increase in the level of RNA (mRNA and/or hnRNA) transcribed from a region of SEQ ID NO:1, for example those segments specified by the sequences set forth above. In another aspect the diagnostic method comprises detecting abnormal RNA, which means RNA that is longer than normal RNA (i.e., has at least one addition), shorter than normal RNA (i.e., has at least one deletion), or is different than normal RNA (i.e., has at least one substitution, or has an equal number of deletions and additions).

One embodiment provides methods for diagnosing autism and/or Asperger's disorder and/or PDD and clinically related conditions. One embodiment includes the use of the genes or gene products identified by the methods described herein, including but not limited to those genes and gene products identified through use of a mammalian model of autism. In a particular embodiment, the gene useful for diagnosis of autism, Asperger's or PDD and other clinically related conditions includes the gene identified in the nucleic acid of SEQ ID NO:1 (EN2).

Another particular embodiment includes the use of the gene products, in particular, the protein identified by the methods described herein, including but not limited to the gene product identified as the protein of SEQ ID NO:2.

A further aspect of the invention provides a method of determining if a subject is at risk for developing autism and/or Asperger's and/or PDD, said method comprising:

(i) measuring an amount of an EN2 gene or gene product in a tissue sample derived from the subject, wherein said gene or gene product is:

(a) a DNA corresponding to SEQ ID NO:1, or a nucleic acid derived therefrom;

(b) a protein comprising SEQ ID NO:2;

(c) a nucleic acid comprising a sequence hybridizable to SEQ ID NO:1, or its complement under conditions of high stringency, or a protein comprising a sequence encoded by said hybridizable sequence;

(d) a nucleic acid at least 90% homologous to SEQ ID NO:1, or its complement as determined using the NBLAST algorithm; or a protein encoded thereby; and (ii) comparing the amount of said gene product in the subject with the amount of gene product present in a normal tissue sample (taken from a non-autistic individual) or predetermined standard for a normal tissue sample, and (iii) diagnosing risk for developing autism and/or Asperger's and/or PDD, wherein an elevated amount of said gene product in the subject compared to the amount in the normal tissue sample or pre-determined standard for a normal tissue sample indicates a risk of developing autism and/or Asperger's and/or PDD in the subject.

A further aspect of the invention provides methods for screening, diagnosis or prognosis of autism spectrum disorder, including identifying subjects with a predisposition for developing an autism spectrum disorder and those most likely to response to treatment for an autism spectrum disorder such as autism and/or Asperger's and/or PDD, said methods comprising:

(i) obtaining a sample from a human subject, said sample comprising the ENGRAILED 2 intronic sequence of SEQ ID NO:11;

(ii) detecting in said intronic sequence the presence of at least one single nucleotide polymorphism; and (iii) comparing the presence of the polymorphism with the ENGRAILED 2 intronic sequence of a non-autistic sample or predetermined standard for a non-autistic sample, and (iv) diagnosing autism, Asperger's or PDD or a predisposition of the same and the likelihood of a response to treatment for an autism spectrum disorder, wherein the presence of the at least one single nucleotide polymorphism identifies said subject being predisposed to an autism spectrum disorder and as most likely to respond to treatment for an autism spectrum disorder. In certain embodiments, the method further includes the step of administering a treatment for autism spectrum disorder such as autism and/or Asperger's and/or PDD.

In another embodiment, the diagnostic method comprises detecting, in tissue or cells from a person, an increase or a decrease in the level of normal EN2 protein, for example, protein coded for a by region of chromosome 7 set forth as SEQ ID NO:1, in particular a segment, or region specified above, for example those segments specified by the sequences set forth above. By normal protein is meant a protein which does not have an addition, deletion, or substitution, a wild-type protein, in particular an EN2 protein. Thus, in another aspect the diagnostic method comprises detecting abnormal protein, which means a protein that is longer than the normal protein (i.e., has at least one addition), shorter than the normal protein (i.e., has at least one deletion), or different than the normal protein (i.e., has at least one substitution, or has an equal number of deletions and additions).

Overexpression of EN2 protein may also indicate autism or predisposition to autism. Accordingly, in yet another aspect, the diagnostic method comprises detecting, in tissues or cells from a person, an increased level of normal RNA transcribed from a region of chromosome 7 set forth is SEQ ID NO:1, in particular a segment, or region, for example those segments specified by the sequences set forth above.

In a related protein-based assay, the diagnostic method comprises detecting, in tissue or cells from a person, an increased level of normal EN2 protein, for example, protein coded for a by a region of chromosome 7 set forth in SEQ ID NO:1, in particular a segment, or region, for example, those segments specified by the sequences set forth above.

By increased or decreased levels of RNA or protein is meant levels that differ from levels found in a normal person with no predisposition to autism. Accordingly, the normal level of RNA or protein may be determined by measuring RNA or protein levels from a sufficiently large sample of the normal population (about N=100 or greater). Since there will be a certain amount of variability, conventional statistical analysis may be used to establish a mean for the normal level of RNA or protein. An increased level of RNA or protein is a level which is significantly higher than the mean normal level by statistical analysis. A decreased level of RNA or protein is a level which is significantly lower than the mean normal level by statistical analysis. For example, a level of 10% higher or lower than normal may be considered an increased or decreased level of RNA or protein. Upon comparing the level of EN2 RNA or protein from a test subject to the levels found in a normal person with no predisposition to autism, a diagnosis or prognosis of autism, Asperger's or PDD can be made when increased EN2 RNA or protein levels are observed for the test subject.

In an eighth aspect, the invention provides for a diagnostic kit, comprising a nucleic acid hybridization probe specific for part or all of a region of the gene encoding en2, or a segment thereof. Alternatively, the kit comprises PCR primers that can be used to amplify part of a chromosome that falls within a region so specified (e.g., chromosome 7). In particular, such kits contain the PCR primers specified above, suitably paired. In another embodiment, the kit is a protein-based kit comprising an antibody probe specific for all or part of the EN2 protein.

In a ninth aspect, the invention extends to an antibody that recognizes and binds to the amino acid sequence of SEQ ID NO:2, encoded by the normal EN2 nucleic acid sequence and/or the nucleic acid sequence of SEQ ID NO:1, which contains the A allele of intron A/G located at position 154556629 and/or the C allele of intron C/T located at position 154556781 of chromosome 7, conservative variants thereof, fragments thereof, or analogs or derivatives thereof, as an immunogen. Such an antibody can be polyclonal, monoclonal, single chain, or chimeric. They may be human, mouse, rat, rabbit, goat, horse, sheep or may be obtained from other non-human animals. Further, an antibody of the invention having human EN2 as an immunogen can be detectably labelled. As explained above, examples of detectable labels having applications herein include, but certainly are not limited to radioactive isotopes, such as 3H, 14C, 32P, 35S, 36Cl, 51Cr, 57Co, 58Co, 59Fe, 90Y, 125I, 131I, and 186Re, to name only a few. Chemicals which fluoresce, or enzymes such as alkaline phosphatase or horseradish peroxidase, can also be used as detectable labels. These antibodies may be utilized for diagnostic or therapeutic purposes. In particular embodiments, the antibody is an antagonistic antibody that neutralizes or antagonizes the activity of EN2 protein.

In a tenth aspect, the invention provides for a method of treating a subject with autism or an autism related disorder such as Asperger's or PDD, or a person predisposed to a developmental disorder (especially autism), the method comprising either administering a gene or a protein to the person. In one embodiment, the method of treating a subject comprises the step of introducing a DNA molecule coding for a polypeptide normally coded for (e.g., in non-autistic patients) by a gene located within the chromosome 7 region set forth is SEQ ID NO:1. In one embodiment, the polypeptide is the EN2 protein. In another embodiment, the disorder is autism.

In certain embodiments, the DNA molecule is introduced into a cell and the cell is administered to the person (postnatal or prenatal). The cell may, for example, be a stem cell. The stem cell into which a DNA molecule is introduced for therapeutic purposes is preferably a stem cell isolated from the person who will receive the stem cell containing the DNA molecule encoding the EN2 protein. The stem cell can, for example, be obtained from that person's bone marrow. Alternatively, the stem cell can be obtained from another person. An additional alternative is that the stem cell be obtained from an animal, especially a mammal.

In another embodiment, the therapeutic process comprises the step of introducing the EN2 protein into a person.

In another embodiment, the therapeutic process comprises the step of administering a drug to a person so as to normalize (i.e., decrease to normal levels) the level of EN2 protein in a tissue in said person.

In another embodiment, the therapeutic process comprises the step of administering a drug so as to normalize (i.e., increase or decrease to normal levels) the level of genes that are activated by EN2 protein.

Any of these therapeutic processes may be used in particular to treat autism or a predisposition to autism or an autism related disorder such as Asperger's or PDD.

An eleventh aspect of the present invention provides pharmaceutical compositions comprising a therapeutically effective amount of the genes or gene products of the present invention including, but not limited to, the nucleic acid of SEQ ID NO:1 or the protein of SEQ ID NO:2, with a pharmaceutically acceptable carrier for delivery to an individual in need of such therapy. Included in this aspect of the invention are agonists or antagonists of the gene or gene products identified herein. Such agonists or antagonists may be small synthetic organic molecules, proteins, peptides, polypeptides or antibodies. A further embodiment comprises a therapeutically effective amount of an agent that modulates the expression and/or activity of the EN2 gene or gene product and a pharmaceutically acceptable carrier. The pharmaceutical compositions may be delivered orally, intravenously, intramuscularly, subcutaneously, intrathecally, intracranially. They may be in the form of tablets, capsules, suspensions, suppositories or in liquid form suitable for intravenous delivery. Other objects and advantages will become apparent from a review of the ensuing detailed description and attendant claims. All references cited in the present application are incorporated herein in their entirety.

DETAILED DESCRIPTION OF THE INVENTION

As will be appreciated by one of skill in the art, the present invention is not to be limited to particular methods, and experimental conditions described, as such methods and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The terms used herein have the meanings recognized and known to those of skill in the art, however, for convenience and completeness, particular terms and their meanings are set forth below.

"Treatment" refers to the administration of medicine or the performance of medical procedures with respect to a patient, for either prophylaxis (prevention) or to cure the infirmity or malady in the instance where the patient is afflicted.

A "therapeutically effective amount" is an amount sufficient to decrease or prevent the symptoms associated with autism associated with the presence of at least one of the SNPs identified in the presence invention.

The term "antibody" as used herein includes intact molecules as well as fragments thereof, such as Fab and F(ab')2, which are capable of binding the epitopic determinant. Antibodies that bind EN2 can be prepared using intact polypeptides or fragments containing small peptides of interest as the immunizing antigen attached to a carrier molecule. Commonly used carriers that are chemically coupled to peptides include bovine serum albumin and thyroglobulin. The coupled peptide is then used to immunize the animal (e.g., a mouse, rat or rabbit).

"Gene Product" as used herein, unless otherwise indicated, is a protein or polypeptide encoded by the nucleic acid sequences identified by the methods of the present invention, including but not limited to SEQ ID NO:1; a nucleic acid comprising a sequence hybridizable to SEQ ID NO:1 or its complement under conditions of high stringency, or a protein comprising a sequence encoded by said hybridizable sequence; a nucleic acid at least 90% homologous to SEQ ID NO:1 or its complement as determined using the NBLAST algorithm; a nucleic acid at least 90% homologous to SEQ ID NO:1 or a fragment or derivative of any of the foregoing proteins or nucleic acids.

A "variant" (v) of polynucleotides or polypeptides, as the term is used herein, are polynucleotides or polypeptides that are different from a reference polynucleotide or polypeptide, respectively. Variant polynucleotides are generally limited so that the nucleotide sequence of the reference and the variant are closely related overall and, in many regions, identical. Changes in the nucleotide sequence of the variant may be silent. That is, they may not alter the amino acid sequence encoded by the polynucleotide. Where alterations are limited to silent changes of this type a variant will encode a polypeptide with the same amino acid sequence as the reference. However, silent variants can affect protein levels by codon use. Thus, in this particular situation, different tRNAs may vary in abundance so that even though the change is silent, it may still be functionally important. Alternatively, changes in the nucleotide sequence of the variant may alter the amino acid sequence of a polypeptide encoded by the reference polynucleotide. Such nucleotide changes may result in amino acid substitutions, additions, deletions, fusions, and truncations in the polypeptide encoded by the reference sequence. Variant polypeptides are generally limited so that the sequences of the reference and the variant are that are closely similar overall and, in many regions, identical. For example, a variant and reference polypeptide may differ in amino acid sequence by one or more substitutions, additions, deletions, fusions, and truncations, which may be present or absent in any combination. Such variants can differ in their amino acid composition (e.g., as a result of allelic or natural variation in the amino acid sequence, e.g., as a result of alternative mRNA or pre-mRNA processing, e.g. alternative splicing or limited proteolysis) and in addition, or in the alternative, may arise from differential post-translational modification (e.g., glycosylation, acylation, phosphorylation, isoprenylation, lipidation).

"Analog" as used herein, refers to a nucleotide, a protein, or a polypeptide that possesses similar or identical activity or function(s) as the nucleotide, protein or polypeptide having the desired activity and therapeutic effect of the present invention (e.g., diagnostic method for determining the predisposition, the onset or the presence of autism spectrum disorder in a mammal), but need not necessarily comprise a sequence that is similar or identical to the sequence of the preferred embodiment, such as that of SEQ ID NOs: 1 and 2, or possess a structure that is similar or identical to that of SEQ ID NOs: 1 and 2. As used herein, a nucleic acid or nucleotide sequence, or an amino acid sequence of a protein or polypeptide is "similar" to that of a nucleic acid, nucleotide or protein or polypeptide having the desired activity if it satisfies at least one of the following criteria: (a) the nucleic acid, nucleotide, protein or polypeptide has a sequence that is at least 30% (more preferably, at least 35%, at least 40%, at least 45%, at least 50%, at least 55%, at least 60%, at least 65%, at least 70%, at least 75%, at least 80%, at least 85%, at least 90%, at least 95% or at least 99%) identical to the nucleic acid, nucleotide, protein or polypeptide sequences having the desired activity as described herein (b) the polypeptide is encoded by a nucleotide sequence that hybridizes under stringent conditions to a nucleotide sequence encoding at least 5 amino acid residues (more preferably, at least 10 amino acid residues, at least 15 amino acid residues, at least 20 amino acid residues, at least 25 amino acid residues, at least 40 amino acid residues, at least 50 amino acid residues, at least 60 amino acid residues, at least 70 amino acid residues, at least 80 amino acid residues, at least 90 amino acid residues, at least 100 amino acid residues, at least 125 amino acid residues, or at least 150 amino acid residues) of the AAPI; or (c) the polypeptide is encoded by a nucleotide sequence that is at least 30% (more preferably, at least 35%, at least 40%, at least 45%, at least 50%, at least 55%, at least 60%, at least 65%, at least 70%, at least 75%, at least 80%, at least 85%, at least 90%, at least 95% or at least 99%) identical to the nucleotide sequence encoding the polypeptides of the present invention having the desired therapeutic effect. As used herein, a polypeptide with "similar structure" to that of the preferred embodiments of the invention refers to a polypeptide that has a similar secondary, tertiary or quarternary structure as that of the preferred embodiment (e.g., SEQ ID NO:2). The structure of a polypeptide can determined by methods known to those skilled in the art, including but not limited to, X-ray crystallography, nuclear magnetic resonance, and crystallographic electron microscopy.

"Derivative" refers to either a protein or polypeptide that comprises an amino acid sequence of a parent protein or polypeptide that has been altered by the introduction of amino acid residue substitutions, deletions or additions, or a nucleic acid or nucleotide that has been modified by either introduction of nucleotide substitutions or deletions, additions or mutations. The derivative nucleic acid, nucleotide, protein or polypeptide possesses a similar or identical function as the parent polypeptide.

"Fragment" refers to either a protein or polypeptide comprising an amino acid sequence of at least 5 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues) of the amino acid sequence of a parent protein or polypeptide, or a nucleic acid comprising a nucleotide sequence of at least 10 base pairs (preferably at least 20 base pairs, at least 30 base pairs, at least 40 base pairs, at least 50 base pairs, at least 50 base pairs, at least 100 base pairs, at least 200 base pairs) of the nucleotide sequence of the parent nucleic acid. Any given fragment may or may not possess a functional activity of the parent nucleic acid or protein or polypeptide.

"Modulate" as used herein, refers to a compound or agent (including but not limited to proteins, polypeptides, or fragments thereof, nucleotides, nucleic acid fragments, synthetic organic compounds, antibodies) which are capable of increasing or decreasing the level and/or activity of a gene or gene product identified by the methods described herein, said genes or gene products having a beneficial effect in treating autism and/or Asperger's and/or PDD. Those skilled in the art, based on the present description, will understand that such modulation can be determined by assays and techniques known to those of skill in the art, including as described in more detail herein.

"Diagnosis" refers to diagnosis, prognosis, monitoring, characterizing, selecting patients, including participants in clinical trials, and identifying patients at risk for or having a particular disorder or clinical event or those most likely to respond to a particular therapeutic treatment, or for assessing or monitoring a patient's response to a particular therapeutic treatment.

As used herein, "detecting a target nucleic acid sequence" refers to determining the presence of a particular target nucleic acid sequence in a sample or determining the amount of a particular target nucleic acid sequence in a sample as an indication of the presence of a target nucleic acid sequence in a sample. The amount of a target nucleic acid sequence that can be measured or detected is preferably about 1 molecule to 1020 molecules, more preferably about 100 molecules to 1017 molecules and most preferably about 1000 molecules to 1014 molecules. Preferably there is a direct correlation between the amount of the target nucleic acid sequence and the signal generated by the detected nucleic acid.

As used herein, an "oligonucleotide primer" refers to a single stranded DNA or RNA molecule that is hybridizable (e.g., capable of annealing) to a nucleic acid template and is capable of priming enzymatic synthesis of a second nucleic acid strand. Alternatively, or in addition, oligonucleotide primers, when labeled directly or indirectly (e.g., bound by a labeled secondary probe which is specific for the oligonucleotide primer) may be used effectively as probes to detect the presence of a specific nucleic acid in a sample. Oligonucleotide primers useful according to the invention are between about 10 to 100 nucleotides in length, preferably about 17-50 nucleotides in length and more preferably about 17-40 nucleotides in length and more preferably about 17-30 nucleotides in length. Oligonucleotide probes useful for the formation of a cleavage structure according to the invention are between about 17-40 nucleotides in length, preferably about 17-30 nucleotides in length and more preferably about 17-25 nucleotides in length. The term "primer" can refer to more than one primer and generally refers to an oligonucleotide, whether occurring naturally, as in a purified restriction digest, or produced synthetically, which is capable of acting as a point of initiation of DNA synthesis when annealed to a nucleic acid template and placed under conditions in which synthesis of a primer extension product which is complementary to the template is catalyzed. Such conditions include the presence of four different deoxyribonucleoside triphosphates and a polymerization-inducing agent such as a DNA polymerase or reverse transcriptase, in a suitable buffer ("buffer" includes substituents which are cofactors, or which affect pH, ionic strength, etc.), and at a suitable temperature. The primer is preferably single-stranded for maximum efficiency in amplification.

As used herein, "amplifying" refers to the generation of additional copies of a nucleic acid sequence. A variety of methods have been developed to amplify nucleic acid sequences, including the polymerase chain reaction (PCR). PCR amplification of a nucleic acid sequence generally results in the exponential amplification of a nucleic acid sequence(s) and or fragments thereof. An "amplified" nucleic acid molecule (or portion thereof) refers to the fact that multiple copies of that molecule or a molecule of complementary base sequence have been made.

By "homologous" is meant a same sense nucleic acid which possesses a level of similarity with the target nucleic acid within reason and within standards known and accepted in the art. With regard to PCR, the term "homologous" may be used to refer to an amplicon that exhibits a high level of nucleic acid similarity to another nucleic acid, e.g., the template cDNA. As is understood in the art, enzymatic transcription has measurable and well known error rates (depending on the specific enzyme used), thus within the limits of transcriptional accuracy using the modes described herein, in that a skilled practitioner would understand that fidelity of enzymatic complementary strand synthesis is not absolute and that the amplified nucleic acid (i.e., amplicon) need not be completely identical in every nucleotide to the template nucleic acid.

"Complementary" is understood in its recognized meaning as identifying a nucleotide in one sequence that hybridizes (anneals) to a nucleotide in another sequence according to the rule A->T/U and C->G (and vice versa) and thus "matches" its partner for purposes of this definition. Enzymatic transcription has measurable and well known error rates (depending on the specific enzyme used), thus within the limits of transcriptional accuracy using the modes described herein, in that a skilled practitioner would understand that fidelity of enzymatic complementary strand synthesis is not absolute and that the amplicon need not be completely matched in every nucleotide to the target or template RNA.

As used herein, the terms "nucleic acid", "polynucleotide" and "oligonucleotide" refer to primers, probes, and oligomer fragments to be detected, and shall be generic to polydeoxyribonucleotides (containing 2-deoxy-D-ribose), to polyribonucleotides (containing D-ribose), and to any other type of polynucleotide which is an N-glycoside of a purine or pyrimidine base, or modified purine or pyrimidine bases (including abasic sites). There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single-stranded RNA.

The "polymerase chain reaction (PCR)" technique, is disclosed in U.S. Pat. Nos. 4,683,202; 4,683,195 and 4,800,159. In its simplest form, PCR is an in vitro method for the enzymatic synthesis of specific DNA sequences, using two oligonucleotide primers that hybridize to opposite strands and flank the region of interest in the target DNA. A repetitive series of reaction steps involving template denaturation, primer annealing and the extension of the annealed primers by DNA polymerase results in the exponential accumulation of a specific fragment (i.e., an amplicon) whose termini are defined by the 5' ends of the primers. PCR is reported to be capable of producing a selective enrichment of a specific DNA sequence by a factor of 109. The PCR method is also described in Saiki, et al. ((1985) Science 230:1350).

As used herein, "probe" refers to a labeled oligonucleotide primer, which forms a duplex structure with a sequence in the target nucleic acid, due to complementarity of at least one sequence in the probe with a sequence in the target region. Such probes are useful for identification of a target nucleic acid sequence for EN2 according to the invention. Pairs of single-stranded DNA primers can be annealed to sequences within a target nucleic acid sequence or can be used to prime DNA synthesis of a target nucleic acid sequence.

By "genetic abnormality" is meant any change in a nucleic acid sequence which may predispose a person to autism, or Asperger's or PDD. The change is determined using standard techniques in the art and a comparison is made to a known sequence obtained from a normal individual known to be free of autism, Asperger's or PDD. Such changes may include mutations and may be deletions, additions or substitutions in at least one base pair of the sequence.

"kD" stands for kilodalton.

Code-wise degenerate means that a base of a codon is changed without changing the amino acid that the codon codes for.

A "coding sequence" or a "coding region" of a nucleic acid for a designated protein refers to a region in an mRNA molecule that contains the base sequence which is translated into an amino acid sequence (i.e., that encodes that amino acid sequence), it covers any DNA or RNA sequence that is complementary in base sequence to such an mRNA sequence, it covers any DNA sequence that is the same as such an mRNA sequence (except that T is used in place of U) and, in the case of a DNA sequence that alternates introns with exons so that the sequence can be processed to make an mRNA molecule, "coding sequence" or "coding region" covers the populations of coding exons that determine the amino acid coding region of the mRNA molecule (i.e., that encode that amino acid sequence).

By way of example and not limitation, procedures using such conditions of low stringency are as follows (see also Shilo and Weinberg (1981) Proc. Natl. Acad. Sci. USA 78:6789-6792). Filters containing DNA are pretreated for 6 hours at 40° C. in a solution containing 35% formamide, 5×SSC, 50 mM Tris-HCl (pH 7.5), 5 mM EDTA, 0.1% polyvinylpyrrolidone (PVP), 0.1% Ficoll™, 1% bovine serum albumin (BSA), and 500 µg/ml denatured salmon sperm DNA. Hybridizations are carried out in the same solution with the following modifications: 0.02% PVP, 0.02% Ficoll™, 0.2% BSA, 100 μg/ml salmon sperm DNA, 10% (wt/vol) dextran sulfate, and 5-20×106 cpm 32P-labeled probe is used. Filters are incubated in hybridization mixture for 18-20 hours at 40° C., and then washed for 1.5 hours at 55° C. in a solution containing 2×SSC, 25 mM Tris-HCl (pH 7.4), 5 mM EDTA, and 0.1% SDS. The wash solution is replaced with fresh solution and incubated an additional 1.5 hours at 60° C. Filters are blotted dry and exposed for autoradiography. If necessary, filters are washed for a third time at 65-68° C. and re-exposed to film. Other conditions of low stringency that may be used are well-known in the art (e.g., as employed for cross-species hybridizations).

Procedures using such conditions of moderate stringency are as follows: filters comprising immobilized DNA are pretreated for 6 hours at 55° C. in a solution containing 6×SSC, 5×Denhardt's solution, 0.5% SDS and 100 μg/ml denatured salmon sperm DNA. Hybridizations are carried out in the same solution with 5-20×106 cpm 32P-labeled probe. Filters are incubated in hybridization mixture for 18-20 hours at 55° C., and then washed twice for 30 minutes at 60° C. in a solution containing 1×SSC and 0.1% SDS. Filters are blotted dry and exposed for autoradiography. Washing of filters is done at 37° C. for 1 hour in a solution containing 2×SSC, 0.1% SDS. Other conditions of moderate stringency that may be used are well-known in the art. See, e.g., Sambrook et al. (1989) *Molecular Cloning: A Laboratory Manual,* 2d Ed., Cold Spring Harbor Laboratory Press, Cold Spring Harbor, N.Y.; Ausubel et al., eds., in the *Current Protocols in Molecular Biology* series of laboratory technique manuals, 1987-1997 *Current Protocols,*© 1994-1997 John Wiley and Sons, Inc.

Procedures using such conditions of high stringency are as follows. Prehybridization of filters containing DNA is carried out for 8 hours to overnight at 65° C. in buffer composed of 6×SSC, 50 mM Tris-HCl (pH 7.5), 1 mM EDTA, 0.02% PVP, 0.02% Ficoll™, 0.02% BSA, and 500 μg/ml denatured salmon sperm DNA. Filters are hybridized for 48 hours at 65° C. in prehybridization mixture containing 100 μg/ml denatured salmon sperm DNA and 5-20×106 cpm of 32P-labeled probe. Washing of filters is done at 37° C. for 1 hour in a solution containing 2×SSC, 0.01% PVP, 0.01% Ficoll™, and 0.01% BSA. This is followed by a wash in 0.1×SSC at 50° C. for 45 minutes before autoradiography. Other conditions of high stringency that may be used are well-known in the art.

An RNA base sequence (or molecule) is equivalent to a DNA base sequence (or molecule) if they are identical except that U in the RNA base sequence replaced T in the DNA base sequence.

The following one letter codes are used to represent amino acids: S—serine, T—threonine, N—asparagine, Q—glutamine, K—lysine, R—arginine, H—histidine, E—glutamic acid, D—aspartic acid, C—cystine, G—glycine, P—proline, A—alanine, I—isoleucine, L—leucine, M—methionine, F—phenylalanine, W—tryptophan, V—valine, Y—tyrosine, X—any amino acid.

The following one letter codes are used to represent nucleic acids: A—adenine, C—cytosine, G—guanine, T-thymidine, R represents A or G, Y represents T or C, N represents any nucleic acid.

An EN2 nucleic acid or protein referred to herein is a human one unless otherwise noted.

A chromosome region is spanned by two sequences if one sequence is at one end of the region and the other sequence is at the other end of the region.

An EN2 protein includes any protein or fragment encoded by the EN2 gene, including any segment, region, or exon.

Autism and allied autistic spectrum (AS) disorders present with a myriad of behavioral, clinical, and biochemical abnormalities. Several studies have demonstrated that AS has a genetic basis. Family studies have determined that there is a 75-fold greater chance of siblings inheriting the disorder than the general population if a brother or sister already has autism (Bolton, et al. (1994) *J. Child Psychol. Psychiat.* 35:877-900). Monozygotic twin studies display a 75% concordance in symptoms in comparison to only 10% in fraternal twins (Bailey, et al. (1998) *Brain* 121:889-905; Folstein and Rutter (1977) *J. Child Psychol. Psychiat.* 18:297-321; Ritvo, et al. (1985) *Am. J. Psychiat.* 142:74-77). This large difference suggests that multiple loci are involved, with some models predicting more than 15 genes contributing to the disorder (Folstein and Rosen-Sheidley (2001) *Nat. Rev. Genet.* 2:943-955; Lamb, et al. (2000) *Hum. Mol. Genet.* 9:861-868; Risch, et al. (1999) *Am. J. Hum. Genet.* 65:493-507).

Furthermore, the cerebellum is most often malformed in autistic individuals. 21/22 autopsy studies have revealed cerebellar abnormalities including Purkinje cell loss. These defects occur in the absence of any obvious sign of degeneration suggesting that autism is instead caused by developmental defects (Bailey, et al. (1998) *Brain* 121:889-905; Bauman and Kemper (1985) *Neurology* 35: 866-874; Bauman and Kemper (1986) *Neurology* 36(suppl. 1):190; Bauman and Kemper (1994) In *The Neurobiology of Autism.* Baltimore: John Hopkins University Press pp 119-145; Courchesne (1997) *Learn Mem.* 4:1-35; Kemper and Bauman (1993) *Behav. Neuro.* 11:175-187; Ritvo, et al. (1996) *Am. J. Psychiatry* 143:862-866). In addition, imaging studies have also demonstrated cerebellar hypoplasia (Courchesne, et al. (1988) *New Eng. J. Med.* 318:1349-1354; Courchesne (1997) *Curr. Opin. Neurobiol.* 7:269-278; Gaffney, et al. (1987) *Br. J. Psychiatry* 151:831-833; Hashimoto, et al. (1995) *J. Autism Dev. Discord.* 25:1-18; Kleiman, et al. (1992) *Neurology* 42:753-760; Murakami, et al. (1989) *Arch. Neurol.* 46:689-694). A recent imaging report has uncovered abnormal cerebellar growth patterns after birth. The growth is initially accelerated followed by a decrease after age six (Courchesne, et al. (2001) *Neurology* 57:245-254). These studies indicate that cerebellar development is perturbed in autism. Interestingly, recent fMRI studies indicate that the cerebellum is active during tasks that are defective in autism including language and attention (Akshoomoff, et al. (1997) *Int. Rev. Neurobiol.* 41:575-98; Allen, et al. (1997) *Science* 275:1940-1943; Allen and Courchesne (2003) *Am. J. Psychiatry* 160:262-73; Courchesne, et al. (1994) *Behavioral Neuroscience* 108:848-865; Courchesne and Allen (1997) *Learn Mem.* 4:1-35; Gao, et al. (1996) *Science* 272:545-547). Thus, these anatomical defects might directly contribute to the behavioral abnormalities associated with autism.

Mouse genetics have identified a large number of genes that function during cerebellar development (Hatten and Heintz (1995) *Annu. Rev. Neurosci.* 18:385-408; Hatten, et al. (1997) *Curr. Opin. Neurobiol.* 7(1):40-47). One such gene is Engrailed2, a homeobox transcription factor that is orthologous to *Drosophila melanogaster* engrailed. In the mouse, there are two Engrailed genes, En1 and En2. Knockout studies have demonstrated that En1 functions during early A-P patterning of neural tube while En2 is specifically required for normal postnatal cerebellar development (Millen, et al. (1994) *Development* 120:695-706; Hanks, et al. (1995) *Science* 269:679-682; Millen, et al. (1995) *Development* 121:3935-45; Liu and Joyner (2001) *Annu. Rev. Neurosci.* 24:869-896). The En2−/− mutant displays cerebellar hypoplasia that is due in part to a reduction in all the major cerebellar cell types including Purkinje cells (Millen, et al. (1994) *Development* 120:695-706; Millen, et al. (1995) *Development* 121:3935-45; Kuemerle, et al. (1997) *J. Neurosci.* 17:7881-9). Human EN2 maps to distal chromosome 7, a region that displays linkage to AS in two separate studies (Liu, et al. (2001) *Annu. Rev. Neurosci.* 24:869-896; Auranen, et al. (2002) *Am. J. Hum. Genet.* 71:777-790). Thus, EN2 was tested as a susceptibility locus for AS by performing family based association analysis.

Research suggests that early diagnosis of autism or autism related disorders such as Asperger's or PDD may be associated with dramatically better outcomes. The earlier a child is diagnosed, the earlier the child may begin benefiting from one of the many specialized intervention approaches.

There is provided, in accordance with the present invention, an isolated nucleic acid molecule (SEQ ID NO:1), which encodes human EN2, and the amino acid sequence of human EN2 (SEQ ID NO:2). SEQ ID NO:1 represents both exons of the EN2 locus, the single intron, as well as 1000 bp 5' and 3' of the coding sequence. The position of EN2 on chromosome 7 is between position 154552000 and position 154560000. More particularly, there is provided, in accordance with the present invention, methods for determining a subject's susceptibility to autism or a disease or disorder related thereto, such as Asperger's Disorder or PDD using a variant allele of the Engrailed (EN2) gene, which maps to chromosome 7, in particular, to 7q36.3. Furthermore, transmission/disequilibrium tests (TDT), which were performed for two single nucleotide polymorphisms (Intron 1: A/G and Intron 2: C/T), revealed significant overtransmission of the A allele of Intron 1: A/G and the C allele of Intron 2: C/T (Intron A/G P=0.0009; Intron C/T P=0.0006). Intron 1 (rs1861972), which is located at position 154556629 of human chromosome 7, results in a guanine to adenine transition, whereas Intron 2 (rs1867973), located at position 154556781 of human chromosome 7, results in a thymine to cytosine transition. Haplotype analysis indicated that the A-C haplotype is specifically overtransmitted in autistic individuals (P=0.000062). Thus, detection of such a variant allele in the genome of a subject is indicative of the subject's susceptibility to autism. Furthermore, a variant allele of the Engrailed gene can also be used to assay drugs and agents for potential use in treating autism or a disease or disorder related thereto, such as Asperger's Disorder or PDD.

The present invention relates to the identification of particular single nucleotide polymorphisms (SNPs), which show statistical relevance in terms of being markers of susceptibility to autism and autism related disorders. In particular, the two SNPs have been found on chromosome 7, in the gene that encodes for the transcription factor EN2.

In particular, the homeobox transcription factor, ENGRAILED 2 (EN2), was investigated for association with autism spectrum disorder (AS) by performing transmission/disequilibrium tests (TDT) for two SNPs (rs1861972 and rs1861973). Initially, TDT was performed using 137 triads of autistic individuals and their parents and significant overtransmission of the A allele of rs1861972 and the C allele of rs1861973 was observed (rs1861972 P=0.0009; rs1861973 P=0.0006; A-C haplotype P=0.000062). The analysis was then extended to include other affected and unaffected siblings as well as 29 additional families. Significant association was observed for both SNPs under both the broad and narrow diagnostic schemes (rs1861972: narrow P=0.0106, broad P=0.0050; rs1861973: narrow P=0.0033, broad P=0.0063; A-C Haplotype: narrow P=0.0007, broad P=0.0009). The procedures utilized for the analyses in these studies are known to those skilled in the art (see, e.g., Martin, et al. (2000) Am. J. Hum. Genet. 67:146-154; Terwilliger, (1995) Am. J. Hum. Genet. 56:777-787; Ye, et al. (2001) Nucleic Acids Res. 29:E88-8; Clayton, (1999) Am. J. Hum. Genet. 65:1170-1177; Strachan and Read, Human Molecular Genetics 2, Wiley Liss, New York, N.Y. (1999)). In summary, these results identify EN2 as a susceptibility locus for autism and related AS disorders. Accordingly, in certain embodiments, the EN2 locus set forth as SEQ ID NO:1 is employed to determine whether a person is predisposed to autism spectrum disorder. In particular embodiments nucleic acids corresponding to the intron of the EN2 locus are employed to determine whether a person is predisposed to autism spectrum disorder. The ~3.3 kb intron of the EN2 locus is set forth herein as SEQ ID NO:11.

The characteristic behaviors of autism spectrum disorders may or may not be apparent in infancy (18 to 24 months), but usually become obvious during early childhood (24 months to 6 years). While there is no one behavioral or communications test that can detect autism, several screening instruments have been developed that are now used in diagnosing autism. CARS rating system (Childhood Autism Rating Scale), developed in the early 1970s, is based on observed behavior. Using a 15-point scale, professionals evaluate a child's relationship to people, body use, adaptation to change, listening response, and verbal communication. The Checklist for Autism in Toddlers (CHAT) is used to screen for autism at 18 months of age. It was developed in the early 1990s to see if autism could be detected in children as young as 18 months. The screening tool uses a short questionnaire with two sections, one prepared by the parents, the other by the child's family doctor or pediatrician. The Autism Screening Questionnaire is a 40-item screening scale that has been used with children four and older to help evaluate communication skills and social functioning. The Screening Test for Autism in Two-Year Olds uses direct observations to study behavioral features in children under two. Three skills areas have been identified—play, motor imitation, and joint attention—that seem to indicate autism.

The diagnostic criteria for Asperger's Disorder include 1) a qualitative impairment in social interaction, as manifested by at least two of the following: marked impairments in the use of multiple nonverbal behaviors such as eye-to-eye gaze, facial expression, body postures, and gestures to regulate social interaction; failure to develop peer relationships appropriate to developmental level; a lack of spontaneous seeking to share enjoyment, interests, or achievements with other people (e.g., by a lack of showing, bringing, or pointing out objects of interest to other people); or lack of social or emotional reciprocity, and 2) restricted repetitive and stereotyped patterns of behavior, interests, and activities, as manifested by at least one of the following: encompassing preoccupation with one or more stereotyped and restricted patterns of interest that is abnormal either in intensity or focus; apparently inflexible adherence to specific, nonfunctional routines or rituals; stereotyped and repetitive motor mannerisms (e.g., hand or finger flapping or twisting, or complex whole-body movements); or persistent preoccupation with parts of objects. Asperger's Disorder causes clinically significant impairment in social, occupational, or other important areas of functioning. There is no clinically significant general delay in language (e.g., single words used by age 2 years, communicative phrases used by age 3 years). There is no clinically significant delay in cognitive development or in the development of age-appropriate self-help skills, adaptive behavior (other than social interaction), and curiosity about the environment in childhood. Criteria are not met for another specific Pervasive Developmental Disorder or Schizophrenia.

Because a behaviour-based diagnosis of autism is difficult, especially in young patients, it is of value to have a genetic screening assay to assist in the diagnosis. Furthermore, such an assay can be used to advise potential parents of their chances of having autistic children.

However, up until the disclosure in the present invention, there has been no genetic marker available which is indicative of a subject's susceptibility to autism, or a disease related thereto, such as Asperger's Disorder or PDD.

EN2 protein for use in this invention can be isolated and purified according to techniques known in the art. The protein may be made by known methods of chemical synthesis, or expressed. The description below provides examples of materials and methods for so doing, but is not intended to be either limiting or exclusive.

Expressed proteins are generally produced using the nucleotide sequence encoding the protein (provided herein) or antigenic fragment, derivative or analog thereof, or a functionally active derivative, including a chimeric protein, thereof. The nucleotide sequence can be inserted into an appropriate expression vector, i.e., a vector which contains the necessary elements for the transcription and translation of the inserted protein-coding sequence. Such elements are termed herein a "promoter." Thus, the nucleic acid encoding the EN2 protein of the protein of the present invention is operationally associated with a promoter in an expression vector of the invention. Both cDNA and genomic sequences can be cloned and expressed under control of such regulatory sequences. An expression vector also preferably includes a replication origin.

The necessary transcriptional and translational signals can be provided on a recombinant expression vector, or they may be supplied by the native gene encoding EN2 protein and/or its flanking regions. Chimeric proteins including EN2 protein may also be produced as described.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

In this regard, any of a number of amplification systems may be used to achieve high levels of stable gene expression.

The cell containing the recombinant expression vector is cultured in an appropriate cell culture medium under conditions that provide for expression of protein by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression may be controlled by any promoter/enhancer element known in the art, but these regulatory elements must be functional in the host selected for expression. Promoters which may be used to control EN2 gene expression include, but are not limited to, the SV40 early promoter region (Benoist and Chambon (19810 Nature 290:304-310), the promoter contained in the 3' long terminal repeat of Rous sarcoma virus (Yamamoto, et al. (1980) Cell 22:787-797), the herpes thymidine kinase promoter (Wagner, et al. (1981) Proc. Natl. Acad. Sci. USA 78:1441-1445), the regulatory sequences of the metallothionein gene (Brinster, et al. (1982) Nature 296:39-42); prokaryotic expression vectors such as the β-lactamase promoter (Villa-Kamaroff, et al. (1978) Proc. Natl. Acad. Sci. USA 75:3727-3731), or the tac promoter (DeBoer, et al. (1983) Proc. Natl. Acad. Sci. USA 80:21-25); see also Scientific American (1980) 242:74-94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals, e.g., elastase I gene control region which is active in pancreatic acinar cells (Swift, et al. (1984) Cell 38:639-646; Ornitz, et al. (1986) Cold Spring Harbor Symp. Quant. Biol. 50:399-409; MacDonald (1987) Hepatology 7:425-515); insulin gene control region which is active in pancreatic beta cells (Hanahan (1985) Nature 315:115-122); immunoglobulin gene control region which is active in lymphoid cells (Grosschedl, et al. (1984) Cell 38:647-658; (Adames, et al. (1985) Nature 318:533-538; Alexander, et al. (1987) Mol. Cell. Biol. 7:1436-1444); mouse mammary tumor virus control region which is active in testicular, breast, lymphoid and mast cells (Leder, et al. (1986) Cell 45:485-495); albumin gene control region which is active in liver (Pinkert, et al. (1987) Genes Dev. 1:268-276); alpha-fetoprotein gene control region which is active in liver (Krumlauf, et al. (1985) Mol. Cell. Biol. 5:1639-1648; Hammer, et al. (1987) Science 235:53-58); alpha 1-antitrypsin gene control region which is active in the liver (Kelsey, et al. (1987) Genes Dev. 1:161-171); beta-globin gene control region which is active in myeloid cells (Mogram, et al. (1985) Nature 315:338-340; Kollias, et al. (1986) Cell 46:89-94); myelin basic protein gene control region which is active in oligodendrocyte cells in the brain (Readhead, et al. (1987) Cell 48:703-712); myosin light chain-2 gene control region which is active in skeletal muscle (Sani (1985) Nature 314:283-286), and gonadotropic releasing hormone gene control region which is active in the hypothalamus (Mason, et al. (1986) Science 234:1372-1378).

Expression vectors containing a nucleic acid encoding an EN2 protein of the invention can be identified by four well-known approaches: (a) PCR amplification of the desired plasmid DNA or specific mRNA, (b) nucleic acid hybridization, (c) presence or absence of selection marker gene functions, and (d) expression of inserted sequences.

A wide variety of host/expression vector combinations may be employed in expressing the EN2 gene or fragments of this invention. Useful expression vectors, for example, may include segments of chromosomal, non-chromosomal and synthetic DNA sequences. Suitable vectors include derivatives of SV40 and known bacterial plasmids, e.g., *E. coli* plasmids col El, pCR1, pBR322, pMal-C2, pET, pGEX (Smith, et al. (1988) *Gene* 67:31-40), pMB9 and their derivatives, plasmids such as RP4; phage DNAS, e.g., the numerous derivatives of phage, e.g., NM989, and other phage DNA, e.g., M13 and filamentous single stranded phage DNA; yeast plasmids such as the 2 μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in a baculovirus expression systems, both non-fusion transfer vectors, such as but not limited to pVL941 (Summers), pVL1393 (Invitrogen™), pVL1392 (Summers and Invitrogen™), and pBlueBacIII (Invitrogen™), and fusion transfer vectors, such as but not limited to pAc700 (Summers), pAc701 and pAc702, pAc360 (Invitrogen™), and pBlueBacHisA, B, C (Invitrogen™)

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; see Kaufman, Current Protocols in Molecular Biology, 16.12 (1991). Alternatively, a glutamine synthetase/methionine sulfoximine co-amplification vector, such as pEE14 (Celltech). In another embodiment, a vector that directs episomal expression under control of Epstein Barr Virus (EBV) can be used, such as pREP4 (Invitrogen™), pCEP4 (Invitrogen™), pMEP4 (Invitrogen™), pREP8 (Invitrogen™), pREP9 (Invitrogen™), and pEBVHis (Invitrogen™). Selectable mammalian expression vectors for use in the invention include pRc/CMV (Invitrogen™), pRc/RSV (Invitrogen™), and others. Vaccinia virus mammalian expression vectors (see, Kaufman (1991) supra) for use according to the invention include but are not limited to pSC11 and pMJ601.

Yeast expression systems can also be used according to the invention. For example, the non-fusion pYEN2 vector (Invitrogen™) or the fusion pYESHisA, B, C (Invitrogen™), to mention just two, can be employed according to the invention.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Different host cells have characteristic and specific mechanisms for the translational and post-translational processing and modification (e.g., glycosylation, cleavage of signal sequence) of proteins. Appropriate cell lines or host systems can be chosen to ensure the desired modification and processing of the foreign protein expressed. For example, expression in a bacterial system can be used to produce a non-glycosylated core protein product.

Vectors are introduced into the desired host cells by methods known in the art, e.g., transfection, electroporation, micro injection, transduction, cell fusion, DEAE dextran, calcium phosphate precipitation, lipofection (lysosome fusion), use of a gene gun, or a DNA vector transporter (see, e.g., Wu, et al. (1992) J. Biol. Chem. 267:963-967; Wu and Wu (1988) J. Biol. Chem. 263:14621-14624; Canadian Patent Application No. 2,012,311).

The purification of EN2 Protein can be accomplished by any number of procedures that encompass a wide variety of known purification steps. Those with skill in the art would know to refer to references, such as the Methods of Enzymology series, for greater detail and breadth. Initial steps for purifying the proteins of the present invention include salting in or salting out, such as in ammonium sulfate fractionations; solvent exclusion fractionations, e.g., an ethanol precipitation; detergent extractions to free membrane bound proteins using such detergents as Triton™ X-100, Tween™-20 etc.; or high salt extractions. Solubilization of proteins may also be achieved using aprotic solvents such as dimethyl sulfoxide and hexamethylphosphoramide. In addition, high speed ultracentrifugation may be used either alone or in conjunction with other extraction techniques. A useful method is tagging the protein with hexa-histidine via Ni+ chromatography (Coligan, et al. (1995) Current Protocols in Protein Science, vol. 1, John Wiley and Sons, New York; Methods in Enzymology (1990) M. P. Deutscher, ed., vol. 185 Guide to Protein Purification, Academic Press, San Diego, Calif.; Crowe, et al. (1994) Methods Mol. Biol. 31:371-387; Schmitt, et al. (1993) Mol. Biol. Rep. 18:223-230).

Generally good secondary isolation or purification steps include solid phase absorption using calcium phosphate gel or hydroxyapatite, or solid phase binding. Solid phase binding may be performed through ionic bonding, with either an anion exchanger, such as diethylaminoethyl (DEAE), or diethyl [2-hydroxy propyl]amino ethyl (QAE) Sephadex® or cellulose; or with a cation exchanger such as carboxymethyl (CM) or sulfo propyl (SP) Sephadex® or cellulose. Alternative means of solid phase binding includes the exploitation of hydrophobic interactions, e.g., the using of a solid support such as phenyl-Sepharose® and a high salt buffer; affinity-binding, bound to an activated support; immuno-binding, using, e.g., an antibody to the EN2 protein bound to an activated support; as well as other solid phase supports including those that contain specific dyes or lectins etc. A further solid phase support technique that is often used at the end of the purification procedure relies on size exclusion, such as Sephadex® and Sepharose® gels, or pressurized or centrifugal membrane techniques, using size exclusion membrane filters.

Solid phase support separations are generally performed batch-wise with low-speed centrifugations or by column chromatography. High performance liquid chromatography (HPLC), including such related techniques as FPLC, is presently the most common means of performing liquid chromatography. Size exclusion techniques may also be accomplished with the aid of low speed centrifugation.

In addition size permeation techniques such as gel electrophoretic techniques may be employed. These techniques are generally performed in tubes, slabs or by capillary electrophoresis.

Almost all steps involving protein purification employ a biological buffer at a pH close to the pKa of that buffer. Typical buffers can be purchased from most biochemical catalogues and include the classical buffers such as Tris, pyrophosphate, monophosphate, and diphosphate, or the Good buffers (Good, et al. (1966) Biochemistry 5:467; Good and Izawa (1972) Meth. Enzymol. 24(Part B):53; Fergunson and Good (1980) Anal. Biochem. 104:300) such as MES, HEPES, MOPS, tricine and Ches.

Materials to perform all of these techniques are available from a variety of sources such as Sigma Chemical Company in St. Louis, Mo.

Antibodies for use in this invention can be produced according to techniques known in the art. The description below provides examples of materials and methods for so doing, but is not intended to be either limiting or exclusive.

According to the invention, EN2 protein may produced recombinantly or by chemical synthesis as described above, and fragments or other derivatives or analogs thereof, including fusion proteins, may be used as an immunogen to generate antibodies that recognize the protein. Such antibodies include, but are not limited to, polyclonal, monoclonal, chimeric, single chain, Fab fragments, and a Fab expression library. The anti-EN2 Protein antibodies of the invention may be cross-reactive, e.g., they may recognize EN2 protein from different species. Polyclonal antibodies have greater likelihood of cross-reactivity. Alternatively, an antibody of the invention may be specific for a single form of EN2 protein, such as murine EN2 protein. Preferably, such an antibody is specific for human EN2 protein.

Various procedures known in the art may be used for the production of polyclonal antibodies to EN2 protein. For the production of antibody, various host animals can be immunized by injection with the EN2 protein, including but not limited to rabbits, mice, rats, sheep, goats, etc. In one embodiment, the EN2 protein thereof can be conjugated to an immunogenic carrier, e.g., BSA or keyhole limpet hemocyanin (KLH). Various adjuvants may be used to increase the immunological response, depending on the host species, including but not limited to Freund's (complete and incomplete), mineral gels such as aluminum hydroxide, surface-active substances such as lysolecithin, Pluronic™ polyols, polyanions, peptides, oil emulsions, dinitrophenol, and potentially useful human adjuvants such as BCG (bacille Calmette-Guerin) and *Corynebacterium parvum*.

For preparation of monoclonal antibodies directed toward the EN2 protein, any technique that provides for the production of antibody molecules by continuous cell lines in culture may be used. These include, but are not limited to, the hybridoma technique originally developed by Kohler and Milstein ((1975) *Nature* 256:495-497), as well as the trioma technique, the human B-cell hybridoma technique (Kozbor, et al. (1983) *Immunol. Today* 4:72; Cote, et al. (1983) *Proc. Natl. Acad. Sci. USA* 80:2026-2030), and the EBV-hybridoma technique to produce human monoclonal antibodies (Cole, et al. (1985) In: *Monoclonal Antibodies and Cancer Therapy*, Alan R. Liss, Inc., pp. 77-96). In an additional embodiment of the invention, monoclonal antibodies can be produced in germ-free animals. In fact, according to the invention, techniques developed for the production of "chimeric antibodies" (Morrison, et al. (1984) *J. Bacteriol.* 159:870; Neuberger, et al. (1984) *Nature* 312: 604-608; Takeda, et al. (1985) *Nature* 314:452-454) by splicing the genes from a mouse antibody molecule specific for an EN2 protein together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies (U.S. Pat. Nos. 5,476, 786 and 5,132,405; U.S. Pat. No. 4,946,778) can be adapted to produce EN2 protein-specific single chain antibodies. An additional embodiment of the invention utilizes the techniques described for the construction of Fab expression libraries (Huse, et al. (1989) *Science* 246:1275-1281) to allow rapid and easy identification of monoclonal Fab fragments with the desired specificity for an EN2 protein. Antibody fragments which contain the idiotype of the antibody molecule can be generated by known techniques. For example, such fragments include but are not limited to: the F(ab')2 fragment which can be produced by pepsin digestion of the antibody molecule; the Fab' fragments which can be generated by reducing the disulfide bridges of the F(ab')2 fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an EN2 protein, one may assay generated hybridomas for a product which binds to an EN2 protein fragment containing such epitope. For selection of an antibody specific to an EN2 protein from a particular species of animal, one can select on the basis of positive binding with EN2 protein expressed by or isolated from cells of that species of animal.

The foregoing antibodies can be used in methods known in the art relating to the localization and activity of the EN2 protein, e.g., for western blot analysis, imaging EN2 protein in situ, measuring levels thereof in appropriate physiological samples, etc. using any of the detection techniques mentioned above or known in the art.

In a specific embodiment, antibodies that agonize or antagonize the activity of EN2 protein can be generated. Such antibodies can be tested using the assays described infra for identifying ligands.

In an immunoassay, a control quantity of the antagonists or antibodies thereto, or the like may be prepared and labeled with an enzyme, a specific binding partner and/or a radioactive element, and may then be introduced into a cellular sample. After the labeled material or its binding partner(s) has had an opportunity to react with sites within the sample, the resulting mass may be examined by known techniques, which may vary with the nature of the label attached.

In the instance where a radioactive label, such as the isotopes $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

The present invention includes an assay system which may be prepared in the form of a test kit for the quantitative analysis of the extent of the presence of the EN2 protein, or to identify drugs or other agents that may mimic or block its activity. Alternatively, the presence of the single nucleotide polymorphisms of the present invention can be monitored using standard techniques known in the art. The system or test kit may comprise a labeled component prepared by one of the radioactive and/or enzymatic techniques discussed herein, coupling a label to the antibody or an agonist and/or antagonist, and one or more additional immunochemical reagents, at least one of which is a free or immobilized ligand, capable either of binding with the labeled component, its binding partner, one of the components to be determined or their binding partner(s).

In the context of treatment, administration of cells, genes, and proteins to a person can be carried by a variety of methods. For example, in gene therapy, the EN2 gene or appropriate fragments of the gene (for example corresponding to a deleted region in an individual patient) can be used in methods known in the art. In such methods, the gene is introduced in vivo in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Examples of particular vectors include, but are not limited to, a defective herpes virus 1 (HSV1) vector (Kaplitt, et al. (1991) *Mol. Cell. Neurosci.* 2:320-330), an attenuated adenovirus vector (Stratford-Perricaudet, et al. (1992) *J. Clin. Invest.* 90:626-630), and a defective adeno-associated virus vector (Samulski, et al. (1987) *J. Virol.* 61:3096-3101; Samulski, et al. (1989) *J. Virol.* 63:3822-3828).

Preferably, for in vitro administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12, interferon, or anti-CD4 antibody, can be administered to block humoral or cellular immune responses to the viral vectors (see, e.g., Yang, et al. (1995) *Nat. Med.* 1(9):890-3). In addition, it is advantageous to employ a viral vector that is engineered to express a minimal number of antigens.

In another embodiment the gene can be introduced in a retroviral vector, e.g., as described in U.S. Pat. No. 5,399,346; Mann, et al. ((1983) *Cell* 33:153); U.S. Pat. No. 4,650,764; U.S. Pat. No. 4,980,289; Markowitz, et al. (1988) *J. Virol.* 62:1120; U.S. Pat. No. 5,124,263; WO 95/07358; and Kuo, et al. ((1993) *Blood* 82:845). Targeted gene delivery is described in WO 95/28494.

Alternatively, the vector can be introduced in vivo by lipofection. Synthetic cationic lipids can be used to prepare liposomes for in vivo transfection of a gene encoding a marker (Feigner, et. al. (1987) *Proc. Natl. Acad. Sci. USA* 84:7413-7417; Mackey, et al. (1988) *Proc. Natl. Acad. Sci. USA* 85:8027-8031). The use of cationic lipids can promote encapsulation of negatively charged nucleic acids, and also promote fusion with negatively charged cell membranes (Feigner and Ringold (1989) *Science* 337:387-388). Lipids can be chemically coupled to other molecules for the purpose of targeting (see Mackey, et. al. (1988) supra). Targeted peptides, e.g., hormones or neurotransmitters, and proteins such as antibodies, or non-peptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, e.g., Wu, et al. (1992) *J. Biol. Chem.* 267:963-967; Wu and Wu (1988) *J. Biol. Chem.* 263:14621-14624).

A regulatable expression vector is particularly useful to regulate expression of a therapeutic EN2 gene. In one embodiment, the present invention contemplates constitutive expression of the EN2 gene, even if at low levels. Various therapeutic heterologous genes can be inserted in a gene therapy vector of the invention such as but not limited to adenosine deaminase (ADA) to treat severe combined immunodeficiency (SCID); marker genes or lymphokine genes into tumor infiltrating (TIL) T cells (Kasis, et al. (1990) Proc. Natl. Acad. Sci. USA 87:473; Culver, et al. (1991) ibid. 88:3155); genes for clotting factors such as Factor VIII and Factor IX for treating hemophilia (Dwarki, et al. (1995) Proc. Natl. Acad. Sci. USA 92:1023-1027); Thompson (1991) Thromb. Haemostatis 66:119-122); and various other well known therapeutic genes such as, but not limited to, dystrophin, insulin, erythropoietin, growth hormone, glucocerebrosidase, glucuronidase, antitrypsin, phenylalanine hydroxylase, tyrosine hydroxylase, ornithine transcarbamylase, apolipoproteins, and the like. In general, see U.S. Pat. No. 5,399,346.

In a further embodiment, the present invention provides for co-expression of EN2 and a therapeutic heterologous gene under control of a specific DNA recognition sequence by providing a gene therapy expression vector comprising both an EN2 coding gene and a gene under control of, inter alia, the EN2 regulatory sequence. The most effective use of this mode of treatment is to administer the gene therapy expression vector by known methods to a pregnant woman at risk of carrying an affected fetus. In this context the EN2 regulatory sequence would target the vector to cells types which are affected in autism. Thus if the gene targeting vector is provided during gestation of a fetus, then the therapeutic gene and/or the EN2 gene itself would be targeted, for example, to neurons which might otherwise fail to develop normally or at all in the fetus. In one embodiment, these elements are provided on separate vectors, e.g., as exemplified infra. These elements may be provided in a single expression vector.

An EN2 protein or nucleic acid of this invention can be a therapeutic compound. A therapeutic compound of the present invention also embraces a drug which decreases, i.e., normalizes (brings to normal levels as described herein) the level of EN2 protein. A drug which normalizes any deleterious downstream effects caused by the presence of SNPs in the EN2 gene are also contemplated by the present invention. Such drugs can be obtained by assays which detect decreases of EN2 protein or its expression or which normalize the expression of genes which are downstream of the EN2 gene. Such assays are part of this invention. A cell-based assay where compounds are tested for the ability to decrease EN2 in cultured cells is one such assay. Accordingly, a drug which decreases the amount of EN2 protein produced by cultured cells is part of this invention.

Such agents include but are not limited to anti-EN2 antibodies that neutralize or antagonize EN2 activity, small organic molecules that bind and inhibit EN2 activity, was well as nucleic-acid based molecules (e.g., miRNA, siRNA, aptamer-siRNA chimera, EN2 binding inhibitor, double-stranded oligonucleotide binding decoy comprising an EN2 binding site, single stranded antisense oligonucleotide, triplex forming oligonucleotide, ribozyme, external guide sequence and combinations thereof) that inhibit EN2 expression.

A short interfering RNA (siRNA) is a double-stranded RNA that can be engineered to induce sequence-specific post-transcriptional gene silencing of EN2, which can decrease or eliminate expression of EN2 protein products. In one embodiment, the siRNA is transcribed, from an expression vector, as a short double-stranded hairpin-like RNA (shRNA) that is processed into an EN2 targeted siRNA inside the cell. In another embodiment, the siRNA is synthetically produced. Synthetically produced siRNAs structurally mimic the types of siRNAs normally processed in cells by the enzyme Dicer. Synthetically produced siRNAs may incorporate any chemical modifications to the RNA structure that are known to enhance siRNA stability and functionality. For example, in some cases, the siRNAs may be synthesized as a locked nucleic acid (LNA)-modified siRNA. An LNA is a nucleotide analogue that contains a methylene bridge connecting the 2'-oxygen of the ribose with the 4' carbon. The bicyclic structure locks the furanose ring of the LNA molecule in a 3'-endo conformation, thereby structurally mimicking the standard RNA monomers. The therapeutic development of LNA-modified siRNAs has been described (Zhang, et al. (2011) Gene Ther. 18:326-333; Veedu, et al. (2009) RNA Biol. 6(3):321-323).

Exemplary siRNA and the corresponding EN2 cDNA sequences are: EN2 cDNA: 5'-TCAACGAGTCACAGAT-CAA-3' (SEQ ID NO:79), sense siRNA: 5'-UCAACGAGU-CACAGAUCAA-3' (SEQ ID NO:80), antisense siRNA: 3'-AGUUGCUCAGUGUCUAGUU-5' (SEQ ID NO:81); EN2 cDNA: 5'-CCAACTTCTTCATCGACAA-3' (SEQ ID NO:82), sense siRNA: 5'-CCAACUUCUUCAUCGACAA-3' (SEQ ID NO:83), antisense siRNA: 3'-GGUUGAAGAAGUAGCUGUU-5' (SEQ ID NO:84); EN2 cDNA: 5'-CTCGAAAACCAAAGAAGAA-3' (SEQ ID NO:85), sense siRNA: 5'-CUCGAAAAC-CAAAGAAGAA-3' (SEQ ID NO:86), and antisense siRNA: 3'-GAGCUUUUGGUUUCUUCUU-5' (SEQ ID NO:87). See US 2012/0157508.

The use of siRNAs exploits the mechanism of RNA interference (RNAi) to silence gene expression of EN2. This "silencing" was originally observed in the context of transfecting double stranded RNA (dsRNA) into cells. Upon entry therein, the dsRNA was found to be cleaved by an RNase III-like enzyme, Dicer, into double-stranded small interfering RNAs of 21-23 nucleotides in length containing two nucleotide overhangs on their 3' ends. In an ATP dependent step, the siRNAs become integrated into a multi-subunit RNAi induced silencing complex (RISC) which presents a signal for AGO2-mediated cleavage of the complementary mRNA sequence, which then leads to its subsequent degradation by cellular exonucleases.

An aptamer-siRNA chimera is a targeted siRNA comprising an siRNA chemically linked to a cell internalizing aptamer. An aptamer is a class of molecules that exhibit high affinity binding to a wide variety of cell surface molecules, proteins, and/or macromolecular structures. Typically, aptamers are small molecules ranging from 15-50 bases in length that fold into defined secondary and tertiary structures, such as stem-loops or G-quartets. Aptamers can bind small molecules, such as ATP and theophiline, as well as large molecules, such as reverse transcriptase, thrombin, and a variety of cell surface receptors.

An aptamer can be chemically linked or conjugated to the above described nucleic acid inhibitors to form targeted nucleic acid inhibitors (Ray, et al. (2010) Pharmaceuticals 3:1761-1778,). An aptamer-siRNA chimera contains a targeting moiety in the form of an aptamer which is linked to an siRNA (Chu, et al. (2006) Nucl. Acids Res. 4(10):e73). In one embodiment, the inhibitor comprises a chimeric aptamer-siRNA oligonucleotide capable of targeting brain tissue. Preferably, the aptamer is a cell internalizing aptamer. Upon binding to specific cell surface molecules, the aptamer can facilitate internalization into the cell where the nucleic acid inhibitor acts. In one embodiment both the aptamer and the siRNA comprises RNA. The aptamer and the siRNA may comprise any nucleotide modifications as further described herein.

Aptamers can bind very tightly with Kds from the target molecule of less than 10-12 M. It is preferred that the aptamers bind the target molecule with a Kd less than 10-6, 10-8, 10-10, or 10-12. Aptamers can bind the target molecule with a very high degree of specificity. For example, aptamers have been isolated that have greater than a 10,000 fold difference in binding affinities between the target molecule and another molecule that differ at only a single position on the molecule.

In particular embodiments, the nucleic-acid based EN2 inhibitor is conjugated to a cell penetrating peptide. Cell penetrating peptides (CPPs) or peptide transduction domains are molecular delivery vehicles that can traverse cell membranes and have been shown to co-transport polynucleotides into neurons. See Meade & Dowdy (2007) Adv. Drug Deliv. Rev. 59:134-40; Davidson (2004) J. Neurosci. 24:10040-6; Mathupala (2009). Exemplary CPPs for use in the present invention include, but are not limited to, HIV TAT49-57 peptide (RKKRRQRRR, SEQ ID NO:88), HIV TAT48-60 peptide (GRKKRRQRRRPPQ, SEQ ID NO:89), low molecular weight protamine (LMWP) peptide (e.g., TDSP5, VSRRRRRRGGRRRR, SEQ ID NO:90, as described in US 2007/0071677); CHARIOT (KETWWETWWTEWSQPK-KKRKV, SEQ ID NO:91), also known as PEP-1 (Morris, et al. (2001) Nat. Biotechnol. 19:1173-1176); Antp43-58 (RQ-IKIWFQNRRMKWKK, SEQ ID NO:92) peptide, MPG (HIV Gp41-5V40 NLS, GALFLGFLGAAGSTM-GAWSQPKKKRKV, SEQ ID NO:93), SAP (VRLPPPVR-LPPPVRLPPP, SEQ ID NO:94), MPG R9 (RRRRRRRRR, SEQ ID NO:95), MAP (KLALKLALKALKAALKLA, SEQ ID NO:96; and KALAKALAKALA, SEQ ID NO:97), K-FGF (AAVALLPAVLLALLAP, SEQ ID NO:98), Penetratin (RQIKIWFQNRRMKWKK, SEQ ID NO:99), Buforin II (TRSSRAGLQFPVGRVHRLLRK, SEQ ID NO:100), Transportan (GWTLNSAGYLLGKINKALAALAKKIL, SEQ ID NO:101), Ku70 (VPMLK, SEQ ID NO:102), Prion (MANLGYWLLALFVTMWTDVGLCKKRPKP, SEQ ID NO:103), pVEC (LLIIILRRRIRKQAHAHSK, SEQ ID NO:104), Pep-7 (SDLWEMMMVSLACQY, SEQ ID NO:105), HN-1 (TSPLNIHNGQKL, SEQ ID NO:106), and CP26 (KWKSFIKKLTSAAKKVVTTAKPLISS (SEQ ID NO:107).

In another embodiment, nucleic-acid based EN2 inhibitor is an antisense oligonucleotide or polynucleotide. The antisense oligonucleotide or polynucleotide may have a DNA backbone, RNA backbone, or chemical derivative thereof. In one embodiment, nucleic-acid based EN2 inhibitor is a single stranded antisense oligonucleotide or polynucleotide targeting EN2 for degradation. In preferred embodiments, the nucleic-acid based EN2 inhibitor is a single stranded antisense oligonucleotide complementary to EN2 mRNA sequences. The single stranded antisense oligonucleotide or polynucleotide may be synthetically produced or it may be expressed from a suitable expression vector. The antisense nucleic acid is designed to bind via complementary binding to the mRNA sense strand so as to promote RNase H activity, which leads to degradation of the mRNA. Preferably, the antisense oligonucleotide is chemically or structurally modified to promote nuclease stability and/or increased binding.

In some embodiments, the antisense oligonucleotides are modified to produce oligonucleotides with nonconventional chemical or backbone additions or substitutions, including but not limited to peptide nucleic acids (PNAs), locked nucleic acids (LNAs), morpholino backboned nucleic acids, methylphosphonates, duplex stabilizing stilbene or pyrenyl caps, phosphorothioates, phosphoroamidates, phosphotriesters, and the like. By way of example, the modified oligonucleotides may incorporate or substitute one or more of the naturally occurring nucleotides with an analog; internucleotide modifications incorporating, for example, uncharged linkages (e.g., methyl phosphonates, phosphotriesters, phosphoamidates, carbamates, etc.) or charged linkages (e.g., phosphorothioates, phosphorodithioates, etc.); modifications incorporating intercalators (e.g., acridine, psoralen, etc.), chelators (e.g., metals, radioactive metals, boron, oxidative metals, etc.), or alkylators, and/or modified linkages (e.g., alpha anomeric nucleic acids, etc.).

In some embodiments, the single stranded oligonucleotides are internally modified to include at least one neutral charge in its backbone. For example, the oligonucleotide may include a methylphosphonate backbone or peptide nucleic acid (PNA) complementary to the target-specific sequence. These modifications have been found to prevent or reduce helicase-mediated unwinding. The use of uncharged probes may further increase the rate of hybridization to polynucleotide targets in a sample by alleviating the repulsion of negatively-charges nucleic acid strands in classical hybridization (Nielsen, et al. (1999) Curr. Issues Mol. Biol. 1:89-104).

PNA oligonucleotides are uncharged nucleic acid analogs for which the phosphodiester backbone has been replaced by a polyamide, which makes PNAs a polymer of 2-aminoethyl-glycine units bound together by an amide linkage. PNAs are synthesized using the same Boc or Fmoc chemistry as are use in standard peptide synthesis. Bases (adenine, guanine, cytosine and thymine) are linked to the backbone by a methylene carboxyl linkage. Thus, PNAs are acyclic, achiral, and neutral. Other properties of PNAs are increased specificity and melting temperature as compared to nucleic acids, capacity to form triple helices, stability at acid pH, non-recognition by cellular enzymes like nucleases, polymerases, etc. (Rey, et al. (2000) FASEB J. 14:1041-1060; Nielsen, et al. (1999) Curr. Issues Mol. Biol. 1:89-104).

Methylphosphonate-containing oligonucleotides are neutral DNA analogs containing a methyl group in place of one of the non-bonding phosphoryl oxygens. Oligonucleotides with methylphosphonate linkages were among the first reported to inhibit protein synthesis via anti-sense blockade of translation. However, the synthetic process yields chiral molecules that must be separated to yield chirally pure monomers for custom production of oligonucleotides (Reynolds, et al. (1996) Nucleic Acids Res. 24:4584-4591).

In some embodiments, the phosphate backbone in the oligonucleotides may contain phosphorothioate linkages or phosphoroamidates (Chen, et al. (1995) Nucl. Acids Res. 23:2662-2668). Combinations of such oligonucleotide linkages are also within the scope of the present invention.

In other embodiments, the oligonucleotide may contain a backbone of modified sugars joined by phosphodiester internucleotide linkages. The modified sugars may include furanose analogs, including but not limited to 2-deoxyribofuranosides, α-D-arabinofuranosides, α-2'-deoxyribofuranosides, and 2',3'-dideoxy-3'-aminoribofuranosides. In alternative embodiments, the 2-deoxy-β-D-ribofuranose groups may be replaced with other sugars, for example, β-D-ribofuranose. In addition, β-D-ribofuranose may be present wherein the 2-OH of the ribose moiety is alkylated with a C1-6 alkyl group (2-(O—C1-6 alkyl)ribose) or with a C2-6 alkenyl group (2-(O—C2-6 alkenyl)ribose), or is replaced by a fluoro group (2-fluororibose).

Related oligomer-forming sugars include those used in locked nucleic acids (LNA) as described above. Exemplary LNA oligonucleotides include modified bicyclic monomeric units with a 2'-O-4'-C methylene bridge, such as those described in U.S. Pat. No. 6,268,490.

Chemically modified oligonucleotides may also include, singly or in any combination, 2'-position sugar modifications, 5-position pyrimidine modifications (e.g., 5-(N-benzylcarboxyamide)-2'-deoxyuridine, 5-(N-isobutylcarboxyamide)-2'-deoxyuridine, 5-(N-[2-(1H-indole-3yl)ethyl]carboxyamide)-2'-deoxyuridine, 5-(N-[1-(3-trimethylammonium)propyl]carboxyamide)-2'-deoxyuridine chloride, 5-(N-napthylcarboxyamide)-2'-deoxyuridine, and 5-(N-[1-(2,3-dihydroxypropyl)]carboxyamide)-2'-deoxyuridine), 8-position purine modifications, modifications at exocyclic amines, substitution of 4-thiouridine, substitution of 5-bromo- or 5-iodo-uracil, methylations, unusual base-pairing combinations, such as the isobases isocytidine and isoguanidine, and the like.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, hairpin ribozymes, and tetrahymena ribozymes. There are also a number of ribozymes that are not found in natural systems, but which have been engineered to catalyze specific reactions de novo. Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence.

Triplex forming oligonucleotides (TFOs) are molecules that can interact with either double-stranded and/or single-stranded nucleic acid. When TFOs interact with a target region, a structure called a triplex is formed, in which there are three strands of DNA forming a complex dependant on both Watson-Crick and Hoogsteen base-pairing. TFOs can bind target regions with high affinity and specificity. In preferred embodiments, the triplex forming molecules bind the target molecule with a Kd less than 10-6, 10-8, 10-10, or 10-12. Exemplary TFOs for use in the present invention include PNAs, LNAs, and LNA modified PNAs, such as Zorro-LNAs (Ge, et al. (2007) FASEB J. 21:1902-1914; Zaghioul, et al. (2011) Nucl. Acids Res. 39(3):1142-1154).

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. Similarly, eukaryotic EGS/RNAse P-directed cleavage of RNA can be utilized to cleave desired targets within eukaryotic cells.

In one embodiment, the agent that inhibits EN2 expression and/or EN2 activity comprises one or more members selected from the group consisting of EN2 siRNA, aptamer-siRNA chimera, single stranded antisense oligonucleotide, triplex forming oligonucleotide, ribozyme, external guide sequence, polynucleotide encoding a EN2 siRNA.

Pharmaceutical compositions including compounds of this invention, preferably EN2 protein, antibodies, or polynucleotides are also part of the invention. Such pharmaceutical compositions are formulated for administration by any standard means, such as injection, oral, pulmonary, nasal, rectal, etc.

In general, comprehended by the invention are pharmaceutical compositions comprising effective amounts of a compound, nucleic acid, antibody or protein of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween™ 80, Polysorbate 80); anti-oxidants (e.g., ascorbic acid, sodium metabisulfite); preservatives (e.g., Thimersol™, benzyl alcohol) and bulking substances (e.g., lactose, mannitol); incorporation of the material into particulate preparations of polymeric compounds such as polylactic acid, polyglycolic acid, etc. or into liposomes. Hylauronic acid can also be used.

Such compositions can influence the physical state, stability, rate of in vivo release, and rate of in vivo clearance of the present proteins and derivatives. See, e.g., *Remington's Pharmaceutical Sciences,* 18th Ed., 1990, Mack Publishing Co., Easton, Pa., pages 1435-1712.

The compositions of the present invention can be prepared in liquid form, or may be in dried powder, such as lyophilized form. Oral solid dosage forms are described generally in Remington's Pharmaceutical Sciences, 18th Ed., 1990, Mack Publishing Co., Easton, Pa. at Chapter 89. Solid dosage forms include tablets, capsules, pills, troches or lozenges, cachets or pellets. Formulations for rectal delivery include suppository formulations, which may be similar to those prepared for oral delivery. Also, liposomal or proteinoid encapsulation may be used to formulate the present compositions (as, for example, proteinoid microspheres reported in U.S. Pat. No. 4,925,673). Liposomal encapsulation can be used and the liposomes can be derivatized with various polymers (e.g., U.S. Pat. No. 5,013,556). A description of possible solid dosage forms for the therapeutic is given by Marshall (1979) In: Modern Pharmaceutics, Banker and Rhodes, ed., Chapter 10.

In general, the formulation will include the component or components (or chemically modified forms thereof) and inert ingredients which allow for protection against the stomach environment, and release of the biologically active material in the intestine. The active compounds can be chemically modified so that oral delivery is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline.

One can dilute or increase the volume of the therapeutic with an inert material such as carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Materials used as disintegrates include, but are not limited to, starch including sodium starch glycolate, Amberliteu™, sodium carboxymethylcellulose, ultramylopectin, sodium alginate, gelatin, orange peel, acid carboxymethyl cellulose, natural sponge and bentonite, and insoluble cationic exchange resins. Powdered gums as disintegrants and as binders can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic. An antifrictional agent can also be included.

Lubricants such as stearic acid including its magnesium and calcium salts, polytetrafluoroethylene (PTFE), liquid paraffin, vegetable oils and waxes, sodium lauryl sulfate, magnesium lauryl sulfate, polyethylene glycol of various molecular weights, Carbowax® 4000 and 6000 can be used. Glidants may include starch, talc, pyrogenic silica and hydrated silicoaluminate. A surfactant can be added as a wetting agent. Surfactants can include anionic detergents such as sodium lauryl sulfate, dioctyl sodium sulfosuccinate and dioctyl sodium sulfonate. Cationic detergents might be used and could include benzalkonium chloride or benzethomium chloride. Anionic detergents that could be included are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. Additives which potentially enhance uptake of the protein are for instance the fatty acids oleic acid, linoleic acid and linolenic acid.

Controlled release oral formulation may be desirable. Pulmonary delivery by known methods, for example as described in U.S. Pat. No. 5,451,569, is also contemplated. Vehicles include but are not limited to nebulizers, metered dose inhalers, and powder inhalers. All such devices require the use of suitable formulations. Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated.

Chemically modified protein may also be prepared in different formulations depending on the type of chemical modification or the type of device employed. Formulations for nasal delivery include those with dextran or cyclodextran. For injectable compositions, various standard aqueous formulations are suitable.

In accordance with the above, the therapeutic compounds of the present invention can be delivered by standard means including intravenous, intraarterial, intraperitoneal, intramuscular, intracerebral, intraventricular, intrathecal or subcutaneous routes of administration. Alternatively, these compounds, properly formulated, can be administered by nasal, oral, or rectal administration. A constant supply of these therapeutic compounds can be ensured by providing a therapeutically effective dose, i.e., a dose effective to induce normalized (i.e., increased or decreased) levels of EN2 protein in a subject at the necessary intervals, e.g., daily, every 12 hours, etc. These parameters will depend on the severity of the disease condition being treated, other actions, such as diet modification, that are implemented, the weight, age, and sex of the subject, and other criteria, which can be readily determined according to standard good medical practice by those of skill in the art. Normal levels of EN2 protein can be determined as described above. The subject can be tested to determine whether levels are normalized by, for example, determining the amount of EN2 protein in the cells or tissues of the subject. Similarly dosage can be titrated during treatment by determining whether levels of EN2 protein are increasing or decreasing compared to the subject's levels of EN2 before treatment.

The therapeutic compound can be delivered in a vesicle, in particular a liposome (see Langer (1990) Science 249: 1527-1533; Treat, et al. (1989) In: Liposomes in the Therapy of Infectious Disease and Cancer, Lopez-Berestein and Fidler (eds.), Liss: New York, pp. 353-365; Lopez-Berestein, ibid., pp. 317-327). The therapeutic compound can be delivered in a controlled release system, may be administered using intravenous infusion, an implantable osmotic pump, a transdermal patch, liposomes, or other modes of administration. In one embodiment, a pump can be used (see Langer, supra; Sefton (1987) CRC Crit. Ref. Biomed. Eng. 14:201; Buchwald, et al. (1980) Surgery 88:507; Saudek, et al. (1989) *N. Engl. J. Med.* 321:574). In another embodiment, polymeric materials can be used (see Medical Applications of Controlled Release, Langer and Wise, eds. (1974) CRC Press: Boca Raton, Fla.; Controlled Drug Bioavailability, Drug Product Design and Performance (1984) Smolen and Ball (eds.), Wiley: New York; Ranger and Peppas (1983) J. Macromol. Sci. Rev. Macromol. Chem. 23:61; Levy, et al. (1985) Science 228:190; During, et al. (1989) Ann. Neurol. 25:351; Howard, et al. (1989) J. Neurosurg. 71:105). In yet another embodiment, a controlled release system can be placed in proximity of the therapeutic target, i.e., the brain, thus requiring only a fraction of the systemic dose (see, e.g., Goodson (1984) In: Medical Applications of Controlled Release, supra, vol. 2, pp. 115-138).

In a particular embodiment, a nucleic acid-based EN2 inhibitor is delivered via exosomes, i.e., nano-vesicles that transport RNAs and proteins, to the brain. Purified exosomes, loaded with exogenous siRNA by electroporation, have been shown to provide specific gene knockdown in neurons, microglia, oligodendrocytes of the brain when intravenously injected (Alvarez-Erviti, et al. (2011) Nat. Biotechnol. 29:341-345).

In another embodiment, pegylated immunoliposomes are used to deliver plasmid DNA, encoding for shRNA, to the brain. See, Pardridge (2007) Adv. Drug Deliv. Rev. 59:141-52.

A subject in whom administration of these therapeutic agents is an effective therapeutic regimen is preferably a human, but can be any animal. The amount administered is an amount effective to normalize the amount of EN2 protein in the subject, whether by increasing or decreasing the amount of protein or the expression of the protein. Thus, as can be readily appreciated by one of ordinary skill in the art, the methods and pharmaceutical compositions of the present invention are particularly suited to administration to any animal, i.e., for veterinary medical use.

Detection of deletions, additions, substitutions and any other mutations can be carried out according to standard methods. In general, the identification of a mutation that involves as little as one nucleotide can be achieved by observing the mutation through nucleotide sequence analysis or a change in an amino acid through amino acid sequence analysis, using techniques known in the art. For example using probes developed from the EN2 sequence provided herein, or PCR primers provided herein, a suspected mutant gene can be obtained from cells or tissue using known techniques. The gene can then be sequenced by standard methods, and the mutation observed by comparing sequences. Alternatively, the gene can be expressed in an expression vector, again using standard protocols, and the resulting protein isolated and sequenced to provide a sequence comparison. An example of a mutant analysis method is single-strand polymorphism mutation screening (SSCP), which employs a PCR-based protocol to accomplish mutation screening. As discussed above, a mutation can comprise one or more deletions, additions, or substitutions of nucleotides. The mutation can be in a coding region, which would affect the sequence of the resulting protein. The mutation can also be in the 5' or 3' noncoding region, which would affect expression of protein, by for example affecting the promoter or enhancer, or by affecting the 3'-UTR (affecting RNA stability). A mutation can be as small as one nucleotide, or as large as the entire gene.

Suitable hybridization probes for use in accordance with the methods of the present invention include SEQ ID NO:1, which encompasses the coding sequence of EN2 and SEQ ID NO:11, which encompasses the intron of the EN2 locus. SEQ ID NO:2, is the complete sequence of the human EN2 protein. DNA sequences encoding the EN2 protein, segments thereof, and sequences complementary in base sequence to said sequences and segments, are preferred hybridization probes in assays for RNA levels. Probes against EN2 intron sequences, obtainable from the results of the Human Genome Project, can also be used as EN2 gene-specific probes. In particular embodiments, the probe hybridizes to a nucleic acid sequence at or near SNPs rs1861972, rs1861973 or rs2361688. Probes for segments of the EN2 gene or mRNA can be isolated, for example, by cloning the EN2 gene or cDNA and using PCR to amplify desired regions of the cloned nucleic acid to create a probe population.

Hybridization assays are done under conditions where a probe complementary to a segment of EN2 nucleic acid will preferentially bind to that nucleic acid, as compared to other nucleic acid. An extensive volume of literature exists on various appropriate hybridization conditions for achieving such specificity.

Hybridization can be done by a variety of methods. The optimal solvent composition, probe size, and temperature, will depend on whether the target nucleic acid is for example, in solution, on a solid support (e.g., a nitrocellulose filter) in solution, and or in a cell. Conditions will also depend on whether the probe is in solution or in a solid support (e.g., in a gene chip experiment). The hybridization conditions described for the northern blot experiments below are illustrative of possible hybridization conditions. Persons in the art will appreciate which conditions are optimal for the various types of possible hybridization experiments.

Single base mutations can, for example, be detected by nucleic acid sequencing, by SSCP, or by hybridization with small probes that require a perfectly complementary target sequence in order to hybridize. In particular embodiments, a single-base mutation indicative of a person inflicted with, or predisposed to, an autism spectrum disorder is a A to G transition at position 2236 of SEQ ID NO:11 (rs1861972); a C to T transition at position 2388 of SEQ ID NO:11 (rs1861973); a A to G transition at position 1921 of SEQ ID NO:11 (rs2361688); or a combination thereof.

The results of the various assays can be analyzed to determine whether one or both genes have the deletion. For example, if Southern electrophoretic gel analysis of restriction digests of cell DNA reveals the presence of half as much intact EN2 gene DNA as a normal person (as regards the EN2 gene) has, that will indicate that only one of the two gene copies is missing. Also hybridization to chromosomes in situ or in chromosomal preparations, using fluorescent in situ hybridization or other hybridization techniques, can show if the deletion of a gene is in one or both chromosomes of a chromosome pair. A gel analysis may also reveal an alteration in the pattern of bands from a normal DNA sample. For example, a deletion will move its two flanking regions containing restriction sites closer to each other, resulting in different sized fragments than normal DNA when exposed to the same restriction enzyme.

In certain embodiments of the diagnostic methods and kits, EN2 defects are determined by protein analysis, wherein the protein is isolated from a patient for purposes of determining subnormal levels of protein, especially EN2 protein. Protein may be isolated from cell, tissue, or blood samples using known methods of protein isolation from these materials. In particular, a given protein such as EN2 can be isolated using antibodies. Once isolated, the protein can be sequenced by known methods to determine whether it is a mutant protein. See, for example, Vladimirov, et al. (1996) Eur. J. Biochem. 239:144-149; Wang and Chait (1997) Methods Mol. Biol. 64:175-182; Hines, et al. (1998) J. Protein Chemistry 17:525-526).

In particular embodiments of the diagnostic methods and kits, an antibody probe is used in an assay for purposes of demonstrating the subnormal levels of protein, especially the EN2 protein. Antibodies can be obtained as described above. Also, antibodies that react with EN2 protein have been reported (Ericson, et al. (1992) Science 256:1555-1560; Ericson, et al. (1997) Cell 90:169-180). EN2 size and amount can be determined by western blot analysis.

As used in the context of the present invention, autism includes any form of autism. Such diseases are currently denoted as autism or an autistic spectrum disorder which includes Asperger's Syndrome and Pervasive Developmental Disorder (PDD).

The "DSM-IV" criteria for autistic disorder are those set forth in the American Psychiatric Association's Diagnostic and Statistical Manual of Mental Disorders, 4th edition, Washington, D.C., 199 pp 70-71. The diagnosis is based on the presence of 6 or more diagnostic criteria from three possible Groups 1, 2, and 3 with at least two of the criteria being from Group 1, at least one from Group 2, and at least one from Group 3. The three groups correspond to three core symptoms:

Group 1—Qualitative impairment in social interaction.
Group 2—Qualitative impairment in communication.
Group 3—Restricted repetitive and stereotyped patterns of behavior, interests and activities.

The four diagnostic criteria in Group 1 are: (i) marked impairment in multiple nonverbal behaviors (e.g., eye to eye gaze, facial expression, body postures, and gestures to regulate social interaction); (ii) failure to develop peer relationships appropriate to developmental level; (iii) absence of spontaneous seeking to share enjoyment, interests, or achievements with others (e.g., lack of showing, bringing, or pointing out objects of interest); and (iv) absence of social or emotional reciprocity.

The four diagnostic criteria in Group 2 are: (i) delay in, or total absence of spoken language development (without an attempt to compensate through alternative modes of communication, such as gesture or mime); (ii) adequate speech but marked impairment in ability to initiate or sustain a conversation with others; (c) stereotyped and repetitive use of language or idiosyncratic language; and (iv) absence of varied, spontaneous make-believe play or social imitative play appropriate to developmental level.

The four diagnostic criteria in Group 3 are: (i) encompassing preoccupation with one or more stereotyped and restricted patterns of interest that is abnormal either in intensity or focus; (ii) inflexible adherence to specific non-functional routines or rituals, stereotyped and repetitive motor mannerisms (e.g., hand or finger flapping or twisting, or complex whole-body movements); and (iv) persistent preoccupation with parts of objects.

Diagnosis of autism using the DSM-IV criteria, followed by confirmation of the diagnosis by the Autism Diagnostic Interview-Revised (ADI-R), provides good results. The ADI-R is a well-known review process for establishing autism (see, for example, Lord, et al. (1994) J. Autism Dev. Disord. 2:659-85; Le Couteur, et al. (1989) J. Autism Dev. Disord. 19:363-87).

In the Examples described here, the clinical diagnosis was determined by the DSM-IV criteria and then each individual was then subjected to the Autism Diagnostic Interview-Revised (ADI-R). The autistic individuals were identified by having at least six of the items described above.

Genes that are directly regulated by EN2 are also part of this invention. Mutations in EN2 may result in increase or decrease of the expression of these genes. Such downstream genes may be expressed at increased or decreased levels when EN2 is downregulated, and this is one means of isolating such genes using known methods. For example, cerebellar anlage (e10.5) could be dissected from EN2−/− knockout mice and wild-type littermates and their mRNA isolated to determine which are expressed at lower levels. For example, the mRNA could be hybridized against microarrays containing all the genes from the mouse genome. Genes directly regulated by EN2 such as PCP2 (L7) (Sanlioglu, et al. (1998) J. Neurobiol. 36:559-71) may be expressed at higher or lower levels than the others.

The invention is described in greater detail by the following non-limiting examples.

EXAMPLE 1

Transmission Disequilibrium Analysis—Study 1

Families recruited to the Autism Genetic Resource Exchange (AGRE) were used for these studies. AGRE is a central repository of family DNA samples created by The Cure Autism Now (CAN) Foundation and the Human Biological Data Interchange. The selection criteria required was that at least two family members had been diagnosed with autism, Asperger's Syndrome or PDD. The diagnosis and characteristics of these families are described in detail elsewhere (Geschwind, et al. (2001) *Am. J. Hum. Genet.* 69:463-6; Liu, et al. (2001) *Annu. Rev. Neurosci.* 24:869-896). For the analysis disclosed herein, a narrow diagnosis was defined as only autism while a broad diagnostic included individuals affected with either autism, Asperger's Syndrome or PDD. In this study, 137 triads (parent-offspring trios) under the narrow diagnostic were initially evaluated. This was then extended to a total of 166 pedigrees that included 310 triads and 168 phenotypic discordant sib pairs (DSP) under the broad diagnosis (740 total subjects). For the narrow diagnostic, 163 pedigrees with 250 triads and 134 DSP were analyzed (n=672).

EN2 spans 8 kb of the genome and is encoded by two exons separated by a single intron. SNPs within the EN2 gene were initially identified through genome browsers. Two SNPs (rs1861972 and rs1861973) located 152 bp apart in the intron were initially verified by DNA sequence analysis of 24 individuals.

words, these data indicated that if the population were monomorphic for the G (protective) allele the prevalence of autism would be 62% lower. Since the GRR and PAR were calculated from a sample population ascertained for multiple affected siblings, the actual risk estimates may be different in the general AS population.

A similar distortion of transmissions was observed for the rs1861973 SNP with 70 of 105 heterozygous parents (67%) preferentially transmitting the C allele to their Autistic offspring (McNemar's $\chi^2$=11.67, df=1, P=0.0006) (Table 1). The C allele of the rs1861973 SNP provided a GRR of 2.00 with a corresponding PAR of 66%.

Haplotype transmission/disequilibrium tests were then performed again using TRANSMIT software. In the population tested, the A-C haplotype had an observed frequency of 67.6%. This haplotype was specifically overtransmitted (80 transmitted vs. 36 untransmitted) to affected individuals ($\chi^2$=16.07, df=1, P=0.000062) (Table 2). The G-T, A-T, and G-C haplotypes were all undertransmitted (Table 2). The global $\chi^2$ test based upon the common haplotypes A-C and G-T (frequency>5%) was then calculated to be $\chi^2$=18.90 (df=2), with a corresponding P-value of 0.000079 (Table 2).

TABLE 1

| dbSNP No. | Polymorphism[a] | Frequency[b] | T[c] | U[c] | P-value[d] | GRR[e] | PAR[f] |
|---|---|---|---|---|---|---|---|
| rs1867972 | A/G | 0.297 | 77 | 41 | 0.0009 | 1.88 | 62% |
| rs1861973 | C/T | 0.292 | 70 | 35 | 0.0006 | 2.00 | 66% |

[a]Second allele is rare allele.
[b]Frequency of rare allele.
[c]T = number of times frequent allele transmitted and U = number of times frequent allele not transmitted from heterozygous parents.
[d]Two-sided P-value (1df) corresponding to $\chi$2 generated by TRANSMIT.
[e]Genotype relative risk estimated by transmission ratio (T/U) assuming a multiplicative model.
[f]Population attributable risk calculated as PAR = (X − 1)/X; where X = (1 − f)2 + 2f(1 − f)$\gamma$ + f$^2\gamma^2$ and $\gamma$ = GRR.

The tetra-primer ARMS-PCR strategy was then used to genotype family members (Ye, et al. (2001) *Nucl. Acids Res.* 29:E88-8). Primers were selected using a web-based software program and PCR conditions were determined that allowed the specific amplification of all possible genotypes. Genotypes for both SNPs were determined for the initial 137 triads that displayed just the narrow diagnostic and were verified to be in Hardy Weinberg equilibrium. The frequencies for the A and G alleles of rs1861972 were 70.3 and 29.7, respectively (Table 1). Similar values were observed for rs1861973 (C=70.8 and T=29.2) (Table 1). There was a significant positive linkage disequilibrium (LD) between the alleles of these markers (delta=0.82, delta-$\chi^2$=227.96, df=1, P<0.00001) (Hill and Weir (1994) *Am. J. Hum. Genet.* 54: 705-714).

Allelic transmission distortions were assessed for each SNP by the transmission disequilibrium test (TDT) (Spielman, et al. (1993) *Am. J. Hum. Genet.* 52:506-516), using the TRANSMIT program (Clayton (1999) *Am. J. Hum. Genet.* 65:1170-1177). Excess transmission of the rs1861972 A-allele to affected offspring was observed, with 77 of 118 heterozygous parents (65%) transmitting the A-allele and only 41 transmitting the G allele (McNemar's $\chi^2$=10.98, df=1, P=0.0009) (Table 1). Under a multiplicative model, the transmission ratio Transmitted/Untransmitted (T/U) is an estimator of genotype relative risk (GRR) (Altshuler, et al. (2000) *Nat. Genet.* 26:76-80). The GRR attributable to the A allele of the rs1861972 SNP was estimated to be 1.88 which in turn corresponded to a population attributable risk (PAR) (Altshuler, et al. (2000) *Nat. Genet.* 26:76-80) of approximately 62%. In other These tests were then reiterated 50000 times by a bootstrap simulation procedure to control for ambiguous haplotypes. Similar empirical P-values as before were obtained (P=0.00012) (Table 2). The GRR attributable to the A-C haplotype was found to be 2.19 with a corresponding PAR of 69%. Together this analysis demonstrates that the EN2 A-C haplotype is overtransmitted and is a high risk haplotype in autistic individuals.

TABLE 2

| Haplotype | Frequency | T | U | P-value[a] |
|---|---|---|---|---|
| A-C[b] | 0.676 | 79 | 36 | 0.000062 |
| A-T | 0.032 | 4 | 12 | 0.0455 |
| G-C | 0.028 | 3 | 10 | 0.0525 |
| G-T | 0.262 | 39 | 67 | 0.0065 |
| Global[c] | | | | 0.000079 |
| Global[d] | | | | 0.00012 |

[a]Two-sided P-value corresponding to $\chi^2$ generated by TRANSMIT.
[b]GRR = 2.19, PAR = 69%.
[c]Global $\chi^2$ test based on combined common haplotypes, frequency greater than 5% (2df).
[d]Bootstrap simulation of global $\chi^2$ test (50000 reiterations).

To determine whether these findings could be extended to a larger sample, affected and unaffected siblings from the original 137 triads and 29 additional families were examined. The inheritance of each SNP was then assessed in these extended pedigrees using the Pedigree Disequilibrium Test (PDT) (Martin, et al. (2000) *Am. J. Hum. Genet.* 67:146-154). This program was used in place of TRANSMIT for the analysis of the extended pedigrees since the inevitable non-independence of affected siblings would render analysis conducted using TRANSMIT and other similar programs as invalid tests of association though they remain appropriate for linkage analysis. PDT has been specifically designed to overcome this limitation by allowing the use of data from related triads and discordant sibships from extended families when testing for LD.

For rs1861972, the A allele was again overtransmitted from heterozygous parents when individuals under a broad or narrow diagnostic were included in the analysis (narrow: 120 transmitted vs. 82 untransmitted; and broad: 150 transmitted vs. 107 untransmitted). The A allele was also over-represented in affected siblings of DSPs (defined by both genotypic and phenotypic discordance) under both diagnostics (narrow: 67 alleles in affected and 50 in unaffected siblings of 44 genotypic DSPs; broad: 89 in affected and 63 in unaffected of 57 genotypic DSPs). These results were significant when analyzed by PDT (narrow P=0.0106, broad P=0.0050) (Table 3).

TABLE 3

| dbSNP No. | Diagnostic | Parental Transmissions | | DSP[a] | | | P-value[b] |
|---|---|---|---|---|---|---|---|
| | | T | U | A | UA | Total | |
| rs1867972 | narrow | 120 | 82 | 67 | 50 | 44 | 0.0106 |
| rs1867972 | broad | 150 | 107 | 89 | 63 | 57 | 0.0050 |
| rs1867973 | narrow | 108 | 68 | 59 | 40 | 37 | 0.0033 |
| rs1867973 | broad | 129 | 90 | 73 | 50 | 46 | 0.0063 |

[a]Discordant sibpair counts: A = total number of the common allele in affected siblings and UA = total number of the common allele in unaffected siblings of genotypic discordant DSPs; Total = total number of genotypic discordant DSPs.
[b]P-value generated by PDT.

Analysis for the rs1861973 SNP revealed a similar pattern. The C allele was again overtransmitted to affected individuals (narrow: 108 transmitted vs. 68 untransmitted, broad: 129 transmitted vs. 90 untransmitted) and over-represented in affected siblings of DSPs (narrow: 59 in affected and 40 in unaffected of 37 genotypic DSPs; broad: 73 vs. 50 in affected and unaffected siblings respectively of 46 genotypic DSPs). This inheritance pattern was significant under the broad and narrow diagnosis when analyzed by PDT (narrow P=0.0033, broad P=0.0063) (Table 3). Thus, rs1861972 and rs1861973 demonstrate significant association to both autism and related AS disorders.

Haplotype analysis on the extended pedigrees was then performed. Since the two SNPs were in tight linkage disequilibrium (LD) and were only 152 bp apart from each other, a recombination event likely occurred between them in a sample of this size. In the absence of recombination, unambiguous haplotypes could be assigned to all individuals in 160 of the 166 pedigrees. In only 6 families the parental haplotype phase could not be distinguished. These pedigrees were omitted for further analysis. Each haplotype was recoded as a single allele. By recoding the haplotypes as a single locus, the transmissions could be analyzed by PDT. The A-C haplotype was again overtransmitted under both diagnostic classifications (narrow: 120 transmitted vs. 66 untransmitted, broad: 143 transmitted vs. 86 untransmitted) and over-represented in affected siblings of DSPs (narrow: 64 vs. 45 from 44 genotypic DSPs; broad: 76 vs. 53 from 52 genotypic DSPs) at significant levels (narrow P=0.0007, broad P=0.0009) (Table 4). Conversely, the A-T, G-C, and G-T haplotypes were all undertransmitted. Global $\chi^2$ tests for all haplotypes also yielded significant P-values (narrow P=0.0003, broad P=0.0005) (Table 4). These results demonstrate significant association between EN2 and autism spectrum disorders.

TABLE 4

| Haplotype[a] | Diagnostic | Parental Transmissions | | DSP | | | P-value[b] |
|---|---|---|---|---|---|---|---|
| | | T | U | A | UA | Total | |
| A-C | narrow | 120 | 66 | 64 | 45 | 44 | 0.0007 |
| A-T | narrow | 7 | 21 | 1 | 3 | 4 | 0.0136 |
| G-C | narrow | 7 | 20 | 3 | 5 | 8 | 0.0997 |
| G-T | narrow | 69 | 96 | 17 | 30 | 35 | 0.0299 |
| Global | narrow | | | | | | 0.0003 |
| A-C | broad | 143 | 86 | 76 | 53 | 52 | 0.0009 |
| A-T | broad | 10 | 25 | 1 | 3 | 4 | 0.0195 |
| G-C | broad | 9 | 26 | 4 | 5 | 9 | 0.0587 |
| G-T | broad | 92 | 117 | 20 | 40 | 43 | 0.0634 |
| Global | broad | | | | | | 0.0005 |

[a]Haplotypes recoded as alleles prior to PDT analysis.
[b]P-value generated by PDT.

The haplotype transmissions were also investigated for parent of origin and sex differences using ETDT (Sham and Curtis (1995) Ann. Hum. Genet. 59:323-336) and TRANSMIT software, respectively. When maternal and paternal transmissions were investigated separately, no parental differences in transmission ratios was observed. Male and female affected individuals are also equally likely to inherit the A-C haplotype. Thus, these data do not support a significant parent of origin or sex bias effects.

Computer prediction programs indicated that these polymorphisms did not introduce new splice acceptor or donor sites. Similar analysis was used to demonstrate that the A and G alleles of rs1861972 did not alter any putative transcription factor binding sites in the intron. However, the C allele for rs1861973 generated a consensus binding site for the general transcription factor, Sp1. This difference in transcription factor binding could alter the transcriptional regulation of EN2 and confer risk to autism.

These data represent the most significant genetic association reported for AS disorders. The overtransmission of the A and C alleles of both SNPs indicate risk or these SNPs are in linkage disequilibrium with other polymorphisms that contribute to autism.

The results of this association study together with the similarities in the cerebellar phenotype observed in the mouse knockout and autistic individuals make EN2 an excellent candidate for an autism susceptibility locus. Using the transmission data observed in the sample population disclosed herein, a genotype relative risk was estimated at 2.19 and a population attributable risk of 69% for the A-C predisposing haplotype. In other words, these data indicate that if the population were monomorphic for the G and T (protective) alleles, the prevalence of autism would be 69% lower. These data indicate a highly significant role for variation at this locus in the etiology of AS. Since the GRR and PAR were calculated from a sample population ascertained for multiple affected siblings, the actual risk estimates could be different in the general AS population. Estimates of GRR in multiplex sibships compared with singleton families were thought to be distorted depending on the background heritability (multilocus model of the disorder). The GRR was in fact expected to be deflated at a rate that was proportional to an increase in background heritability and more accurately estimated in situations of low background heritability (Risch (2001) Theor. Popul. Biol. 60:215-220). Given the complex polygenic model of inheritance with anywhere between 3-15 interacting loci that have been proposed for AS, other loci may contribute to the phenotype.

En2 functions in cerebellar patterning during development. Although En2 is expressed as early as embryonic day 9.5 during mouse cerebellar development, it is believed to be redundant to En1 in anterior-posterior patterning of the neural tube necessary to form the cerebellum (Hanks, et al. (1995) *Science* 269:679-682; Liu and Joyner (2001) *Annu. Rev. Neurosci.* 24:869-896). The knockout has demonstrated that En2 is essential for normal postnatal cerebellar development (Millen, et al. (1994) *Development* 120:695-706; Millen, et al. (1995) *Development* 121:3935-45; Kuemerle, et al. (1997) *J. Neurosci.* 17:7881-9). Although the cerebellum is often noted for its uniform structure, anatomical and biochemical studies have determined that the cerebellum is highly patterned. A number of genes including En2 are expressed in stripes in the postnatal cerebellum. These genes are believed to coordinate both the differential proliferation that is potentially responsible for proper cerebellar foliation as well as the topographic mapping of spinocerebellar and olivocerebellar afferents (Hawkes and Eisenmann (1997) *Perspect. Dev. Neurobiol.* 5:95-105). In the En2 knockout, this postnatal patterning is disrupted as evidenced by abnormal gene expression, foliation and misrouting of afferents (Vogel, et al. (1996) *Brain Res. Dev. Brain Res.* 96:210-218; Kuemerle, et al. (1997) *J. Neurosci.* 17:7881-9). This abnormal patterning could either directly affect cerebellar function or indirectly perturb interacting forebrain structures that mediate altered social, language and cognitive abilities observed in autism.

EXAMPLE 2

Transmission Disequilibrium Analysis—Study 2

The analysis presented in Example 1 demonstrated that the A allele of rs1861972 and the C allele of rs1861973 were significantly associated with ASD individually and as a haplotype under both narrow and broad diagnostic criteria. Replication of these association results is now observed in both another 222 AGRE families (AGRE II) and 129 National Institute of Mental Health (NIMH) families.

Subjects. Families recruited to the AGRE and to the NIMH Center for Collaborative Genetic Studies were used for this study (Risch, et al. (1999) *Am. J. Hum. Genet.* 65:493-507; Geschwind, et al. (2001) *Am. J. Hum. Genet.* 69:463-466).

The AGRE I dataset included 167 families, while the AGRE II dataset included 222 additional families. Family selection criteria have been described (Liu, et al. (2001) *Am. J. Hum. Genet.* 69:327-340; Geschwind, et al. (2001) supra). Families recruited by AGRE included at least two affected siblings (diagnosed with either autism, Asperger's Syndrome or Pervasive Development Disorder-Not Otherwise Specified (PDD-NOS)), one or both parents and additional affected and unaffected siblings when available. Although unaffected siblings had not undergone an Autism Diagnostic Interview-Revised (ADI-R) evaluation, in the combined AGRE sample extensive neurological, psychological and medical evaluations were available for 69 of the 277 unaffected siblings. None of the unaffected siblings displayed characteristics of a broad autism phenotype. Fragile X information was available for 381 of the 399 AGRE families considered for use in this study. Ten families were removed because at least one individual per family displayed a pre, intermediate or full Fragile X mutation state. Karyotypic data was available for 109 AGRE families used in this study. Five karyotypically abnormal families with a duplication of SNRPN on chromosome 15q12 (a marker for cytogenic abnormality at the chromosome 15 autism critical region) were also removed.

The NIMH dataset included 143 families. 14 of these families were also included in the AGRE datasets so were removed from this analysis. Selection criteria have been described previously (Risch, et al. (1999) supra) and anonymous data on family structure, age, sex, diagnostic interview data and status were available. Families in the NIMH dataset had at least 2 affected siblings or more distantly related individuals (e.g., cousins) with a diagnosis of autism or another pervasive developmental disorder, without any associated primary disorder such as Fragile X syndrome. The majority of the families included in the collection were affected sib multiplex families. 46 of the 53 unaffected children have undergone ADI-R evaluation and these individuals did not meet criteria for any ASD (Risch, et al. (1999) supra). The diagnosis for six individuals was uncertain and one individual did not meet ASD criteria by the ADI-R but exhibited behavioral and developmental abnormalities. These seven individuals were excluded from the analysis. No karyotype data was available for the NIMH dataset. For this analysis, individuals were considered affected under a narrow diagnostic definition if they were diagnosed with autism, while they were considered affected under a broad diagnostic definition if they were diagnosed with autism, Asperger's syndrome, or PDD-NOS.

Thirty-two of the families in the AGRE II sample and 20 in the NIMH sample included multiple births. In the AGRE II sample there were 19 families with MZ multiple births (16 MZ twins were autism:autism concordant, 2 were autism:PDD discordant, and 1 was MZ autism:autism concordant quadruplets), 11 families with DZ multiple births (9 twins and two triplets), and two additional families with twins of unknown zygosity. In the NIMH sample, 10 families had MZ twins (9 MZ twins were autism:autism concordant and 1 was autism:PDD discordant), 9 families had DZ twins, and one family had a triplet with a MZ pair and a third DZ sibling (all were autism:autism concordant). DNA was available for all twins in both datasets and all siblings were genotyped. All DZ were included in the data analysis, but for MZ siblings only the first MZ cotwin was selected for analysis.

DNA Analysis. Samples in the AGRE II and NIMH dataset were genotyped for the SNPs rs1861972 and rs1861973 using simplex PYROSEQUENCING™ assays and the automated PSQ HS 96A platform according to established methods (Ronaghi, et al. (1998) *Science* 281:363-365; Ahmadian, et al. (2000) *Anal. Biochem.* 280:103-110). Fourteen additional polymorphisms (rs6150410, rs1345514, rs3735653, rs3735652, rs6460013, rs7794177, rs3824068, rs2361688, rs3824067, rs3808332, rs3808331, rs4717034, rs2361689, rs3808329) were genotyped in the AGRE I dataset, 12 were identified by dbSNP. The PvuII RFLP, suggested to be associated with autism (Petit, et al. (1995) *J. Med. Genet.* 32: 269-274), was identified as a -/CG insertion/deletion polymorphism by sequence analysis and comparisons to published RFLP reports (Logan and Joyner (1989) *Nucleic Acids Res.* 17(7):2879). For PvuII and rs2361688, a PvuII and HinfI RFLP assay was used respectively. An additional intronic SNP (ss38341503) was identified by sequence analysis. Each dbSNP polymorphism was sequence verified using 24 unrelated individuals (23 Caucasian and 1 of Hispanic/Latino descent) prior to the design of genotyping assays. A standard PCR amplification followed by allele separation on a 10% polyacrylamide gel electrophoresis assay was used to genotype the rs6150410 insertion/deletion polymorphism. Genotypes were called based upon band size differences of 263-bp (insertion allele) and 254-bp (deletion allele). Primers were designed using publicly available software (see Table 5). For rs6460013, rs7794177, rs1264067, rs3808332, rs3808331 and rs4717034, a tetra-primer ARMS-PCR strategy was used to genotype individuals (Ye, et al. (2001) *Nucleic Acids Res.* 29:E88-8). Primers were designed using the publicly available software (see Table 5). For rs3735652, ss38341503, and rs3808329, a ligase detection reaction (LDR) and the LUMINEX™ 100 flow cytometry platform was used (Iannone, et al. (2000) *Cytometry* 39(2):131-40).

TABLE 5

| SNP Primers | Sequence | SEQ ID NO: |
|---|---|---|
| rs6150410 | | |
| Forward | ctagagggaaaacggggttc | 12 |
| Reverse | aactccgcaaggtgtttcag | 13 |
| PvuII | | |
| Forward | tggcagatgtgtgcctag | 14 |
| Reverse | ccagaccggtcatctcgttttc | 15 |
| rs1345514 | | |
| Forward | agagctgccctatcggatgtt | 16 |
| Reverse | aaactaattttgccggagagc | 17 |
| Pyrosequencing ™ | cccaccaaacaccc | 18 |
| rs3735652 | | |
| Forward | ctgtcggtgagctcggact | 19 |
| Reverse | tggaagacagagaggggaga | 20 |
| Luminex™ G | gcgacattgtgtgaagctgacg | 21 |
| Luminex™ C | gcgacattgtgtgaagctgacc | 22 |
| Luminex™ common | ccggcccgggcagcggc | 23 |
| rs6460013 | | |
| Forward outer | cgcatctcttcccagccctagc | 24 |
| Reverse outer | tgcatcctcctgagtcccaccg | 25 |
| Forward inner | ccttccctacgatcttccaactcggg | 26 |
| Reverse inner | gcatgcgtccccggcctaga | 27 |
| rs7794177 | | |
| Forward outer | cacagggaaggaggaaaataaa | 28 |
| Reverse outer | tcatcagaaatatgcacgcata | 29 |
| Forward inner | agatctgcgattttaaaaaactaact | 30 |
| Reverse inner | ttgatgatttctacaaggacaagg | 31 |
| rs3824068 | | |
| Forward | cattaacaagagcccagga | 32 |
| Reverse | ccatgagagcacacaccta | 33 |
| Pyrosequencing ™ | cagtgcctgtcttgc | 34 |
| rs2361688 | | |
| Forward | tgcacctaccctaccaaagcca | 35 |
| Reverse | tgtggatctccttggaggccct | 36 |
| rs3824067 | | |
| Forward outer | ctccaaggagatccacattcctctt | 37 |
| Reverse outer | gggtcgctgtaaggcttctaggac | 38 |
| Forward inner | cgagatgctccctaaagcccaa | 39 |
| Reverse inner | ggtttcaatttgtgcggtgattcaa | 40 |
| rs1861972 | | |
| Forward | catacaccgcacaaattgaaac | 41 |
| Reverse | gattcagacttatgaacctgacctg | 42 |
| Pyrosequencing ™ | caccactccctgcca | 43 |

TABLE 5-continued

| SNP Primers | Sequence | SEQ ID NO: |
|---|---|---|
| rs1861973 | | |
| Forward | catacaccgcacaaattgaaac | 41 |
| Reverse | gattcagacttatgaacctgacctg | 42 |
| Pyrosequencing ™ | ccttacagcgaccct | 44 |
| ss38341503 | | |
| Forward | cctctgctctcctccctct | 45 |
| Reverse | ggcctggttttcctagtcc | 46 |
| Luminex ™ C | ccctcctgtcctcagggcc | 47 |
| Luminex ™ T | ccctcctgtcctcagggct | 48 |
| Luminex ™ common | cacctgccctgattcccac | 49 |
| rs3808332 | | |
| Forward outer | gcccttggctgggagtcataga | 50 |
| Reverse outer | gggactatggggcaggcctagt | 51 |
| Forward inner | tttcccagtcttctctcctccacc | 52 |
| Reverse inner | gcggtaggtgctgagagcga | 53 |
| rs3808331 | | |
| Forward outer | agtcttctctcctccctctct | 54 |
| Reverse outer | gaggactgcgtgtgatgtaagt | 55 |
| Forward inner | gaaagtgtggggagttttgatt | 56 |
| Reverse inner | tctagataaaagtaaaactcctggat | 57 |
| rs4717034 | | |
| Forward outer | ccgccatccctgttcctgaaca | 58 |
| Reverse outer | gtgtgccacccaataggcaccg | 59 |
| Forward inner | ccctcaccaagtggtggaggtcagt | 60 |
| Reverse inner | gactgggcatgggctcaccg | 61 |
| rs3808329 | | |
| Forward | gtttgtgttggcttggtgag | 62 |
| Reverse | ccctctacagagccttctgc | 63 |
| Luminex ™ G | cctctcctcaccctcctgcg | 64 |
| Luminex ™ A | cctctcctcaccctcctgca | 65 |
| Luminex ™ common | ctaactccctcctccttctcc | 66 |

For rs6460013, rs7794177, rs1264067, rs3808332, rs3808331, rs4717034, tetra-primer ARMS-PCR was conducted in a 10 µl reaction using 1 pmol for each of the inner primers and 0.1 pmol for each of the outer primers, 0.2 5 mM dNTP, 1.5 mM MgCl$_2$, 25 mM KCl, 10 mM Tris-HCl (pH 8.3 for rs6460013, rs7794177, rs1264067; pH 8.8 for rs3808332, rs4717034 and pH 9.2 for rs3808331). For rs1264067, the same conditions were used except for 3.5 mM MgCl$_2$. For rs6150410, the same conditions were used as for rs1264067 with the following exceptions: 0.4 µM of each primer and 10 mM Tris-HCl (pH 8.8). Standard cycling conditions were used: 1 cycle of 94° C. for 4 minutes; 35 cycles of 94° C. for 30 seconds, T$_m$° C. for 30 seconds, 74° C. for 30 seconds; and 1 cycle of 74° C. for 10 minutes (T$_m$ 50° C. for rs1264067, T$_m$ 55° C. for rs6460013, rs7794177, T$_m$ 56° C. for rs3808331, T$_m$ 59° C. for rs6150410; T$_m$ 62° C. for rs3808332, rs4717034).

Rs1345514, rs3824068, rs1861972 and rs1861973 were genotyped using a PYROSEQUENCING™ assay. PCR was conducted in a 20 µl reaction using 0.25 mM dNTP, 1.875 mM MgCl$_2$, 6.25 mM KCl, 1.25 mM Tris-HCl (pH 9.0), 0.1% TRITON™ X-100, 0.05 µM of each primer for rs1861972, rs1861973 and 0.075 µM of each primer for rs3824068. For rs1345514, the same PCR conditions as rs1861972 were used except 0.025 µM of each primer, 0.01 mM dATP, dCTP, dTTP, 2.5 µM dGTP and 7.5 µM 7-deaza- 2'-deoxyguanosine triphosphate, 1.25 mM MgCl$_2$. Standard cycling conditions were as follows: 1 cycle of 94° C. for 4 minutes; 40 cycles of 94° C. for 30 seconds, T$_m$° C. for 30 seconds, 74° C. for 30 seconds; and 1 cycle of 74° C. for 10 minutes (T$_m$ 60° C. for rs3824068, rs1861972 and rs1861973; T$_m$ 62° C. for rs3808332 and rs4717034).

For SNPs genotyped using LUMINEX™ 100 flow cytometry platform (rs3808329, rs3735652, and ss38341503), PCR was conducted in a 20 µl reaction using 0.4 µM of each primer. 0.125 mM dNTP, 1.875 mM MgCl$_2$, 31.25 mM KCl and 12.5 mM Tris-HCl (pH 8.8 for rs3808329 and 8.3 for ss38341503) were used for rs3808329 and ss38341503. For rs3735652, 1.25 mM MgCl$_2$, 1.25 mM Tris-HCl (pH 9.0), 6.25 mM KCl, 0.1% TRITON™ X-100, 0.01 mM dATP, dCTP, dTTP, 2.5 µM dGTP and 7.5 µM 7-deaza-2'-deoxyguanosine triphosphate were used. Standard cycling conditions were used: 1 cycle at 94° C. for 4 minutes; 35 cycles of 94° C. for 30 seconds, T$_m$° C. for 30 seconds, 74° C. for 40 seconds; and 1 cycle of 74° C. for 10 minutes (T$_m$ 66.3° C. for rs3808329, T$_m$ 58° C. for rs3735652, T$_m$ 57° C. for ss38341503).

Rs2361688 and PvuII were genotyped using an RFLP assay. PCR was conducted in 10 µl reaction using 0.1 µM of each primer, 0.25 mM dNTP. For rs2361688, 10 mM Tris-HCl (pH 9.2), 1.5 mM MgCl$_2$, 25 mM KCl were used. For PvuII, 1 mM Tris-HCl (pH 9.2), 5 mM KCl, 0.1% TRITON™ X-100, 1.25 mM MgCl$_2$ were used. Cycling conditions were as follows: 1 cycle of 94° C. for 4 minutes; 35 cycles of 94° C. for 30 seconds, T$_m$° C. for 30 seconds, 74° C. for 30 seconds; and 1 cycle of 74° C. for 10 minutes (T$_m$ 64° C. for rs2361688, T$_m$ 61° C. for PvuII.

Statistical analysis. Prior to data analysis, each polymorphism was assessed for deviations from Hardy-Weinberg equilibrium using genotype data from all parents and standard formulae. The DNA from the MZ twins was used as a genotyping internal control, with complete genotypic concordance observed for all MZ cotwins. Genotypes were checked for Mendelian inconsistencies using the PEDCHECK program version 1.1 (O'Connell and Weeks (1998) Am. J. Hum. Genet. 63: 259-266) and all identified Mendelian errors were corrected by re-genotyping individual samples. In the AGRE I dataset, missing genotyping data was present for 9 individuals for four markers. Since recombination events were not expected at a high frequency given the small (<8 kb) inter-marker distances, haplotype inconsistencies were identified by the SIMWALK program version 2.86 (Weeks and Lathrop (1995) Trends Genet. 11: 513-519). For each of the 14 polymorphisms genotyped in the AGRE I dataset, three marker haplotype analysis with rs1861972 and rs1861973 was performed. Regenotyping of flagged polymorphisms identified only 155 of the 10360 genotypes (1.5%) that could not be resolved. These genotypes were distributed between the 14 polymorphisms, ranging from 45 genotypes for rs1345514 to 7 genotypes for rs3824068. For rs1861972 and rs1861973 genotyped in the AGRE II and NIMH datasets, two SNP haplotype analyses identified only 12 of the 1741 genotypes (0.7%) that could not be resolved upon re-genotyping. The linkage disequilibrium (LD) coefficient (D') for the 18 different polymorphisms was calculated in the AGRE I dataset using the parental genotypes and the GOLD (version 1.0) program (Abecasis and Cookson (2000) Bioinformatics 16:182-3).

All single and multi-locus association analyses were performed using the program PDTPHASE (version 2.404) which also calculates the corresponding P-values. Both haplotype-specific P-values and global P-values (with adjustments for all possible common haplotypes with a frequency greater than 5%) were calculated by the PDTPHASE program. PDTPHASE is a component of the UNPHASED package of association analysis programs (Dudbridge (2003) Genetic Epidim. 25:115-121). PDTPHASE is a modification of the pedigree-based transmission disequilibrium test PDT (Martin, et al. (2000) Am. J. Hum. Genet. 67: 146-154). PDTPHASE like PDT was designed to allow the use of data from related triads and disease discordant sibships from extended pedigrees when testing for transmission disequilibrium. It determines the presence of association by testing for unequal transmission of either allele from parents to affected offspring and/or unequal sharing of either allele between discordant sibships. Informative extended pedigrees contain at least one informative triad (i.e., an affected child with at least one parent heterozygous at the marker) and/or discordant sibship (i.e., at least one affected and one unaffected sibling with different marker genotypes). PDTPHASE has a number of advantages over PDT that increase the statistical power of the analysis. It can handle missing parental data, is able to perform multilocus analysis and includes an EM algorithm that calculates maximum-likelihood gametic frequencies under the null hypothesis, allowing the inclusion of phase uncertain haplotypes.

The total number of families, triads and Discordant Sib Pairs (DSPs) used for the rs1861972 and rs1861973 replication analyses in the AGRE II and NIMH datasets as well as the extension of the LD map in the original AGRE I dataset is listed in Table 6.

TABLE 6

| Dataset | Diagnosis | Familiesc | Triads[c] | DSPs[c] | Subjects |
|---|---|---|---|---|---|
| AGRE I[a] | Narrow | 166 | 262 | 134 | 689 |
|  | Broad | 167 | 322 | 168 | 750 |
| AGRE II[b] | Narrow | 211 | 342 | 225 | 1033 |
|  | Broad | 222 | 434 | 269 | 1071 |
| NIMH | Narrow | 127 | 228 | 71 | 501 |
|  | Broad | 129 | 237 | 73 | 515 |

[a]The 167 AGRE I families of Example 1.
[b]222 additional AGRE families.
[c]Number of families, Triads and discordant sibpairs (DSPs) as calculated by PDT (Martin, et al. (2000) supra).

In all the haplotype analyses, haplotypes with a frequency<5% were pooled for analysis. PDTPHASE, like PDT, can calculate two global scores: the PDT$^{sum}$ (which sums the level of significance from all families) and the PDT$^{ave}$ (which gives equal weight to all families in a data set). Since most families in this study had similar size and structure, and it was observed that the $\chi^2$ distribution and P-values were similar for both PDT scores, only PDT$^{sum}$ were reported herein.

Using a multiplicative model, haplotype relative risk for the rs1861972-rs1861973 A-C haplotype was estimated as the transmission ratio (Transmitted/Untransmitted—T/U) (Altshuler, et al. (2000) Nat. Genet. 26:76-80) from heterozygous parents to a single affected offspring that was selected randomly from each of the 532 families. TRANSMIT (version 2.5.4) was used for this analysis because it is capable of selecting at random a single affected offspring per family for association analysis. From the output, the number of informative transmissions (i.e., from heterozygous parents) may be derived (see Example 1) and the transmission ratio estimated. This analysis was repeated 20 times each for the narrow and broad diagnosis and mean relative risk was estimated under each diagnosis. The relative risk and haplotype frequency for the A-C haplotype were then used to estimate the population attributable risk (PAR) using the following standard formula: PAR=(X−1)/X; where X=(1−f)$^2$+2f(1−f)γ+f$^2$γ$^2$ and γ=haplotype relative risk.

Sequence Analysis. Four overlapping PCR products of the EN2 intron were PCR amplified from 20 ASD-affected individuals who inherited the rs1861972-rs1861973 A-C haplotype from heterozygous parents. Each PCR product was then purified (QIAGEN®-QLAQUICK® PCR Purification Kit) and sequenced on an ABI 3730 DNA analyzer. The sequence was then analyzed for DNA alterations using CODONCODE ALIGNER®. The primer sequences are listed in Table 7 and PCR conditions employed are as follows.

PCR for amplification of PCR product 1 was conducted in a 50 µl reaction using 2 mM MgCl$_2$, 5 mM KCl, 1 mM Tris-HCl (pH 9.2), 0.1% TRITON™ X-100, 2 µl of GC melt (BD Biosciences), 5% Dimethyl Sulfoxide (Sigma), 0.4 µM of each primer, 8 µM dATP, dCTP, dTTP, 2 µM dGTP and 6 µM 7-deaza-2'-deoxyguanosine triphosphate. Standard cycling conditions were used: 1 cycle of 94° C. for 1 minute; 35 cycles of 94° C. for 40 seconds, 59° C. for 30 seconds, 68° C. for 3 minutes 30 seconds; and 1 cycle of 68° C. for 3 minutes. For PCR products 2, 3, and 4, PCR was conducted in a 20 µl reaction using 0.625 mM MgCl$_2$, 5 mM KCl, 1 mM Tris-HCl (pH 9.2), 0.1% TRITON™ X-100, 0.25 mM dNTPs, 0.5 ng/µl of each primer. Standard cycling conditions for PCR products 2, 3, and 4 were used: 1 cycle of 94° C. for 5 minutes; 35 cycles of 94° C. for 30 seconds, T$_m$° C. for 30 seconds, 74° C. for 60 seconds; and 1 cycle of 74° C. for 10 minutes (where T$_m$ 60° C. for PCR product 2 and 4, T$_m$ 62° C. for PCR product 3).

TABLE 7

| Primer | Sequence | SEQ ID NO: |
|---|---|---|
| PCR Product 1 | | |
| Forward | ctg tcg gtg agc tcg gac tcg g | 67 |
| Reverse | gcc ctg cag aga tgc tgg ata tat | 68 |
| PCR Product 2 | | |
| Forward | tag aaa gga cct tct ctc agg g | 69 |
| Reverse | gtg gtt gga aac cca gac aga gat | 70 |
| PCR Product 3 | | |
| Forward | cat taa caa gag ccc cag gac cag aag | 71 |
| Reverse | gac aag gtc agc tgg gct ac | 72 |
| PCR Product 4 | | |
| Forward | ttc ccc atg gat agc agg tcc tag | 73 |
| Reverse | ggt ctc gaa aac caa aga aga aga acc cga | 74 |

En2 Expression Constructs. To misexpress the En2 protein, total RNA was isolated from adult C57BL6/J mouse cerebellum, a 1012-bp PCR product that included the En2 protein coding sequence was amplified by RT-PCR (SUPERSCRIPT™ RT) and subcloned 3' of a CMV protein/enhancer. PCR was conducted in a 25 µl reaction of 0.4 µM of each primer, 0.25 mM dNTP, 1.5 mM MgCl$_2$, 25 mM KCl, 10 mM Tris-HCl pH 8.3 and cycling conditions of 1 cycle of 94° C. for 4 minutes; 35 cycles of 94° C. for 45 seconds, 61° C. for 1 minute, 74° C. for 2 minutes; and 1 cycle of 74° C. for 10 minutes were used. The primer sequences were: Forward, 5'-GTG AAG TAT GGA GGA GAA GG-3' (SEQ ID NO:75); Reverse, 5'-CTA AAC AGT CCC CTT TGC AG-3' (SEQ ID NO:76). The PCR product was isolated by 0.8% agarose gel electrophoresis, purified and cloned into the pCR2.1® vector (INVITROGEN™. EcoRI restriction enzyme digestion was used to clone the En2 cDNA into the pCMS-EGFP expression vector (CLONTECH™)

Cell Culture and cDNA Transfections. Time-mated pregnant Sprague Dawley rats were obtained from Hilltop Labs (Philadelphia, Pa.). At embryonic day 14.5 (E14.5), embryonic skull and meninges were removed and dorsolateral cerebral cortex was dissected, mechanically dissociated, and plated at 4×10$^5$ cells on poly-D-lysine (0.1 mg/mL) and laminin (20 µg/mL)-coated 25-mm glass coverslips (VWR) in defined medium according to established methods (Nicot and DiCicco-Bloom (2001) Proc. Natl. Acad. Sci. USA 98(8): 4758-63). Culture medium consisted of NEUROBASAL™ (GIBCO-BRL®) supplemented with 2% B27, and contained glutamine (2 mM), penicillin (50 U/ml), streptomycin (50 µg/ml), bovine serum albumin (1 mg/ml), and basic fibroblast growth factor (10 ng/ml). Unless stated otherwise, components were obtained from Sigma (St. Louis, Mo.). Cultures were maintained in a humidified 5% CO$_2$/air incubator at 37° C.

After 24 hours in culture, cells were transfected using LIPOFECTAMINE™ Plus Reagent (GIBCO-BRL®) for 5 hours containing one of the following: 1) the mouse En2 EGFP-expression plasmid which codes for a full-length En2 protein with 93% nucleotide identity with rat En2, 2) pCMS-EGFP with En2 cloned in the non-protein coding, reverse orientation (REn2), or 3) pCMS-EGFP alone. After an additional day of incubation, cells were fixed with 4% paraformaldehyde and assessed using phase and fluorescence microscopy.

En2 RT-PCR Expression Analysis. Total RNA was isolated from freshly dissected E14.5 rat cortices and hindbrains, and the expression of En2 was determined by PCR amplification of a 220-bp 3'-UTR PCR product in a 25 µl reaction, using 0.4 µM of each primer, 0.25 mM dNTP, 1.5 mM MgCl$_2$, 25 mM KCl, 10 mM Tris-HCl pH 8.3 and cycling conditions of 1 cycle of 94° C. for 4 minutes; 35 cycles of 94° C. for 45 seconds, 56° C. for 1 minute, 74° C. for 90 seconds; and 1 cycle of 74° C. for 10 minutes. The primer sequences were: Forward, 5'-AAC CGT GAA CAA AAG GCC AGT G-3' (SEQ ID NO:77), Reverse: 5'-CTA AAC AGT CCC CTT TGC AG-3' (SEQ ID NO:76).

Immunocytochemistry. Immunocytochemistry was performed according to established methods (Nicot and DiCicco-Bloom (2001) supra). The following dilutions of primary and secondary antibodies were used: polyclonal chicken anti-GFP (1:8000; Chemicon), polyclonal goat anti-En2 (1:500; Santa Cruz), mouse Tun. (1:1500; COVANCE®), ALEXA FLUOR® 488-conjugated rabbit anti-chicken IgG (1:800; Chemicon) and ALEXA FLUORO 594-conjugated rabbit anti-goat or goat anti-mouse IgG (1:1000; Vector).

Results. For the AGRE II dataset, significant (P<0.05) evidence of association for the A allele of rs1861972 was observed under the broad diagnosis while a trend towards association was observed under the narrow diagnosis (Table 8). For rs1861973, significant association of the C allele was observed under both diagnostic criteria (Table 8). Analysis of rs1861972-rs1861973 haplotypes demonstrated that the A-C haplotype was significantly over-transmitted to affected offspring under both diagnostic criteria (Table 9) while the A-T, G-C and G-T haplotypes were all under-transmitted. Global $\chi^2$ tests for all haplotypes yielded significant P-values (narrow: P=0.0048; broad: P=0.0016) (Table 9) that were similar to those of the AGRE I dataset presented in Example 1. Thus, replication of the association results for the same alleles of rs1861972 and rs1861973 with ASD was observed in this second AGRE dataset.

TABLE 8

| Dataset | SNP[c] | Diagnosis | Parental Transmissions[d] | | DSPs[e] | | $\chi^{2}$[f] | P-value[g] |
|---|---|---|---|---|---|---|---|---|
| | | | T | U | A | UA | | |
| AGRE I[a] | rs1861972 | narrow | 383 | 354 | 202 | 185 | 4.991 | 0.0255 |
| | | broad | 467 | 436 | 253 | 226 | 5.861 | 0.0155 |
| | rs1861973 | narrow | 373 | 338 | 199 | 183 | 6.936 | 0.0084 |
| | | broad | 449 | 415 | 242 | 220 | 6.297 | 0.0121 |
| AGRE II[b] | rs1861972 | narrow | 438 | 408 | 314 | 297 | 2.997 | 0.0834 |
| | | broad | 555 | 513 | 381 | 359 | 4.73 | 0.0296 |
| | rs1861973 | narrow | 433 | 395 | 308 | 285 | 4.903 | 0.0268 |
| | | broad | 546 | 500 | 375 | 346 | 6.299 | 0.0121 |
| NIMH | rs1861972 | narrow | 222 | 200 | 113 | 107 | 4.000 | 0.0455 |
| | | broad | 228 | 206 | 115 | 109 | 3.843 | 0.0500 |
| | rs1861973 | narrow | 227 | 203 | 111 | 104 | 5.139 | 0.0234 |
| | | broad | 234 | 209 | 113 | 105 | 5.585 | 0.0181 |

[a]The 167 AGRE families of Example 1.
[b]The additional 222 AGRE families.
[c]The MAF for rs1861972 was 0.269 and 0.317 in the AGRE II and NIMH datasets, respectively. For rs1861973, the MAF was 0.279 and 0.295, respectively.
[d]T = number of times common allele transmitted; U = number of times common allele not transmitted from parents to affected offspring.
[e]Discordant sibpair counts: A = total number of the common allele in affected siblings; UA = total number of the common allele in unaffected siblings of DSPs.
[f](Global $\chi 2$ values calculated by PDTPHASEsum (Dudbridge (2003) supra).
[g]P-value generated by PDTPHASEsum (1df). Bolded P-values represent significant (P < 0.05) association.

Since identical criteria have been used to obtain all the AGRE pedigrees, the AGRE I and AGRE II datasets were combined and association of rs1816972 and rs1861973 with ASD was re-analyzed. Smaller P-values were observed than in either dataset alone (haplotype—narrow: P=0.0000067; broad: P=0.0000033), indicating that the same alleles are associated with ASD in both datasets.

Association of rs1861972 and rs1861973 was then tested in the NIMH dataset. Statistically significant association was obtained for both SNPs individually (Table 8) and as a haplotype (Table 9).

TABLE 9

| Dataset | Haplotype[c] | Diagnosis | Parental Transmissions[d] | | DSPs[e] | | Freq. | $\chi^{2}$[f] | P-value[g] |
|---|---|---|---|---|---|---|---|---|---|
| | | | T | U | A | UA | | | |
| AGRE I[a] | A-C | narrow | 369 | 323 | 195 | 179 | 0.732 | | 0.0024 |
| | A-T | | 8 | 25 | 5 | 4 | 0.014 | | — |
| | G-C | | 4 | 15 | 4 | 4 | 0.006 | | — |
| | G-T | | 111 | 129 | 52 | 69 | 0.247 | | 0.0714 |
| | global | | | | | | | 14 | 0.0009 |
| | A-C | broad | 444 | 399 | 238 | 216 | 0.734 | | 0.0039 |
| | A-T | | 11 | 28 | 5 | 4 | 0.016 | | — |
| | G-C | | 5 | 16 | 4 | 4 | 0.007 | | — |
| | G-T | | 140 | 157 | 69 | 92 | 0.243 | | 0.0765 |
| | global | | | | | | | 13 | 0.0017 |
| AGRE II[b] | A-C | narrow | 429 | 386 | 308 | 285 | 0.713 | | 0.0168 |
| | A-T | | 4 | 16 | 2 | 5 | 0.017 | | — |
| | G-C | | 2 | 8 | 0 | 0 | 0.007 | | — |
| | G-T | | 161 | 186 | 128 | 148 | 0.263 | | 0.0928 |
| | global | | | | | | | 11 | 0.0048 |
| | A-C | broad | 540 | 487 | 375 | 346 | 0.721 | | 0.0061 |
| | A-T | | 6 | 18 | 2 | 6 | 0.014 | | — |
| | G-C | | 2 | 11 | 0 | 0 | 0.006 | | — |
| | G-T | | 210 | 242 | 149 | 174 | 0.259 | | 0.0493 |
| | global | | | | | | | 13 | 0.0016 |
| NIMH | A-C | narrow | 221 | 198 | 111 | 104 | 0.676 | | 0.0321 |
| | A-T | | 1 | 2 | 0 | 1 | 0.007 | | — |
| | G-C | | 6 | 5 | 0 | 0 | 0.025 | | — |
| | G-T | | 78 | 101 | 27 | 34 | 0.292 | | 0.0329 |
| | global | | | | | | | 6.1 | 0.0463 |
| | A-C | broad | 227 | 204 | 113 | 105 | 0.672 | | 0.0312 |
| | A-T | | 1 | 2 | 0 | 2 | 0.008 | | — |
| | G-C | | 7 | 5 | 0 | 0 | 0.023 | | — |

TABLE 9-continued

| Dataset | Haplotype[c] | Diagnosis | Parental Transmissions[d] | | DSPs[e] | | Freq. | $\chi^2$[f] | P-value[g] |
|---|---|---|---|---|---|---|---|---|---|
| | | | T | U | A | UA | | | |
| | G-T | | 81 | 105 | 29 | 35 | 0.296 | | 0.0295 |
| | global | | | | | | | 6.3 | 0.0431 |

[a]The 167 initial AGRE families of Example 1.
[b]The additional 222 AGRE II families.
[c]The frequency of the A-C haplotype was 0.715 and 0.680 in the AGRE II and NIMH datasets, respectively.
[d]T = number of times test haplotype transmitted; U = number of times test haplotype not transmitted from parents to affected offspring.
[e]Discordant sibpair counts: A = total number of the test haplotype in affected siblings; UA = total number of the test haplotype in unaffected siblings of DSPs.
[f]Global $\chi^2$ values calculated by PDTPHASE[sum] (Dudbridge (2003) supra), restricted to common haplotypes with frequency greater than 5%.
[g]P-value generated by PDTPHASE[sum] (1df for single haplotype and 2df for the global tests). Bolded P-values represent significant (P < 0.05) association.

When the NIMH dataset was combined with both AGRE datasets and re-analyzed for association, further reduction of the P-values was obtained (rs1861972-rs1861973 haplotype-narrow: P=0.00000065; broad: P=0.00000035). These data represent one of the most significant associations for any gene with ASD. Given the large sample size (518 families), these results indicate an inherited variation in EN2 in susceptibility to ASD.

Since a P-value is not a measure of effect size, this large combined sample of 518 families was used to estimate the relative risk and the associated population attributable risk (PAR) under a multiplicative model for the A-C haplotype. The haplotype relative risk was estimated as approximately 1.42 and 1.40 under the narrow and broad diagnosis, respectively. Although this represents a relatively modest increase in individual risk, given the high frequency of this common haplotype (~67% in the combined sample), a relative risk of 1.42 and 1.40 corresponds to a large PAR of approximately 39.5% and 38% for the narrow and broad diagnosis of ASD, respectively. These data indicate that as many as 40% of the ASD cases in the population were influenced by variation in EN2 gene.

The data presented in Example 1 demonstrated that rs1861972 and rs1861973 were in strong LD with each other. Similar results were obtained in both the AGRE II an NIMH datasets (AGRE II: D'=0.967; NIMH: D'=0.977). In addition, the allele frequencies for rs1861972 and rs1861973 in both the AGRE II an NIMH datasets were almost identical to each other and to what was found for the AGRE I dataset of Example 1 (Table 10). This together with the association results obtained in the AGRE II and NIMH samples indicates that they are likely to be derived from the same population and therefore share a similar LD relationship with the etiological variant.

TABLE 10

| SNP | Location | Polymorphism[a] | Freq.[b] | Assay Type[c] |
|---|---|---|---|---|
| rs6150410 | Promoter | CGCATCCCC/— | 0.334 | PCR/gel electrophor. |
| PvuII | Promoter | GC/— | 0.469 | RFLP |
| rs1345514 | Promoter | C/T | 0.340 | Pyrosequencing ™ |
| rs3735653 | Exon 1 | C/T | 0.486 | Pyrosequencing ™ |
| rs3735652 | Intron | G/C | 0.402 | Luminex ™ |
| rs6460013 | Intron | G/T | 0.054 | Tetra-Primer ARMS |
| rs7794177 | Intron | C/G | 0.077 | Tetra-Primer ARMS |
| rs3824068 | Intron | C/T | 0.386 | Pyrosequencing ™ |
| rs2361688 | Intron | A/G | 0.271 | RFLP |
| rs3824067 | Intron | T/A | 0.181 | Tetra-Primer ARMS |
| rs1861972 | Intron | A/G | 0.281 | Pyrosequencing ™ |
| rs1861973 | Intron | C/T | 0.287 | Pyrosequencing ™ |
| ss38341503 | Intron | C/T | 0.010 | Luminex ™ |
| rs3808332 | Intron | T/C | 0.192 | Tetra-Primer ARMS |
| rs3808331 | Intron | T/C | 0.063 | Tetra-Primer ARMS |
| rs4717034 | Intron | C/T | 0.175 | Tetra-Primer ARMS |
| rs2361689 | Exon 2 | T/C | 0.322 | Pyrosequencing ™ |
| rs3808329 | 3' UTR | A/T | 0.130 | Luminex ™ |

[a]Second allele is rare allele.
[b]Frequency of rare allele in AGRE I dataset.
[c]PYROSEQUENCING ™ (Ronaghi, et al. (1998) supra; Ahmadian, et al. (2000) supra), Tetra-primer ARMS (Ye, et al. (2001) supra), LUMINEX ™ (Iannone, et al. (2000) supra).

Analysis of the ACRE I dataset indicated that rs1861972 and rs1861973 were non-functional polymorphisms in LD with a risk allele(s) located elsewhere in the gene. To identify this risk allele, the LD map was extended in the original AGRE I dataset. This dataset was selected for LD mapping because it displayed the most significant association for rs1861972 and rs1861973, both individually and as a haplotype, and therefore represented a minimal cost-effective sample set with sufficient power to detect the putative risk allele. Fourteen additional polymorphisms (3 in the promoter, 10 in the intron and 1 in the 3'UTR) were tested for association with ASD, giving a total of 18 markers typed across the entire gene. Thirteen of these newly typed polymorphisms were identified through dbSNP, while one, ss38341503, was identified by resequencing the entire intron in 20 individuals with ASD who inherited the rs1861972-rs1861973 A-C haplotype from heterozygous parents. The location, DNA change and minor allele frequency (MAF) of each polymorphism are presented in Table 10.

In the absence of knowledge about the exact mode of inheritance at this locus, a risk allele(s) responsible for rs1861972 and rs1861973 association was expected to exhibit the following inheritance pattern. The polymorphism(s) should display strong LD (D'>0.70) with both rs1861972 and rs1861973 and therefore, was expected to have a similar frequency as the A-C haplotype. Further, individually the polymorphism(s) should also be associated with ASD. If a single polymorphism was responsible for the association of rs1861972 and rs1861973, then this polymorphism should demonstrate at least as significant association as the A-C haplotype under both the narrow and broad diagnosis. However, if multiple alleles were working in concert and a simple additive model is assumed, then each of these polymorphisms should display association with ASD individually because they will be in strong LD with rs1861972 and rs1861973 but their statistical significance might not be as great as when they are analyzed as a haplotype. Moreover, in multi-SNP haplotype analysis for a single locus model, the associated allele in conjunction with the A-C haplotype should display at least as significant association as the A-C haplotype alone. In a multi-locus model, only the haplotypes with all or most of the risk alleles would display the greatest statistical significance.

When the 14 additional polymorphisms were tested for association in the AGRE I dataset, 12 displayed no evidence for association under both the narrow and broad diagnosis (Table 11).

TABLE 11

| Polymorphism | Diagnosis | Parental Transmissions[a] | | DSPs[b] | | $\chi^2$[c] | P-value[d] |
|---|---|---|---|---|---|---|---|
| | | T | U | A | UA | | |
| rs6150410 | narrow | 317 | 317 | 183 | 189 | 0.081 | 0.776 |
| | broad | 394 | 384 | 234 | 239 | 0.043 | 0.835 |
| PvuII | narrow | 253 | 249 | 127 | 131 | 0.000 | 1.000 |
| | broad | 306 | 303 | 163 | 162 | 0.025 | 0.875 |
| rs1345514 | narrow | 271 | 278 | 165 | 168 | 0.220 | 0.639 |
| | broad | 332 | 331 | 211 | 215 | 0.015 | 0.902 |
| rs3735652 | narrow | 274 | 291 | 156 | 168 | 1.532 | 0.216 |
| | broad | 350 | 357 | 203 | 220 | 0.867 | 0.352 |
| rs6460013 | narrow | 467 | 466 | 249 | 246 | 0.364 | 0.546 |
| | broad | 568 | 569 | 314 | 309 | 0.381 | 0.537 |
| rs7794177 | narrow | 425 | 414 | 239 | 237 | 1.374 | 0.241 |
| | broad | 519 | 509 | 295 | 299 | 0.237 | 0.626 |
| rs3824068 | narrow | 280 | 316 | 156 | 166 | 4.372 | 0.036 |
| | broad | 355 | 384 | 205 | 215 | 2.664 | 0.103 |
| rs2361688 | narrow | 347 | 328 | 193 | 183 | 2.317 | 0.128 |
| | broad | 423 | 394 | 243 | 224 | 4.208 | 0.040 |
| rs3824067 | narrow | 370 | 357 | 213 | 214 | 0.581 | 0.446 |
| | broad | 443 | 438 | 263 | 267 | 0.003 | 0.959 |
| ss38341503 | narrow | 464 | 458 | 266 | 265 | 1.581 | 0.209 |
| | broad | 565 | 559 | 334 | 332 | 1.684 | 0.194 |
| rs3808332 | narrow | 361 | 361 | 208 | 208 | 0.000 | 1.000 |
| | broad | 433 | 440 | 260 | 261 | 0.173 | 0.677 |
| rs3808331 | narrow | 421 | 417 | 243 | 245 | 0.040 | 0.841 |
| | broad | 519 | 510 | 309 | 310 | 0.525 | 0.469 |
| rs4717034 | narrow | 365 | 362 | 205 | 212 | 0.056 | 0.812 |
| | broad | 436 | 444 | 257 | 267 | 0.802 | 0.37 |
| rs3808329 | narrow | 424 | 405 | 229 | 243 | 0.108 | 0.742 |
| | broad | 516 | 491 | 289 | 303 | 0.434 | 0.510 |

[a]T = number of times common allele transmitted; U = number of times common allele not transmitted from parents to affected offspring.
[b]Discordant sibpair counts: A = total number of the common allele in affected siblings; UA = total number of the common allele in unaffected siblings of DSPs.
[c]Global $\chi^2$ values calculated by PDTPHASEsum (Dudbridge (2003) supra).
[d]Bolded P-values represent significant (P < 0.05) association.

Two intronic SNPs, rs3824068 and rs2361688, displayed minimally significant association but only under one diagnosis (Table 11). To investigate whether rs3824068 and rs2361688 could be functioning in a multi-locus manner, 3 and 4 marker haplotype analysis with the rs1861972-rs1861973 A-C haplotype was performed. For the rs3824068-rs2361688-rs1861972-rs1861973 and the rs3824068-rs1861972-rs1816973 haplotype analysis, all common core A-C haplotypes (frequency>5%) displayed no association with the exception of the T-A-C rs3824068-rs1861972-rs1816973 haplotype that displayed minimal association under one diagnosis (Tables 6 and 8).

For the rs2361688-rs1861972-rs1861973 analysis, the G-A-C haplotype displayed similar statistical significance as the A-C haplotype under the broad diagnosis but under the narrow diagnosis the effect was diluted. Four other common 3 marker A-C haplotypes (G-A-C rs6460013-rs1861972-rs1861973, C-A-C rs7794177-rs1861972-rs1861973, A-C—C rs1861972-rs1861973-ss38341503 and A-C-A rs1861972-rs1861973-rs3808329) displayed similar statistically significant association as the A-C haplotype under at least one diagnosis. However, rs6460013, rs7794177, ss38341503 and rs3808329 were not associated individually with ASD, indicating that these polymorphisms were not functioning as risk alleles according to the criteria herein.

The inter-marker LD relationships for these 14 polymorphisms plus the 4 previously tested SNPs were then examined. All promoter, exonic and 3'-UTR polymorphisms displayed weak or intermediate LD (D': 0.024-0.632) respectively with both rs1861972 and rs1861973, providing an explanation why they were not associated with ASD (Table 12). However, all new intronic SNPs displayed strong LD (D':0.720-1.00) with both rs1861972 and rs1861973 (Table 12). The lack of association with ASD observed for 8 of the intronic SNPs indicates that these intronic variants were in weaker LD with the risk allele than rs1861872 or rs1861973. This reduced power to detect LD may be due to differences in allele frequencies and may reflect the genetic history of when these intronic alleles arose in relation to the risk allele. Evidence for some association of rs2361688 and rs3824068 with ASD indicates that these variants are in stronger LD with the risk allele(s) than the other newly genotyped intronic SNPs.

TABLE 12

| | PvuII | rs1345514 | rs3735653 | rs3735652 | rs6460013 |
|---|---|---|---|---|---|
| rs6150410 | 0.952 | 0.934 | 0.668 | 0.497 | 0.818 |
| PvuII | | 0.962 | 0.323 | 0.121 | 0.801 |
| rs1345514 | | | 0.681 | 0.486 | 0.836 |
| rs3735653 | | | | 0.686 | 1.000 |
| rs3735652 | | | | | 0.756 |
| rs6460013 | | | | | |
| rs7794177 | | | | | |
| rs3824068 | | | | | |
| rs2361688 | | | | | |
| rs3824067 | | | | | |
| rs1861972 | | | | | |
| rs1861973 | | | | | |
| ss38341503 | | | | | |
| rs3808332 | | | | | |
| rs3808331 | | | | | |
| rs4717034 | | | | | |
| rs2361689 | | | | | |

| | rs7794177 | rs3824068 | rs2361688 | rs3824067 | rs1861972 |
|---|---|---|---|---|---|
| rs6150410 | 0.070 | 0.479 | 0.205 | 0.935 | 0.106 |
| PvuII | 0.721 | 0.197 | 0.091 | 0.807 | 0.046 |
| rs1345514 | 0.109 | 0.480 | 0.259 | 0.922 | 0.141 |
| rs3735653 | 0.677 | 0.763 | 0.471 | 0.851 | 0.403 |
| rs3735652 | 0.428 | 0.869 | 0.949 | 0.695 | 0.828 |
| rs6460013 | 0.991 | 0.999 | 1.000 | 1.000 | 0.999 |
| rs7794177 | | 0.629 | 0.959 | 0.953 | 1.000 |
| rs3824068 | | | 0.950 | 0.952 | 0.876 |
| rs2361688 | | | | 0.926 | 0.872 |
| rs3824067 | | | | | 0.924 |
| rs1861972 | | | | | |
| rs1861973 | | | | | |
| ss38341503 | | | | | |
| rs3808332 | | | | | |
| rs3808331 | | | | | |
| rs4717034 | | | | | |
| rs2361689 | | | | | |

TABLE 12-continued

| | rs1861973 | ss38341503 | rs3808332 | rs3808331 | rs4717034 |
|---|---|---|---|---|---|
| rs6150410 | 0.057 | 1.000 | 0.936 | 1.000 | 0.867 |
| PvuII | 0.024 | 1.000 | 0.868 | 0.902 | 0.807 |
| rs1345514 | 0.093 | 1.000 | 0.925 | 1.000 | 0.837 |
| rs3735653 | 0.430 | 1.000 | 0.824 | 0.899 | 0.779 |
| rs3735652 | 0.888 | 0.651 | 0.695 | 0.842 | 0.605 |
| rs6460013 | 1.000 | 0.014 | 1.000 | 0.822 | 1.000 |
| rs7794177 | 0.999 | 0.090 | 0.981 | 0.990 | 0.946 |
| rs3824068 | 0.889 | 1.000 | 1.000 | 1.000 | 0.947 |
| rs2361688 | 0.909 | 1.000 | 0.921 | 1.000 | 0.913 |
| rs3824067 | 0.882 | 1.000 | 0.931 | 1.000 | 0.874 |
| rs1861972 | 0.903 | 1.000 | 0.864 | 0.720 | 0.759 |
| rs1861973 | | 1.000 | 0.940 | 1.000 | 0.935 |
| ss38341503 | | | 1.000 | 0.069 | 0.848 |
| rs3808332 | | | | 1.000 | 0.923 |
| rs3808331 | | | | | 1.000 |
| rs4717034 | | | | | |
| rs2361689 | | | | | |

| | rs2361689 | rs3808329 |
|---|---|---|
| rs6150410 | 0.609 | 0.121 |
| PvuII | 0.264 | 0.250 |
| rs1345514 | 0.540 | 0.055 |
| rs3735653 | 0.531 | 0.061 |
| rs3735652 | 0.785 | 0.198 |
| rs6460013 | 1.000 | 0.461 |
| rs7794177 | 0.601 | 0.228 |
| rs3824068 | 0.981 | 0.142 |
| rs2361688 | 0.541 | 0.301 |
| rs3824067 | 0.939 | 0.590 |
| rs1861972 | 0.632 | 0.392 |
| rs1861973 | 0.603 | 0.258 |
| ss38341503 | 1.000 | 0.616 |
| rs3808332 | 0.898 | 0.570 |
| rs3808331 | 0.038 | 0.253 |
| rs4717034 | 0.847 | 0.785 |
| rs2361689 | | 0.037 |

Data represent pairwise linkage disequilibrium (D') in the AGRE I dataset. The LD relationship of each polymorphism with rs1861972 and rs1861973 are outlined with number of lines corresponding to the strength of LD (three lines—strong LD: D' > 0.72; two lines—intermediate/weak LD: D': 0.024-0.632).

One interpretation of the strong LD observed between the intronic SNPs and rs1861972 and rs1861973 as well as the decay of LD for flanking polymorphisms is that the risk allele is situated approximately 3.0 kb in the intron. Sequence analysis of the intron in 20 individuals affected with ASD who inherited the rs1861972-rs1861973 A-C haplotype from heterozygous parents has identified only one novel SNP (ss383341503) with a MAF of 1%, indicating that additional common intronic polymorphisms are unlikely. All intronic SNPs were tested and only rs1861972 and rs1861973 were consistently associated both individually and as a haplotype under both diagnostic criteria. Together this analysis indicates that the A allele of rs1861972 and the C allele of rs1861973 function as risk alleles in cis and the lack of association of some of the core A-C haplotypes identified in the multi-SNP haplotype analysis was due to other unidentified epistatic genetic or environmental interactions. Comparative genomic studies of human, chimp, mouse, rat and dog sequences do not place either SNP within conserved regions. However, computer prediction programs determined that the associated alleles of rs1861972 and rs1861973 were situated within consensus binding sites for the CBP and LvC transcription factors, respectively. For the associated alleles, the match ratio for each transcription factor was 100%. The non-associated alleles alter a conserved nucleotide in the consensus binding site so when the sequence was re-analyzed, the non-associated alleles were predicted to abolish binding of both transcription factors.

Risk alleles of human EN2 associated with ASD may alter the spatial and/or temporal expression of the gene during brain development. To examine the consequences of gene misexpression, En2 EGFP vectors were transfected into cultures of primary neuronal precursors obtained from rat E14.5 cerebral cortex. The expression plasmid alone (pCMS-EGFP) or with En2 cloned in the reverse orientation (REn2) was used as controls. This well-characterized model system has been used to define the effects of extracellular signals and transfected genes on cortical neurogenesis (Lu and DiCicco-Bloom (1997) Proc. Natl. Acad. Sci. USA 94(7):3357-62; Nicot and DiCicco-Bloom (2001) supra; Carey, et al. (2002) J. Neurosci. 22(5):1583-91). En2 was not expressed in E14.5 rat cortical cells as assessed by RT-PCR, thereby defining the effects of En2 misexpression in a naïve cell population. Twenty-four hours after transfection, all three vectors generated similar numbers of EGFP-expressing cells (pCMS-EGFP: 174.5±45.1; REn2: 201±20.4; En2: 163.3±11.9; GFP$^+$ Cells±SEM: P>0.05), as detected by EGFP autofluorescence and immunocytochemistry, indicating that vector expression per se was not deleterious. En2 protein immunoreactivity was detected only in EGFP-positive, En2-transfected cells, but not in REn2- or EGFP-transfected cells.

The effects of vector expression were examined on cortical cell morphology, assessing undifferentiated precursors and mature neurons. Undifferentiated neural precursors appeared as flat cells that sometimes extended processes of variable diameter and length with distal filopodia. Precursors did not express the early marker of neuronal differentiation, cytoskeletal protein βIII-tubulin (TuJ1). Differentiated neurons exhibited a round or pyramidal cell body, extended thin, uniform processes and expressed βIII-tubulin. In cultures transfected with control vectors, approximately equal proportions of cells exhibited morphologies of precursors and neurons, reproducing ratios obtained previously in this model (Nicot and DiCicco-Bloom (2001) supra). In contrast, following En2 transfection, the proportion of undifferentiated precursors increased from 55% in controls to 71% in En2-transfected cells. As overall numbers of cells were similar across conditions, the increase in precursors occurred at the expense of cells exhibiting neuronal morphology: neurons decreased from 45% in controls to only 29% following En2 transfection. The reduction in neuronal differentiation was further verified by assessing βIII-tubulin-expressing cells, which was decreased by 55% in En2 transfected cells (100% in controls, 45% following En2 transfection), indicating that altered cytoskeletal protein expression may underlie changes observed in cellular morphology elicited by En2. These data demonstrate that En2 ectopic expression disrupts neuronal differentiation, indicating that the gene is an important regulator of neuronal development.

In summary, these data indicate that EN2 is involved in ASD susceptibility. Evidence for association was presented for rs1861972 and rs1861973 in the ACRE II and NIMH datasets. PAR estimations using the entire sample of 518 families indicated that the risk allele responsible for rs1861972-rs1861973 association contributed to approximately 40% of ASD cases in the general population. In addition, LD mapping using 18 SNPs distributed across the gene localized the associated genomic region to the intron. Analysis of this region identified associated intronic alleles that could be characterized for functional differences. Further, single and multi-SNP association data indicated that rs1861972, rs1861973 and rs2361688 were candidate risk alleles that function together in cis to increase risk for ASD. Moreover, it was demonstrated that ectopic misexpression of En2 disrupts neuronal development. Together these data indicate that variation within the EN2 gene plays an important role in ASD etiology and a risk allele(s) which causes altered expression of EN2 to perturb neuronal development and contribute to the pathology associated with ASD.

EXAMPLE 3

Expression of EN2

The data presented herein indicate that a DNA variant in EN2 increases autism spectrum disorder risk. LD mapping, re-sequencing and association analysis identified the autism spectrum disorder-associated haplotype as the most likely risk allele.

To provide further evidence that the autism spectrum disorder-associated haplotype contributes to risk, the function of the haplotype was investigated. Because the autism spectrum disorder-associated haplotype maps to the intron, potential regulatory effects were tested. In cultures of primary mouse neurons, luciferase assays demonstrated that the autism spectrum disorder-associated haplotype results in a ~250% increase in gene expression for the A-C haplotype. Additional analysis determined that both associated alleles are sufficient and necessary for activator function, and two transcription factors, Cux1 and NfiB, mediate haplotype function.

Because autism spectrum disorder is a neurodevelopmental disorder, the in vitro analysis was extended to transgenic mice. Quantitative reverse transcription polymerase chain reaction (qRT-PCR) measured transgene levels for 14 mouse lines at five developmental time points (E9.5, E12.5, E17.5, P6 and adult). At all stages A-C haplotype resulted in increased expression (P<0.001). In addition, in situ hybridizations demonstrated expanded expression domains at the midbrain-hindbrain junction (E9.5), cerebellum and colliculi when connections are being generated (E17.5), as well as the locus cereleus and raphe nuclei in the adult.

It was then determined whether EN2 levels are increased in human subjects with autism. Ninety cerebellar samples were acquired. TAQMAN qRT-PCR measured normalized EN2 mRNA levels. A significant increase was observed in affected individuals with an A-C haplotype compared to controls (74% increase, P=0.0005; Type 3 tests of fixed effects). These data indicate EN2 as an autism susceptibility gene and increased levels of EN2 being correlated with autism risk.

Brain function depends upon normal development, which requires the orchestration of cellular events including the proliferation and differentiation of neurons. During normal development, neuroprogenitors divide and at specific times during development these dividing progenitors receive a signal to exit from the cell cycle and differentiate into mature neurons. This balance between proliferation and differentiation is necessary to generate the proper number of neurons in the brain, which is essential for function. Interestingly, one of the most consistent morphological abnormalities associated with autism is macrocephaly where the brain is enlarged (McCaffery & Deutsch (2005) *Prog. Neurobiol.* 77:38-56; van Daalen, et al. (2007) *Pediatr. Neurol.* 37:324-30). This suggests that the balance between proliferation and differentiation may be abnormal in autism.

To determine whether increased levels of EN2 could affect the balance between proliferation and differentiation, human EN2 was over-expressed in a human neuronal cell line, SH-SY5Y, a cell line that can be differentiated in vitro. Transfected cells were identified by co-transfection with a GFP expression plasmid. Over-expression of EN2 caused a ~75% decrease in proliferation as measured by the number of cells positive for the marker, Ki67. Concomitant with this decrease in proliferation, elevated levels of EN2 also promoted differentiation as measured by the length of neuritis. These data indicate that EN2 promotes cell cycle exit and neuronal differentiation. Thus, increased levels of EN2 in individuals with autism could impact neuronal proliferation and differentiation, and significantly affect brain development.

To investigate whether small molecules that inhibit EN2 could reverse these phenotypes, the above experiments were repeated with siRNAS that target EN2. Inhibition of EN2 rescued the proliferation and differentiation effects of over-expression and caused the cells to proliferate and differentiate normally, i.e., at or near the level of controls. Thus, molecules that inhibit EN2 expression (e.g., siRNAs) or activity (e.g. anti-EN2 antibodies) would be of use in the treatment of autism.

What is claimed is:

1. A diagnostic kit indicative of the predisposition for developing autism spectrum disorder in a human comprising:
   one or more detectably labeled oligonucleotide probes 17 to 100 nucleotides in length which are perfectly complementary to a target sequence comprising a single nucleotide polymorphism in the ENGRAILED 2 intronic sequence of SEQ ID NO:11, wherein the single nucleotide polymorphism is an A at position 2236 of SEQ ID NO:11; and
   one or more detectably labeled oligonucleotide probes 17 to 100 nucleotides in length which are perfectly complementary to a target sequence comprising a single nucleotide polymorphism in the ENGRAILED 2 intronic sequence of SEQ ID NO:11, wherein the single nucleotide polymorphism is a C at position 2388 of SEQ ID NO:11,
   wherein said probes are detectably labeled with a radioactive element, a chemical which fluoresces or an enzyme.

2. The diagnostic kit of claim 1 wherein the one or more detectably labeled oligonucleotide probes are 17 to 50 nucleotides in length.

* * * * *

SEQUENCE LISTING

```
<160> NUMBER OF SEQ ID NOS: 107

<210> SEQ ID NO 1
<211> LENGTH: 10088
<212> TYPE: DNA
<213> ORGANISM: Homo sapiens

<400> SEQUENCE: 1
ctctcaccag ccctattttc ccggggggca ggtagactgt ggggtttgat ttttgagac        60 tcggggagga cccctggcag atgtgtgcct agccagaaca tttggtaagg actcctccaa     120
tgaagaaaaa gtggaggaat ccagccccag cgagaagagg cttccccacc ctgccctaga     180
cacaccggac agagggcaca ctctgaccag agccacgtcc agtggccagg aggccagccc     240
```

```
agcacctcct cccccaccat tcccgtcctg ggtgggggg taattttcct gggagcagct    300
gtgggaactg tcgtttctca tcccagccca gccagcactc tgaagcctgc agggaagga    360 cagcacgtgg gatggacact ggggaaggag cttcgcaagg ccagggtgca accttcaggc    420
cccaggtggc ctggcaggcc acgctgcctc ggagatgctt gccagactcc caagttcac    480 tcagggcctg gcagcaacct gctggctgcc tctgcggggg tctggttgc tgagcacggt    540 gcagctgccc agggccaatc agccctaggg tgtccgtgcc aggctgcggc ctccccgcct    600
cccccgcact gagggtactc atggcgtgca aatgctcccg cacccccaga gctgccctat    660
cggatgtttc caggaattca cacatttcca taaaaatgca ttttaaatga tggacaggcg    720
agcctggggt aacaacgggt gtttggtggg tagacaagag caaatgggaa ggagcccgag    780
ggaggagggg gaagagaaga ggaaacagaa cttccagttg gacattctga caacagctgg    840
aaggaaagtc tagaaaagat gaagagagag gaggggagaa accaactggg gctcccaccc    900
ttgccgttgg attcctaatt ctcgtttcaa atgggccctg ctctccggca aaattagttt    960
aaaggatttt aaaacaaaga aaacgagatg accggtctgg gagctcctca atcagagtag    1020
agaagttaga gggggggcgg gcgacttggtt ttgaagtctt agctgaacag tcacccctcc    1080
tctccttggc aaaaaggatt cctttagaac ctccgaggct cctggatttc tcccttcgca    1140
aatggagccg catactgcat tccccccgctc tttcggatcg ctaagcatgt ttcatgaggg    1200
tcgctgtccc cgggtggaat gcggccgtat gcacgcgcct ccctgcacac gcacacacac    1260
gcacacttac aataagtgtc tgcaggagga gtgtcctgcg cgccagctct gcgtttaaga    1320
caggaagctg ccgggttacc gagtcaaatg ggagtgacac tattcctctc catcagcaag    1380
gaaagcggac cacaaaagtc cctttgtatc tcggcagctc atttaatatt atttatgcat    1440
tttgtgcaag gaattgtggg atttcgcccc acggtaaaca atatggaaat cttaaaaata    1500
gcgatcttcc tgtgcgtgtc cacctacgcg ccccggggtg acctggcggg gctgtcgccg    1560
ggtgactcac accccctgaac cgcgaagcga caggaaaagc gcgggcgagc gcaggagacg    1620
cggtcggggg tctctccggg ttcctgggct cccgcacccg gagcggggga cgcggccgct    1680
ttaaggggag gaggggcggc gggctgctcc tgtcacccag cggcggccgg agcgtcacgt    1740
gggcgcgcgg cgccgcggcc attggcccga ggcacgtgtc caggagaccg gcctgcgacg    1800
tcactcgagg gggctctgtt aaaaataaga acaaaaatcc agagtgaaag tgtctcaggt    1860
tgcgccgagt ggcctggaaa tttccgagcc cgcgcggagg ccgaggcggc gagggcggcg    1920
gacggccggg gagcgcgggc ggcccagccc ggcccgccg ggccctggcc tcgcgtctct    1980
cacccatgcg actcgggccg cggagctctg cggggctcgg cggggggcgcg ccgcacgcc    2040 ggtggggcgc cccggcccgc agcggggcgg cggccgcgag gagggggcct ccatgtgcgt    2100
gcgggcggtg gcgggcgcgc tgaccgcggg cgcccggcac cctcgagggc cggctagggc    2160
gtgcgggcgg ggacggccgg gcgcggcggg cggccggagc cggccgggc gggcgtgagc    2220 gccgggaac gcgctgcctg catgcgcgca gctctcgccc cgggcggccc aggcggcggc    2280
gccggagccc gaggcggccg gacgcggaga ggagcgggga gcccgggagg cggcccgcgt    2340
ccccgccgga ccactgcgac tgtctagacc ccggctgcgc ggcgaagtcg aggacttggc    2400
tctgttgaat ctctcatcgt ctgggcgagc ggggcggctc gtggtgtttc taacccagtt    2460
cgtggattca aaggtggctc cgcgccgagc gcggccggcg acttgtagga cctcagccct    2520
ggccgcggcc gccgcgcacg ccctcggaag actcggcggg gtggggcgc ggggtctcc    2580 gtgtgcgccg cgggagggcc gaaggctgat ttggaagggc gtccccggag aaccagtgtg    2640
```

```
ggatttactg tgaacagcat ggaggagaat gaccccaagc ctggcgaagc agcggcggcg    2700
gtggagggac agcggcagcc ggaatccagc cccggcggcg gctcgggcgg cggcggcggt    2760
agcagcccgg gcgaagcgga caccgggcgc cggcgggctc tgatgctgcc cgcggtcctg    2820
caggcgcccg gcaaccacca gcacccgcac cgcatcacca acttcttcat cgacaacatc    2880
ctgcggcccg agttcggccg gcgaaaggac gcggggacct gctgtgcggg cgcgggagga    2940
ggaaggggcg gcggagccgg cggcgaaggc ggcgcgagcg gtgcggaggg aggcggcggc    3000
gcgggcggct cggagcagct cttgggctcg ggctcccgag agccccggca gaacccgcca    3060
tgtgcgcccg gcgcgggcgg gccgctccca gccgccggca gcgactctcc gggtgacggg    3120
gaaggcggct ccaagacgct ctcgctgcac ggtggcgcca agaaaggcgg cgaccccggc    3180
ggccccctgg acgggtcgct caaggcccgc ggcttgggcg gcggcgacct gtcggtgagc    3240
tcggactcgg acagctcgca agccggcgcc aacctgggcg cgcagcccat gctctggccg    3300
gcgtgggtct actgtacgcg ctactcggac cggccttctt caggtgagcc gcgggggacc    3360
acgcgtcccg gctcgccgcg gggaggcccg cggagctggg gggcggtgct ggcgcgggaa    3420
cttaccggga ggaaaacatc tcgaacctcc ccgcgcaca cgcacaaaga ctcacgcgac    3480
attgtgtgaa gctgacgccg gcccgggcag cggccaggag tccagcggca ggactgattc    3540 gctaggggt acagacttct taggaccgca aagggacct tctttctttc tctgtctctc    3600
tctctccttc ctctctccct gtctcccctc tctgtcttcc accccgcctt ggcgcatctc    3660
ttcccagccc ctagcccatg tctccccac tgtagttttt tttggtggga acgtggtggc    3720
tggaagatgg gcccggaagt gcacactctc atcccctccc ctacgatctt ccaactcagg    3780
ccaggccggg gacgcatgcc ccagcccacc ccagacttgt cctaccatcc ggttatcccg    3840
gctgtgctcg gggaagaaaa ggcgaggccc tttgccgctc tgccttctgc ccctcgggcc    3900
tgcgctgacc ggtgggactc aggaggatgc acacagggaa ggaggaaaat aaaggcgccc    3960 tttcccttg gctccacttt gtttgccagc gccagcccgc agtggtgggg ctcagccccc    4020
ttcctgcaca cagcgaggac aagggaggca gccgtccctc ccggcacctg ccatccccaa    4080
atagaaagga ccttctctca gggtttcctg ggggctgctg atgggaaaga ggcagcattc    4140 gcagggccc tgcagagatg ctggatatat tttttcatag atctgcgatt ttaaaaaact    4200
aagtccatgt ccttgtagaa atcatcaact gcattccatg cgggtctgcg gctgggaacc    4260
gccattagaa gtggactgtt tgaccccgag ctggcagcgg atccccgctg ccccaaaacc    4320
ctcaactatt ttgcggggt catttgccca gatcacagca ggagtgagcc aacccttggg    4380
ccgccatccc gcagaactat gcgtgcatat ttctgatgaa attcagattt ctcagctaga    4440
tctgaaattt gctccattgt tctcgtcttc tccctttgtt aatatttaat taacatacag    4500
gctcacaatg ccgggcgagg agactcggcc gggctttgtg cggcgcggga gttcgctgag    4560
ccagccccca acgcccggg agctgggcag caccgcccgg cccggcctgg ccggcccag    4620 ctcagcccag cccaagtcgc ctatcttcat gggctttaaa atatccctgc aagataatgt    4680
ttctgttctt tggtttctcc gaaagaaagg ggagagagag ttttcttggg gaggtttgat    4740
tctgtttctg agactcctaa gtatttgtct tttgaaagaa aatcaagaaa aaacctaaa    4800 aattattatt ttagggaaat ttattgccat aaaatggtgt cctttgcgg gctgcttcat    4860 gagtgcatta acaagagccc caggaccaga agagtttggg ggtagagttc tggggaaggg    4920
agtggttgga aacccagaca gagatgggct ctgggagcag gaggctgggg cctctcctgg    4980
```

-continued

```
agccttgtgc cccatccccc accaccgttc cggagggcca accccatctc caaatctgca    5040
cctacccta  ccaaagccag gcccactggc ctggagccct gggcgtgagc aagacaggca     5100
ctgagtgtgt acgtgtgcat ggggtgggtg cccaagtata gggtgtgtgc tctcatgggt    5160
ggtgagcctg cctatggttt gctttaaaag ctgcccttgg tgctcctgag gtggtgccca    5220
cagatcctct ttctccaggc ctgtctcctg gagagagcac aagactcact tggccatgag    5280
ggagtgcttg gcattcaccc tgggcctcca gttcgtcccc cacctcttgc tgggcacagc    5340
cccagcaccc tagttgactc tcctgacctg ggcagggtgc agtcccaggg cctccaagga    5400
gatccacatt cctcttctcc tcagtgtgcc cggcagctct ccggccctga agggtggggg    5460
gcccccagcc ttctccagcc acagggacct gtgatgaagc tggggccaga tgctccctaa    5520
agccgattca tacaccgcac aaattgaaac ccagaggcga ggtcaccact ccctgccagt    5580
ggccttgccc ccttcttccc ccacagggaa cgccaggggg ttgagcctct tatcaccaaa    5640
aagaaactga tgacacttcc ctccttctgc tctcctccct ctgcccttc  ccatggata     5700
gcaggtccta gaagccttac agcgaccctg tccaaaacct ggggcaggtc cacagggaga    5760
aggccaggtc aggttcataa gtctgaatcc cagttgggag gcacagtggg gagggtcaga    5820
agtggacctg gacaaggtca gctgggctac cctgctgccc acagtgaagc agtcccatgt    5880
ctggggaaag ggtggtgcag tcaacaccct tgtagagcca ggtcccctct cctggacagg    5940
aaacctggga gatttccagt gggtgaagga ctcaccact  gtgagtagct cagtgccct     6000
ccccaccaag gagggaagta catgcactga ctcttcctta aaggaatgaa cttgggtcca    6060
cagagccctt ggctgggagt catagaggag cttgggtgga ggcagacact ctgggccct    6120
cctgtcctca gggcccacct gcccctgatt cccacagccc ttggcaccct gtggggtatc    6180
cccatgaggt tccccatcat agccctcagg gcgcctcctg cttctgtgac cgccctgcag    6240
cctttcccag tcttctctcc tcccctctct ctcagcacct accgccatcc ctgttcctga    6300
acagagagcc tcagaaagga ctaggaaaaa ccaggccaga aagtgtgggg agttttgctt    6360
acatccagga gttttacttt tatctagaga cccctcattt gtggtcagcc tgcccactag    6420
gcctgcccca tagtcccact tacatcacac gcagtcctcc ctcaccaagt ggtggaggtc    6480
cgcgttgagc ccatgcccag tccgaagtct agccccacat ctggcggttc agcctcgagt    6540
ggccttgggc gagtcacttc cctcttgggg ccccagaatc cttacccggt gcctattggg    6600
tggcacacct ctgggtaacc tgacttctct ctgtccaccg tatctaccca ggtcccaggt    6660
ctcgaaaacc aaagaagaag aacccgaaca aagaggacaa gcggccgcgc acggccttta    6720
ccgccgagca gctgcagagg ctcaaggccg agttccagac caacaggtac ctgacggagc    6780
agcggcgcca gagcctggcg caggagctga gcctcaacga gtcacagatc aagatttggt    6840
tccagaacaa gcgcgccaag atcaagaagg ccacgggcaa caagaacacg ctggccgtgc    6900
acctcatggc acagggcttg tacaaccact ccaccacagc caaggagggc aagtcggaca    6960
gcgagtaggg cggggggcat ggaggccagg tctcagtccg cgctaaacaa tgcaataatt    7020
taaaatcata aagggccagt gtataaagat tataccagca ttaatagtga aaatattgtg    7080
tattagctaa ggttctgaaa tattctatgt atatatcatt tacaggtggt ataaaatcca    7140
aaatatctga ctataaaata ttttttttgag ttttttgtgt ttatgagatt atgctaattt    7200
tatgggtttt tttcttttttt gcgaaggggg ctgcttaggg tttcacctttt ttttaatccc   7260
ctaagctcca ttatatgaca ttggacactt ttttattatt ccaaaagaag aaaaaattaa    7320
aacaacttgc tgaagtccaa agatttttta ttgctgcatt tcacacaact gtgaaccgaa    7380
```

```
taaatagctc ctatttggtc tatgacttct gccactttgt ttgtgttggc ttggtgagga    7440
cagcaggagg ggcccacacc tcaagcctgg accagccacc tcaaggcctt ggggagctta    7500
ggggacctgg tgggagagag gggacttcca gggtccttgg gccagttctg ggatttggcc    7560
ctgggaagca gcccagcgta ccccaggcct gctctgggaa gtcggctcca tgctcaccag    7620
cagccgccca ggcccgcagc ctcacccggc tccctctcct caccctcctg cacctaactc    7680
cctcctcctt ctccttttc ctcctcttcc tccttcctcc ttcctcctgc tcctcctttc    7740
ttcttctttt tcttctcctc ctcctccttc cttcctcctc ctccttctct ttcctcctcc    7800
tcctcaccaa gggcccaacc gtgtgcatac atcgtctgcg tctgtggtct gtgtcgctgt    7860
ccccagtccc accgcagtcc tgccgcaggc ctaaccctcc tgccctgggc actgcctcca    7920
tgcagaagcg cttcgaggtt ctggggctaa aggcctgggg tgtgtggcct aaagcccaag    7980
agcggtgggg cgaccctcct tttggcttgg ccccaggaat ttcctgtgac tccaccagcc    8040
atcatgggtg ccagccaggg tcccagaaat gaggccatgg ctcactgttt ctgggcgggc    8100
agaaggctct gtagagggag atggcatcat ctatcttcct ttccttttc ttttcttccc    8160 tattttttc ttttttcct ttattttttt cttttcttgg agtggctgct tctgctatag    8220
agaacattct tccaagataa atatgtgtgt ttacacatat gtctgcatgc atgtgaacac    8280
acacacacac acacacacac caggcgtgtt tgagtccaca gttctgaaac atgtggctac    8340
cttgtctttc aaaagaactc agaatcctcc aggatctaga agaaggaaga aagtgtgtaa    8400
ataatcattt cttatcatca ctttttgtct tttcttgttt tttaaaatat acattttatt    8460
tttgaaggtg tggtacagtg taaattaaat atattcaata tatttcccac caagtaccta    8520
tatatgtata taaacaaaca cattatctat atataacgcc acactgtctt ctgtttagtg    8580
tatggggaaa gaccaatcca actgtccatc tgtggctggg acagcccagg gggtgtgccc    8640
acggctgacc caggggtgtg cacacggctg agctgggagt cccgctggtc tccctgagga    8700
ctgagggtga acttcgctct ttgccttaaa cctctttatt tcattgcagt aatagtttta    8760
cgttgtacat aatagtgtaa accttttaa aaaggaaagt ataaaaacaa aagttgtaat    8820
ttaaaagtct gaataaccat ctgctgctta ggaaactcaa tgaaatgaca tgccttttta    8880
gcaggaagca aagttggttt ctgttttttg ttttctttgt tgtttagtt tataaaacat    8940 gtgcatttta cagttccagt atcaaatatt tataatctta tgagaaatga atgaatgttt    9000
ctatttacaa ctgtgcttat caaaattgtg aacacccca ccccgcatt tttgtgtgtt    9060 gaaattcttg aaggttacat taaataaaac aaaatctctt tattataaaa tactgaaggt    9120
cccaggtgga atgatgagtt ttctaagcat gtctgagtcc agaggaactg cctgggcatc    9180
ctccccagta ctcaggtgct catggccttc gccccgcctg ggagcaggtg ccaggtgcct    9240
ttgtagcgag aggtgattat tattttttt taaataagac agtttggata tgtcacatgt    9300
gagcacagaa taaccaaaag aagtacacat tttgttacca ggaggaagtg ttcaaaacta    9360
cggtgctatt ccagtgacta cattttttta aattttgcga agttcaacag gtctccctcc    9420
ggctgggtgc tcactggccc tgccacccgt gctggaccga ggcgctttcc cctggggaca    9480 ggaactttt actccactga gacaaagaga ctctcctttt caaagtgtca tttttgttta    9540
ccttttgttg tttccccccc aaaacaaaag actttgtaca acttcctaag caggattggg    9600
ggagggatca gcttcgcctg tgctgaccgc gcctctggat tccgctcatc aggaagtgtt    9660
tgggtctttt gagcgagtga tctacgcgtt gaattgctgt ttttccaaac tttcatggct    9720
```

```
taaaaatttt ttttcttctc cctgtaaaag aaactcagag actggtgatc tgttaccgaa   9780
gacgactttt taggcgtttt ctgtttcccc aggcagctgg gccgttggcg ttcccaggcg   9840 gaagcgggc ctctgggctg ggcctctgcc ctgccaggaa gcggtctggg ggctgcccct    9900
cgggattttc agaaccctgg aaggagagag ctggggtctc accgcggaga ctcccgagtt   9960
ctcgttgcct gggcccgagc tgcgccccag ggtcatcgct gatggcgcga gaccacgcat  10020
tccccgcgaa ccccgacttc tgaacagttc agaaagttcg tagattaaaa accaaacaaa  10080
aaatactg                                                            10088
```

<210> SEQ ID NO 2
<211> LENGTH: 333
<212> TYPE: PRT
<213> ORGANISM: Homo sapiens

<400> SEQUENCE: 2

```
Met Glu Glu Asn Asp Pro Lys Pro Gly Glu Ala Ala Ala Val Glu
1               5                   10                  15

Gly Gln Arg Gln Pro Glu Ser Ser Pro Gly Gly Ser Gly Gly
            20                  25                  30

Gly Gly Ser Ser Pro Gly Glu Ala Asp Thr Gly Arg Arg Ala Leu
            35                  40                  45

Met Leu Pro Ala Val Leu Gln Ala Pro Gly Asn His Gln His Pro His
50                  55                  60

Arg Ile Thr Asn Phe Phe Ile Asp Asn Ile Leu Arg Pro Glu Phe Gly
65                  70                  75                  80

Arg Arg Lys Asp Ala Gly Thr Cys Cys Ala Gly Ala Gly Gly Arg
            85                  90                  95

Gly Gly Gly Ala Gly Gly Glu Gly Gly Ala Ser Gly Ala Glu Gly Gly
            100                 105                 110

Gly Gly Ala Gly Gly Ser Glu Gln Leu Leu Gly Ser Gly Ser Arg Glu
            115                 120                 125

Pro Arg Gln Asn Pro Pro Cys Ala Pro Gly Ala Gly Gly Pro Leu Pro
130                 135                 140

Ala Ala Gly Ser Asp Ser Pro Gly Asp Gly Glu Gly Gly Ser Lys Thr
145                 150                 155                 160

Leu Ser Leu His Gly Gly Ala Lys Lys Gly Gly Asp Pro Gly Gly Pro
            165                 170                 175

Leu Asp Gly Ser Leu Lys Ala Arg Gly Leu Gly Gly Gly Asp Leu Ser
            180                 185                 190

Val Ser Ser Asp Ser Asp Ser Gln Ala Gly Ala Asn Leu Gly Ala
            195                 200                 205

Gln Pro Met Leu Trp Pro Ala Trp Val Tyr Cys Thr Arg Tyr Ser Asp
210                 215                 220

Arg Pro Ser Ser Gly Pro Arg Ser Arg Lys Pro Lys Lys Asn Pro
225                 230                 235                 240

Asn Lys Glu Asp Lys Arg Pro Arg Thr Ala Phe Thr Ala Glu Gln Leu
            245                 250                 255

Gln Arg Leu Lys Ala Glu Phe Gln Thr Asn Arg Tyr Leu Thr Glu Gln
            260                 265                 270

Arg Arg Gln Ser Leu Ala Gln Glu Leu Ser Leu Asn Glu Ser Gln Ile
            275                 280                 285

Lys Ile Trp Phe Gln Asn Lys Arg Ala Lys Ile Lys Lys Ala Thr Gly
            290                 295                 300
```

Asn Lys Asn Thr Leu Ala Val His Leu Met Ala Gln Gly Leu Tyr Asn
305                 310                 315                 320

His Ser Thr Thr Ala Lys Glu Gly Lys Ser Asp Ser Glu
                325                 330

<210> SEQ ID NO 3
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 3
tgaagctggg gccagatgct ccta                                      24

<210> SEQ ID NO 4
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 4
catggggaaa gggcagaggg aggag                                     25

<210> SEQ ID NO 5
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 5
aggcgaggtc accactccct gcaag                                     25

<210> SEQ ID NO 6
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 6
gggggaagaa gggggcaagg caat                                      24

<210> SEQ ID NO 7
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 7 gccaggggt tgagcctctt at                                         22

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
caggtccact tctgaccctc                                           20

```
<210> SEQ ID NO 9
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 9
gaagccttac agcgacccgg t                                              21

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
gacctgcccc aggttttttgg                                               20

<210> SEQ ID NO 11
<211> LENGTH: 3308
<212> TYPE: DNA
<213> ORGANISM: Homo sapiens

<400> SEQUENCE: 11
gtgagcccgc ggggaccacg cgtcccggct cgccgcgggg aggcccgcgg agctgggggg      60
cggtgctggc gcgggaactt accgggagga aaacatctcg aacctccccc gcgcacacgc    120
acaaagactc acgcgacatt gtgtgaagct gacgccggcc cgggcagcgg ccaggagtcc    180
agcggcagga ctgattcgct aggggtaca gacttcttag gaccgcagaa gggaccttct     240
ttctttctct gtctctctct ctccttcctc tctccctgtc tccctctct gtcttccacc     300 ccgccttggc gcatctcttc ccagccccta gcccatgtct ccccactgt agttttttt      360 ggtgggaacg tggtggctgg aagatgggcc cggaagtgca cactctcatc cccttcccta    420
cgatcttcca actcaggcca ggccggggac gcatgcccca gcccacccca gacttgtcct    480
accatccggt tatcccggct gtgctcgggg aagaaaaggc gaggcccttt gccgctctgc    540
cttctgcccc tcgggcctgc gctgaccggt gggactcagg aggatgcaca cagggaagga    600
ggaaaataaa ggcgcccttt ccccttggct ccactttgtt tgccagcgcc agcccgcagt    660 ggtgggctc agccccttc ctgcacacag cgaggacaag ggaggcagcc gtccctcccg      720
gcacctgcca tccccaaata gaaaggacct tctctcaggg tttcctgggg gctgctgatg    780
ggaaagaggc agcattcgca ggggccctgc agagatgctg gatatatttt ttcatagatc    840
tgcgatttta aaaaactaag tccatgtcct tgtagaaatc atcaactgca ttccatgcgg    900
gtctgcggct gggaaccgcc attagaagtg gactgtttga ccccgagctg gcagcggatc    960
cccgctgccc ccaaaccctc aactattttg cgggggtcat tgcccagat cacagcagga    1020 gtgagccaac ccttgggccg ccatcccgca gaactatgcg tgcatatttc tgatgaaatt    1080
cagatttctc agctagatct gaaatttgct ccattgttct cgtcttcctc ctttgttaat    1140
atttaattaa catacaggct cacaatgccg ggcgaggaga ctcggccggg ctttgtgcgg    1200
cgcgggagtt cgctgagcca gccccaacg gcccgggagc tgggcagcac cgcccggccc     1260
ggcctggccc ggcccagctc agcccagccc aagtcgccta tcttcatggg ctttaaaata    1320
tccctgcaag ataatgtttc tgttctttgg tttctccgaa agaaagggga gagagagttt    1380
tcttggggag gtttgattct gtttctgaga ctcctaagta tttgtctttt gaagaaaat    1440
```

```
caagaaaaaa acctaaaaat tattatttta gggaaattta ttgccataaa atggtgtcct    1500
tttgcgggct gcttcatgag tgcattaaca agagccccag gaccagaaga gtttgggggt    1560
agagttctgg ggaagggagt ggttggaaac ccagacagag atgggctctg ggagcaggag    1620
gctgggggcct ctcctggagc cttgtgcccc atccccacc accgttccgg agggccaacc    1680
ccatctccaa atctgcacct acccctacca aagccaggcc cactggcctg gagccctggg    1740
cgtgagcaag acaggcactg agtgtgtacg tgtgcatggg gtgggtgccc aagtataggg    1800
tgtgtgctct catgggtggt gagcctgcct atgggttgct ttaaaagctg cccttggtgc    1860
tcctgaggtg gtgcccacag atcctctttc tccaggcctg tctcctggag agagcacaag    1920
actcacttgg ccatgaggga gtgcttggca ttcaccctgg gcctccagtt cgtcccccac    1980
ctcttgctgg gcacagcccc agcaccctag ttgactctcc tgacctgggc agggtgcagt    2040
cccagggcct ccaaggagat ccacattcct cttctcctca gtgtgccggg cagctctccg    2100
gccctgaagg gtggggggcc cccagccttc tccagccaca gggacctgtg atgaagctgg    2160
ggccagatgc tccctaaagc cgattcatac accgcacaaa ttgaaaccca gaggcgaggt    2220
caccactccc tgccaatggc cttgccccct tcttccccca cagggaacgc caggggttg     2280
agcctcttat caccaaaaag aaactgatga cacttccctc cttctgctct cctccctctg    2340
cccttttcccc atggatagca ggtcctagaa gccttacagc gaccctgccc aaaacctggg    2400
gcaggtccac agggagaagg ccaggtcagg ttcataagtc tgaatcccag ttgggaggca    2460
cagtggggag ggtcagaagt ggacctggac aaggtcagct gggctaccct gctgcccaca    2520
gtgaagcagt cccatgtctg gggaaagggt ggtgcagtca acacccttgt agagccaggt    2580
cccctctcct ggacaggaaa cctgggagat ttccagtggg tgaaggactc acccactgtg    2640
agtagctcag tgcccctccc caccaaggag ggaagtacat gcactgactc ttccttaaag    2700
gaatgaactt gggtccacag agcccttggc tgggagtcat agaggagctt gggtggaggc    2760
agacactctg ggccctcct gtcctcaggg cccacctgcc cctgattccc acagcccttg    2820
gcaccctgtg gggtatcccc atgagggtcc ccatcatagc cctcagggcg cctcctgctt    2880
ctgtgaccgc cctgcagcct ttcccagtct tctctcctcc cctctctctc agcacctacc    2940
gccatccctg ttcctgaaca gagagcctca gaaaggacta ggaaaaacca ggccagaaag    3000
tgtggggagt tttgcttaca tccaggagtt ttacttttat ctagagaccc ctcatttgtg    3060
gtcagcctgc ccactaggcc tgccccatag tcccacttac atcacacgca gtcctccctc    3120
accaagtggt ggaggtccgc gttgagccca tgcccagtcc gaagtctagc cccacatctg    3180
gcggttcagc ctcgagtggc cttgggcgag tcacttccct cttggggccc cagaatcctt    3240
acccggtgcc tattgggtgg cacacctctg ggtaacctga cttctctctg tccaccgtat    3300
ctacccag                                                             3308
```

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
ctagagggaa aacgggggttc                                                    20

<210> SEQ ID NO 13
<211> LENGTH: 20

```
<212> TYPE: DNA
<213> ORGANISM: Artificial Sequence
<220> FEATURE:
<223> OTHER INFORMATION: Synthetic oligonucleotide

<400> SEQUENCE: 13
aactccgcaa ggtgtttcag                                                 20

<210> SEQ ID NO 14
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 14
tggcagatgt gtgcctag                                                   18

<210> SEQ ID NO 15
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 15
ccagaccggt catctcgttt tc                                              22

<210> SEQ ID NO 16
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 16
agagctgccc tatcggatgt t                                               21

<210> SEQ ID NO 17
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 17
aaactaattt tgccggagag c                                               21

<210> SEQ ID NO 18
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 18
cccaccaaac accc                                                       14

<210> SEQ ID NO 19
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 19
```

```
ctgtcggtga gctcggact                                                19
```

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20

```
tggaagacag agaggggaga                                               20
```

<210> SEQ ID NO 21
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 21

```
gcgacattgt gtgaagctga cg                                            22
```

<210> SEQ ID NO 22
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 22

```
gcgacattgt gtgaagctga cc                                            22
```

<210> SEQ ID NO 23
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 23

```
ccggcccggg cagcggc                                                  17
```

<210> SEQ ID NO 24
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 24

```
cgcatctctt cccagcccct agc                                           23
```

<210> SEQ ID NO 25
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 25

```
tgcatcctcc tgagtcccac cg                                            22
```

<210> SEQ ID NO 26
<211> LENGTH: 26
<212> TYPE: DNA
<213> ORGANISM: Artificial Sequence

```
<220> FEATURE:
<223> OTHER INFORMATION: Synthetic oligonucleotide

<400> SEQUENCE: 26
ccttccctac gatcttccaa ctcggg                                         26

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27
gcatgcgtcc ccggcctaga                                                20

<210> SEQ ID NO 28
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 28
cacagggaag gaggaaaata aa                                             22

<210> SEQ ID NO 29
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 29
tcatcagaaa tatgcacgca ta                                             22

<210> SEQ ID NO 30
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 30
agatctgcga ttttaaaaaa ctaact                                         26

<210> SEQ ID NO 31
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 31
ttgatgattt ctacaaggac aagg                                           24

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 32
cattaacaag agccccagga                                                20
```

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
ccatgagagc acacaccta                                           20

<210> SEQ ID NO 34
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 34
cagtgcctgt cttgc                                               15

<210> SEQ ID NO 35
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 35
tgcacctacc cctaccaaag cca                                      23

<210> SEQ ID NO 36
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 36
tgtggatctc cttggaggcc ct                                       22

<210> SEQ ID NO 37
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 37
ctccaaggag atccacattc ctctt                                    25

<210> SEQ ID NO 38
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 38
gggtcgctgt aaggcttcta ggac                                     24

<210> SEQ ID NO 39
<211> LENGTH: 22
<212> TYPE: DNA
<213> ORGANISM: Artificial Sequence
<220> FEATURE:
<223> OTHER INFORMATION: Synthetic oligonucleotide

```
<400> SEQUENCE: 39
cgagatgctc cctaaagccc aa                                       22

<210> SEQ ID NO 40
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 40
ggtttcaatt tgtgcggtga ttcaa                                    25

<210> SEQ ID NO 41
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 41
catacaccgc acaaattgaa ac                                       22

<210> SEQ ID NO 42
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 42
gattcagact tatgaacctg acctg                                    25

<210> SEQ ID NO 43
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 43
caccactccc tgcca                                               15

<210> SEQ ID NO 44
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 44
ccttacagcg accct                                               15

<210> SEQ ID NO 45
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 45
ccttctgctc tcctccctct                                          20

<210> SEQ ID NO 46
```

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 46
ggcctggttt ttcctagtcc                                            20

<210> SEQ ID NO 47
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 47
ccctcctgtc ctcagggcc                                             19

<210> SEQ ID NO 48
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 48
ccctcctgtc ctcagggct                                             19

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 49
cacctgcccc tgattcccac                                            20

<210> SEQ ID NO 50
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 50
gcccttggct gggagtcata ga                                         22

<210> SEQ ID NO 51
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 51
gggactatgg ggcaggccta gt                                         22

<210> SEQ ID NO 52
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 52
```

```
tttcccagtc ttctctcctc cacc                                        24
```

<210> SEQ ID NO 53
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 53

```
gcggtaggtg ctgagagcga                                             20
```

<210> SEQ ID NO 54
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 54

```
agtcttctct cctcccctct ct                                          22
```

<210> SEQ ID NO 55
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 55

```
gaggactgcg tgtgatgtaa gt                                          22
```

<210> SEQ ID NO 56
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 56

```
gaaagtgtgg ggagttttga tt                                          22
```

<210> SEQ ID NO 57
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 57

```
tctagataaa agtaaaactc ctggat                                      26
```

<210> SEQ ID NO 58
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 58

```
ccgccatccc tgttcctgaa ca                                          22
```

<210> SEQ ID NO 59
<211> LENGTH: 22
<212> TYPE: DNA

<213> ORGANISM: Artificial Sequence
<220> FEATURE:
<223> OTHER INFORMATION: Synthetic oligonucleotide

<400> SEQUENCE: 59
gtgtgccacc caataggcac cg                                      22

<210> SEQ ID NO 60
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 60
ccctcaccaa gtggtggagg tcagt                                   25

<210> SEQ ID NO 61
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 61
gactgggcat gggctcaccg                                         20

<210> SEQ ID NO 62
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 62
gtttgtgttg gcttggtgag                                         20

<210> SEQ ID NO 63
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 63
ccctctacag agccttctgc                                         20

<210> SEQ ID NO 64
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 64
cctctcctca ccctcctgcg                                         20

<210> SEQ ID NO 65
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 65
cctctcctca ccctcctgca                                         20

<210> SEQ ID NO 66
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 66
ctaactccct cctccttctc c                                              21

<210> SEQ ID NO 67
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 67
ctgtcggtga gctcggactc gg                                             22

<210> SEQ ID NO 68
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 68
gccctgcaga gatgctggat atat                                           24

<210> SEQ ID NO 69
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 69
tagaaaggac cttctctcag gg                                             22

<210> SEQ ID NO 70
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 70
gtggttggaa acccagacag agat                                           24

<210> SEQ ID NO 71
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 71
cattaacaag agccccagga ccagaag                                        27

<210> SEQ ID NO 72
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 72
gacaaggtca gctgggctac                                              20

<210> SEQ ID NO 73
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 73
ttccccatgg atagcaggtc ctag                                         24

<210> SEQ ID NO 74
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 74
ggtctcgaaa accaaagaag aagaacccga                                   30

<210> SEQ ID NO 75
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 75
gtgaagtatg gaggagaagg                                              20

<210> SEQ ID NO 76
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 76
ctaaacagtc ccctttgcag                                              20

<210> SEQ ID NO 77
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 77
aaccgtgaac aaaaggccag tg                                           22

<210> SEQ ID NO 78
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 78
ctaaacagtc ccctttgcag                                              20

```
<210> SEQ ID NO 79
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 79
tcaacgagtc acagatcaa                                                  19

<210> SEQ ID NO 80
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 80
ucaacgaguc acagaucaa                                                  19

<210> SEQ ID NO 81
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 81
aguugcucag ugucuaguu                                                  19

<210> SEQ ID NO 82
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 82
ccaacttctt catcgacaa                                                  19

<210> SEQ ID NO 83
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 83
ccaacuucuu caucgacaa                                                  19

<210> SEQ ID NO 84
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 84
gguugaagaa guagcuguu                                                  19

<210> SEQ ID NO 85
<211> LENGTH: 19
<212> TYPE: DNA
<213> ORGANISM: Artificial Sequence
<220> FEATURE:
<223> OTHER INFORMATION: Synthetic oligonucleotide
```

```
<400> SEQUENCE: 85
ctcgaaaacc aaagaagaa                                               19

<210> SEQ ID NO 86
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 86
cucgaaaacc aaagaagaa                                               19

<210> SEQ ID NO 87
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 87
gagcuuuugg uuucuucuu                                               19

<210> SEQ ID NO 88
<211> LENGTH: 9
<212> TYPE: PRT
<213> ORGANISM: Artificial Sequence
<220> FEATURE:
<223> OTHER INFORMATION: Synthetic peptide

<400> SEQUENCE: 88

Arg Lys Lys Arg Arg Gln Arg Arg Arg
1               5

<210> SEQ ID NO 89
<211> LENGTH: 13
<212> TYPE: PRT
<213> ORGANISM: Artificial Sequence
<220> FEATURE:
<223> OTHER INFORMATION: Synthetic peptide

<400> SEQUENCE: 89

Gly Arg Lys Lys Arg Arg Gln Arg Arg Arg Pro Pro Gln
1               5                   10

<210> SEQ ID NO 90
<211> LENGTH: 14
<212> TYPE: PRT
<213> ORGANISM: Artificial Sequence
<220> FEATURE:
<223> OTHER INFORMATION: Synthetic peptide

<400> SEQUENCE: 90

Val Ser Arg Arg Arg Arg Arg Gly Gly Arg Arg Arg Arg
1               5                   10

<210> SEQ ID NO 91
<211> LENGTH: 21
<212> TYPE: PRT
<213> ORGANISM: Artificial Sequence
<220> FEATURE:
<223> OTHER INFORMATION: Synthetic peptide

<400> SEQUENCE: 91

Lys Glu Thr Trp Trp Glu Thr Trp Trp Thr Glu Trp Ser Gln Pro Lys
1               5                   10                  15
```

```
Lys Lys Arg Lys Val
            20

<210> SEQ ID NO 92
<211> LENGTH: 16
<212> TYPE: PRT
<213> ORGANISM: Artificial Sequence
<220> FEATURE:
<223> OTHER INFORMATION: Synthetic peptide

<400> SEQUENCE: 92

Arg Gln Ile Lys Ile Trp Phe Gln Asn Arg Arg Met Lys Trp Lys Lys
1               5                   10                  15

<210> SEQ ID NO 93
<211> LENGTH: 27
<212> TYPE: PRT
<213> ORGANISM: Artificial Sequence
<220> FEATURE:
<223> OTHER INFORMATION: Synthetic peptide

<400> SEQUENCE: 93

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 94
<211> LENGTH: 18
<212> TYPE: PRT
<213> ORGANISM: Artificial Sequence
<220> FEATURE:
<223> OTHER INFORMATION: Synthetic peptide

<400> SEQUENCE: 94

Val Arg Leu Pro Pro Pro Val Arg Leu Pro Pro Pro Val Arg Leu Pro
1               5                   10                  15

Pro Pro

<210> SEQ ID NO 95
<211> LENGTH: 9
<212> TYPE: PRT
<213> ORGANISM: Artificial Sequence
<220> FEATURE:
<223> OTHER INFORMATION: Synthetic peptide

<400> SEQUENCE: 95

Arg Arg Arg Arg Arg Arg Arg Arg Arg
1               5

<210> SEQ ID NO 96
<211> LENGTH: 18
<212> TYPE: PRT
<213> ORGANISM: Artificial Sequence
<220> FEATURE:
<223> OTHER INFORMATION: Synthetic peptide

<400> SEQUENCE: 96

Lys Leu Ala Leu Lys Leu Ala Leu Lys Ala Leu Lys Ala Ala Leu Lys
1               5                   10                  15

Leu Ala

<210> SEQ ID NO 97
<211> LENGTH: 12
```

```
<212> TYPE: PRT
<213> ORGANISM: Artificial Sequence
<220> FEATURE:
<223> OTHER INFORMATION: Synthetic peptide

<400> SEQUENCE: 97

Lys Ala Leu Ala Lys Ala Leu Ala Lys Ala Leu Ala
1               5                   10

<210> SEQ ID NO 98
<211> LENGTH: 16
<212> TYPE: PRT
<213> ORGANISM: Artificial Sequence
<220> FEATURE:
<223> OTHER INFORMATION: Synthetic peptide

<400> SEQUENCE: 98

Ala Ala Val Ala Leu Leu Pro Ala Val Leu Leu Ala Leu Leu Ala Pro
1               5                   10                  15

<210> SEQ ID NO 99
<211> LENGTH: 16
<212> TYPE: PRT
<213> ORGANISM: Artificial Sequence
<220> FEATURE:
<223> OTHER INFORMATION: Synthetic peptide

<400> SEQUENCE: 99

Arg Gln Ile Lys Ile Trp Phe Gln Asn Arg Arg Met Lys Trp Lys Lys
1               5                   10                  15

<210> SEQ ID NO 100
<211> LENGTH: 21
<212> TYPE: PRT
<213> ORGANISM: Artificial Sequence
<220> FEATURE:
<223> OTHER INFORMATION: Synthetic peptide

<400> SEQUENCE: 100

Thr Arg Ser Ser Arg Ala Gly Leu Gln Phe Pro Val Gly Arg Val His
1               5                   10                  15

Arg Leu Leu Arg Lys
            20

<210> SEQ ID NO 101
<211> LENGTH: 26
<212> TYPE: PRT
<213> ORGANISM: Artificial Sequence
<220> FEATURE:
<223> OTHER INFORMATION: Synthetic peptide

<400> SEQUENCE: 101

Gly Trp Thr Leu Asn Ser Ala Gly Tyr Leu Leu Gly Lys Ile Asn Lys
1               5                   10                  15

Ala Leu Ala Ala Leu Ala Lys Lys Ile Leu
            20                  25

<210> SEQ ID NO 102
<211> LENGTH: 5
<212> TYPE: PRT
<213> ORGANISM: Artificial Sequence
<220> FEATURE:
<223> OTHER INFORMATION: Synthetic peptide

<400> SEQUENCE: 102

Val Pro Met Leu Lys
```

```
<210> SEQ ID NO 103
<211> LENGTH: 28
<212> TYPE: PRT
<213> ORGANISM: Artificial Sequence
<220> FEATURE:
<223> OTHER INFORMATION: Synthetic peptide

<400> SEQUENCE: 103

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 104
<211> LENGTH: 19
<212> TYPE: PRT
<213> ORGANISM: Artificial Sequence
<220> FEATURE:
<223> OTHER INFORMATION: Synthetic peptide

<400> SEQUENCE: 104

Leu Leu Ile Ile Ile Leu Arg Arg Arg Ile Arg Lys Gln Ala His Ala
1               5                   10                  15

His Ser Lys

<210> SEQ ID NO 105
<211> LENGTH: 15
<212> TYPE: PRT
<213> ORGANISM: Artificial Sequence
<220> FEATURE:
<223> OTHER INFORMATION: Synthetic peptide

<400> SEQUENCE: 105

Ser Asp Leu Trp Glu Met Met Met Val Ser Leu Ala Cys Gln Tyr
1               5                   10                  15

<210> SEQ ID NO 106
<211> LENGTH: 12
<212> TYPE: PRT
<213> ORGANISM: Artificial Sequence
<220> FEATURE:
<223> OTHER INFORMATION: Synthetic peptide

<400> SEQUENCE: 106

Thr Ser Pro Leu Asn Ile His Asn Gly Gln Lys Leu
1               5                   10

<210> SEQ ID NO 107
<211> LENGTH: 26
<212> TYPE: PRT
<213> ORGANISM: Artificial Sequence
<220> FEATURE:
<223> OTHER INFORMATION: Synthetic peptide

<400> SEQUENCE: 107

Lys Trp Lys Ser Phe Ile Lys Lys Leu Thr Ser Ala Ala Lys Lys Val
1               5                   10                  15

Val Thr Thr Ala Lys Pro Leu Ile Ser Ser
            20                  25
```